United States Patent
Kriz et al.

(10) Patent No.: US 11,530,258 B2
(45) Date of Patent: Dec. 20, 2022

(54) USE OF SRSF3 AGENTS FOR THE TREATMENT AND/OR PREVENTION OF NEUROLOGICAL CONDITIONS, CANCER, BACTERIAL INFECTIONS OR VIRAL INFECTIONS

(71) Applicant: Université Laval, Québec (CA)

(72) Inventors: Jasna Kriz, Québec (CA); Hejer Boutej, Québec (CA)

(73) Assignee: Université Laval, Québec (CA)

( * ) Notice: Subject to any disclaimer, the term of this patent is extended or adjusted under 35 U.S.C. 154(b) by 40 days.

(21) Appl. No.: 16/763,906

(22) PCT Filed: Nov. 15, 2018

(86) PCT No.: PCT/CA2018/051452
§ 371 (c)(1),
(2) Date: May 13, 2020

(87) PCT Pub. No.: WO2019/095064
PCT Pub. Date: May 23, 2019

(65) Prior Publication Data
US 2021/0171615 A1 Jun. 10, 2021

Related U.S. Application Data

(60) Provisional application No. 62/586,567, filed on Nov. 15, 2017.

(51) Int. Cl.
| | |
|---|---|
| C07K 16/18 | (2006.01) |
| A61P 9/10 | (2006.01) |
| A61P 25/28 | (2006.01) |
| A61K 9/00 | (2006.01) |
| C12N 15/113 | (2010.01) |
| G01N 33/68 | (2006.01) |

(52) U.S. Cl.
CPC ............ *C07K 16/18* (2013.01); *A61K 9/0043* (2013.01); *A61P 9/10* (2018.01); *A61P 25/28* (2018.01); *C12N 15/113* (2013.01); *G01N 33/6875* (2013.01); *C07K 2317/24* (2013.01); *C07K 2317/34* (2013.01); *C07K 2317/74* (2013.01); *C07K 2317/76* (2013.01); *C12N 2310/11* (2013.01); *C12N 2310/14* (2013.01); *C12N 2310/3233* (2013.01); *C12N 2320/32* (2013.01)

(58) Field of Classification Search
None
See application file for complete search history.

(56) References Cited

U.S. PATENT DOCUMENTS

| | | |
|---|---|---|
| 2007/0015172 A1 | 1/2007 | Zhang et al. |
| 2011/0172172 A1 | 7/2011 | Addington et al. |
| 2015/0218640 A1 | 8/2015 | Brandon et al. |
| 2015/0233942 A1 | 8/2015 | Wong |
| 2017/0107300 A1 | 4/2017 | Kuchroo et al. |

FOREIGN PATENT DOCUMENTS

WO 2012/045067 A2 4/2012

OTHER PUBLICATIONS

Reitz "Toward precision medicine in Alzheimer's disease" Ann transl med 4(6):107 (Year: 2016).*
Stanford "Alzheimer's prevention, treatment and research—A Q and A with Dr Frank Longo" accessed from Stanfordhealthcare.org on May 3, 2016 (Year: 2016).*
Pratt "Amyotrophic lateral sclerosis: update and new developments" degen neurol neuromuscul 2:1-14 (Year: 2012).*
Farmer "hematopoietic cytokines as therapeutic players in early stages Parkinson's disease" front aging neuro 7:126 (Year: 2015).*
Murphy "Neuroinflammation in schizophrenia: the role of nuclear factor kappa B" trans psych 11:528 (Year: 2021).*
Ajiro "Adapted Resistance to the Knockdown Effect of shRNA-Derived Srsf3 siRNAs in Mouse Littermates" intj biol sci 11 (Year: 2015).*
Boutej "Diverging mRNA and Protein Networks in Activated Microglia Reveal SRSF3 Suppresses Translation of Highly Upregulated Innate Immune Transcripts" cell report 21:3220-3233 (Year: 2017).*
Kano, Shizuka , et al., "Oxidative stress-inducible truncated serine/arginine-rich splicing factor 3 regulates interleukin-8 production in human colon cancer cells", Am J Physiol Cell Physiol 306, 2014, C250-C262.
Keren-Shaul, Hadas , et al., "A Unique Microglia Type Associated with Restricting Development of Alzheimer's Disease", Cell 169, 2017, 1276-1290.
Krasemann, Susanne , et al., "The TREM2-APOE Pathway Drives the Transcriptional Phenotype of Dysfunctional Microglia in Neurodegenerative Diseases", Immunity 47, 2017, 566-581.
Moura-Alves, Pedro , et al., "An shRNA-Based Screen of Splicing Regulators Identifies SFRS3 as a Negative Regulator of IL-1 b Secretion", PLoS One 6(5), 2011, e19829 (pp. 1-10).
Park, Seung Kuk, et al., "SRSF3 represses the expression of PDCD4 protein by coordinated regulation of alternative splicing, export and translation", Biochemical and Biophysical Research Communications 470, 2016, 431-438.
Boutej et al. (2017) "Diverging mRNA and Protein Networks in Activated Microglia Reveal SRSF3 Suppresses Translation of Highly Upregulated Innate Immune Transcripts" Cell Reports 21: 3220-3233.
Huang and Steitz (2001) "Splicing Factors SRp20 and 9G8 Promote the Nucleocytoplasmic Export of mRNA" Molecular Cell 7: 899-905.
Wong et al. (2012) "Srp20 regulates TrkB pre-mRNA splicing to generate TrkB-Shc transcripts with implications for Alzheimer's disease" Journal of Neurochemistry 123: 159-171.

(Continued)

Primary Examiner — Adam Weidner
(74) Attorney, Agent, or Firm — Bozicevic, Field & Francis LLP; Edward J. Baba

(57) ABSTRACT

The present description relates to the use of a SRSF3 agent for regulating the function of a myeloid cell, such as a microglial cell and/or monocyte, for treating neurological conditions, cancers, bacterial infections and viral infections wherein the SRSF3 agent inhibits expression or function of SRSF3.

15 Claims, 45 Drawing Sheets
(35 of 45 Drawing Sheet(s) Filed in Color)
Specification includes a Sequence Listing.

(56) References Cited

OTHER PUBLICATIONS

Wong et al. (2013) "Digoxin Suppresses HIV-1 Replication by Altering Viral RNA Processing" PLoS Pathogens 9(3): e1003241, 16 pages.
International Search Report received for PCT Application Serial No. PCT/CA2018051452 dated Feb. 26, 2019, 6 pages.
Written Opinion of the International Searching Authority received for PCT Application Serial No. PCT/CA2018051452 dated Feb. 26, 2019, 7 pages.
Dawaele et al. (2016) "Antisense oligonucleotide-mediated MDM4 exon 6 skipping impairs tumor growth" The Journal of Clinical Investigation 126(1): 68-84.
Liu et al. (2013) "Cardiac glycosides correct aberrant splicing of IKBKAP-encoded mRNA in familial dysautonomia derived cells by suppressing expression of SRSF3" The FEBS Journal 280(15): 3632-3646.
Tang et al. (2013) "Downregulation of splicing factor SRSF3 induces p53β, an alternatively spliced isoform of P53 that promotes cellular senescence" Oncogene 32:2792-2798.
Watanuki et al. (2008) "Increased expression of splicing factor SRp20 mRNA in bipolar disorder patients" Journal of Affective Disorders 110: 62-69.
European Search Report (Supplementary Partial) received for EP 18879970.4 dated Jul. 1, 2021, 10 pages.
European Search Report (Supplementary) received for EP 18879970.4 dated Oct. 12, 2021, 14 pages.

\* cited by examiner

A

B

329bp

C

C

| Gene Symbol | Description | Detected as mRNA | mRNA fold change (linear) | Detected as peptide | Peptide fold change |
|---|---|---|---|---|---|
| Saa3 | Serum amyloid A3 | √ | 29.52 | X | - |
| Lcn2 | Lipocalin2 | √ | 23.71 | X | - |
| Ccl5 | Chemokine (C-C motif) ligand 5 | √ | 15.93 | X | - |
| Irf7 | Interferon regulatory factor 7 | √ | 7.8 | X | - |
| Ccl3 | Chemokine (C-C motif) ligand 3 | √ | 5.19 | X | - |
| Gm7676 | Interferon induced transmembrane protein 1 pseudogene | √ | 4.95 | X | - |
| Ywhaz | 14-3-3 protein zero/delta | √ | 1.03 | √ | 1.01 |
| Cap2 | Adenylyl cyclase-associated protein 2 | √ | -1.25 | √ | -1.09 |

| Symbol | Name | Fold Change | p- value | Number of Srsf3 binding sites at 3'UTR |
|---|---|---|---|---|
| *Clec7a* | C-type lectin domain family 7 member A | 38,04 | 0,024969 | *16* |
| Olfr110 | Olfactory receptor | 22,33 | 0,019223 | 0 |
| Ch25h | Cholesterol 25-hydroxylase | 18,26 | 0,001887 | 11 |
| Lilrb4 | Leukocyte immunoglobulin-like receptor subfamily B member 4 | 16,57 | 0,000155 | 41 |
| *Gpnmb* | Transmembrane glycoprotein NMB | 16,52 | 0,001199 | *17* |
| *Cst7* | Cystatin-F | 14,16 | 0,009823 | *19* |
| Olfr111 | Olfactory receptor | 13,3 | 0,00493 | 0 |
| Ctla2b | Protein CTLA-2-beta | 13,2 | 0,017815 | 8 |
| *Cd68* | Macrosialin | 12,81 | 0,00005 | *5* |
| Eif4a2 | Eukaryotic initiation factor 4A-II | 12,41 | 0,02398 | 17 |
| *Trem2* | Triggering receptor exressed on myeloid cells 2 | 7,4 | 0,0064 | *21* |
| *Apoe* | Apolipoprotein E | 1,78 | 0,04 | 6 |

FIG. 9 (Cont.)

SEQUENCE LISTING

```
<160> NUMBER OF SEQ ID NOS: 20

<210> SEQ ID NO 1
<211> LENGTH: 5306
<212> TYPE: DNA
<213> ORGANISM: Artificial Sequence
<220> FEATURE:
<223> OTHER INFORMATION: Flag/EGFP tagged murine Rpl10a construction
      under control of the CD11b promoter, I: Intervening sequence
      (IVS); II: SV40 polyA

<400> SEQUENCE: 1
gggccctcca gggttcaagt gattctgctg cctcagcctc ccaggtggga ttacaggtgc      60
ctgccaccac gcctggctaa ttttttttgtc ttttttagtaa agatgaggtt tcaccatgtt    120
gggcaggctg gtttcaattg ctgacctcaa gtgagccacc ccgcctcagc ctcccaaaat     180
```

```
gctaggatta caggcatgag ccaccgcacc cagccaagtt tgtacatata ttttttgacta    240 cacttcttaa ctattcttag gataaattac tagaagtgaa aattcttggg tgaagagctt    300 gaggcctttta cacacacaca cacacacaca cacaaaaata ggctggatgc agtggctcac    360
acctgtaatc tcagcagttt gggaggctga ggaaggagga tcacttgagt ccaggaggtt    420
gagaatagcc tgaacaacat agcaagatct tgtctctaca aaaaatttaa aaaaaattag    480
ctggccatgg cagcatgtgc ctgtagtacc agctactcgg aaggctgagg taggaggatc    540
gcttgagccc aggaggttga ttgaagctgc agtgagctgt gattacacca ctgcactcca    600
gcctgggcaa cagagctaga ctctgtctct aaaaaaagca caaataata tttaaaaagc    660 accaggtatg cctgtacttg agttgtcttt gttgatggct acaaatgagg acagctctgg    720
ctgaagggcg cttccatttc catgggctga aggagggaca ttttgcaaag tgtgttttca    780
ggaagacaca gagttttacc tcctacactt gtttgatctg tattaatgtt tgcttattta    840
tttatttaat tttttttttg agacagagtc tcactctgtc acctgggctg gagtgcagtg    900
gcattattga ggctcattgc agtctcagac tcctgagctc aaacaatcct cctgcctcag    960
cctctggagt agctaggact acaggcatgt gccaccatgc ctggctaatt ttttaaatgt   1020
atttttttgt agagtcgggg tctccctatg ttgcccaggc tggagtgcag tggtgtgatc   1080
ctagctcact gcagcctgga cctcgggctc aagtaattct cacacctcag cctgtccagt   1140 agcagggggct acaggcgcgc accaccatgc ccagctaatt aaaaatattt ttttgtagag   1200
acagggtctc tctatgttgc ccaggctggt ttcaaactcc caggctcaag caatcctcct   1260
gccttggcct cccaaagtgc tggcattaca ggcgtgagcc actgcgcctg cccgtatta   1320 atgtttagaa cacgaattcc aggaggcagg ctaagtctgt tcagcttgtt catatgcttg   1380
ggccaaccca agaaacaagt gggtgacaaa tggcacctttt tggatagtgg tattgacttt   1440
gaaagtttgg gtcaggaagc tggggaggaa gggtgggcag gctgtgggca gtcctgggcg   1500
gaagaccagg cagggctatg tgctcactga gcctccgccc tcttcctttg aatctctgat   1560
agacttctgc ctcctacttc tccttttctg cccttctttg ctttggtggc ttccttgtgg   1620
ttcctcagtg gtgcctgcaa cccctggttc acctccttcc aggttctggc tccttccagc   1680
cgtcgacggt atcgataagc ttgatatcta agtatcaagg ttacaagaca ggtttaagga   1740
gaccaataga aactgggctt gtcgagacag agaagactct tgcgtttctg ataggcacct   1800
attggtctta ctgacatcca ctttctttct ctccacagga attccctgca ggaggcagca   1860
tggactacaa agacgacgac gacaaggtga gcaagggcga ggagctgttc accggggtgg   1920
tgcccatcct ggtcgagctg gacggcgacg taaacggcca agttcagc gtgtccggcg   1980 agggcgaggg cgatgccacc tacggcaagc tgaccctgaa gttcatctgc accaccggca   2040
agctgcccgt gccctggccc accctcgtga ccaccctgac ctacggcgtg cagtgcttca   2100
gccgctaccc cgaccacatg aagcagcacg acttcttcaa gtccgccatg cccgaaggct   2160
acgtccagga gcgcaccatc ttcttcaagg acgacggcaa ctacaagacc cgcgccgagg   2220
tgaagttcga gggcgacacc ctggtgaacc gcatcgagct gaagggcatc gacttcaagg   2280
aggacggcaa catcctgggg cacaagctgg agtacaacta caacagccac aacgtctata   2340
tcatggccga caagcagaag aacggcatca aggtgaactt caagatccgc cacaacatcg   2400
aggacggcag cgtgcagctc gccgaccact accagcagaa cacccccatc ggcgacggcc   2460
ccgtgctgct gcccgacaac cactacctga gcacccagtc cgccctgagc aaagacccca   2520
acgagaagcg cgatcacatg gtcctgctgg agttcgtgac cgccgccggg atcactctcg   2580
```

```
gcatggacga gctgtacaag taaggatccc ggccgcaaac tgcagcgcct ctccggcttg    2640
gctgagcgcg gaacgtgccc gtaacgggca actctcgcga gaacgcgggc tctatttgag    2700
cgcatgcgca aagcgctctg ccttctttcc ggtttccgcg gcagccgcag ccatgaggta    2760
agttgttatc gtggcgctat ccgccgccat ccgtgcaccc acacgcccgc ggacgccccg    2820
cggcccgtct cggaggctct cccggcgact gccccgcgtc gcgagccttt ccccagcgtg    2880
ccgtgggcct gtcatcgggc ccggggtgca gcatggccgg ccccgaacgc cttcgcttct    2940
ccccaacagc agcaaagtct cacgcgacac cctgtacgag gcggtgcggg aagtcctgca    3000
cgggaaccag cgcaagcgcc gcaagtgagc gcgggcctcc ctcccggggc agggcgagca    3060
tccccggcca tggcgaccct ggctcacagc tcccctctcg ctcaggtttc tggagacggt    3120
ggagctgcag atcagcctga agaactacga ccctcagaag acaaacgtt tctcgggcac    3180 cgtcaggttg gcaccgctct aaccccaccc agccctcagt gttcccgtgt ggcctggccg    3240
cgccctaggc gggcacgggg acactgacgt gccagggtag ttcaggagcc ctgctgcagg    3300
caggcaggct ggacggaccc ccaccctggg tcttaaaaca agaggggagg cgtggggagg    3360
cctcggccga gcccgccgcc tagcctgaga agccaggcta gtgttgccca gagctccggg    3420
taaggcttgc cgctccctgc catgcgttca gatctagcgg gatggccagc gccgaccatg    3480
acctgttctg ttttctcccc tcccaaacgc aggctcaagt ccaccccacg ccccaagttc    3540
tcggtgtgcg ttctggggga ccagcagcac tgtgatgaag ccaaggccgt ggatatcccc    3600
cacatggaca tcgaggcgct caagaagctt aacaaaaaca agaagttggt caagaagctg    3660
ggtaggtggg gctcactagg gctgaacaca acccatgacc cctgcccag gagtggcagc    3720 acacattggg cttcacaacc agttagaaaa tgccccacag gctggtctga tactcccctc    3780
tcgccagtgt gtgcagttga ctcatagcca gctattggtt tgggtttcaa gtcttttcag    3840
ttaacaacct atcgagggag gggtcacaag tgtctcccac gtgttagcct ccatggtagc    3900
ccctgtctcc gcatacattt tgggaatagt tatccactgt gagctaggca gttgtcatgc    3960
ctgcttttat agatagaagg tttctccatc tgtcttaaga tttggagtaa tactgagtct    4020
tactgatgtt gccagcctgg ggtctaaggt tatcctctag aagtgctcag gactgtgccc    4080
tgtcactgag ctgtgttctc aggtgacatt atggttccca ggcctgcttg aggcttctca    4140
gatagctggc cttggtccac cttgacaga taatgagaca gctttttct taagatttta    4200 ttttatgtat atgagcaggc tgatgagagc ctcagatccc attacaggtg gctgtgagcc    4260
accatgtggc tgctggaaat tgaactcagg acctctggaa ggcagcactc ttaactgctg    4320
agccatctct ccagtccata gtttgaggca atttaaatgc aggcttacag tgaatccaag    4380 gggtggggc catcacagcc cctcagttct atgcagcaca ccagggattg tgggacatcc    4440
tggtctaaga cctctgtgag gacttgaggg tggagctact cagcagtcat gggtctgagg    4500
aggcaacttg gccttctcgt tgtaaaggat gggttggttg tttaaaatgt tttgttttgt    4560
tttttttttt ttttggtggt ttttgtttgt ttggttggtt ttttggtttt ttttggtttt    4620
tttttttttt tttggctcaa tcctgagtgt ctgtgtcttc tagctaagaa gtacgatgcc    4680
tttttggcct ctgagtctct gattaagcag atcccacgta tcctgggccc aggcctaaac    4740
aaggctggca agttcccctc cctgctgaca cacaatgaaa acatggtggc caaagtggat    4800
gaggtgaaat cgacaatcaa gttccagatg aagaaggtca gtctgggcgg tgtgtggtgg    4860
ggaaaccaga aagagctagg tctgggtgcc ttagccctgg gttaagcctt ttcactgggg    4920
```

```
gaaagggtac atgctagctt agcctggtga ccttttctgt ccatgcaggt gctgtgtttg    4980
gccgtcgctg ttggccacgt gaagatgacc gatgatgagc tagtctacaa cattcatctg    5040
gctgtcaatt tcttggtgtc cttgcttaag aaaaactggc aaaacgtgcg ggctctgtac    5100
atcaagagca ccatgggcaa gccccagcgt ctgtattagg atgctccaat aaacctcact    5160
gctgccactc aggcggccgc accgcggttg atgagtttgg acaaaccaca actagaatgc    5220
agtgaaaaaa atgctttatt tgtgaaattt gtgatgctat tgctttattt gtaaccatta    5280
taagctgcaa taaacaagtt ccgcgg                                          5306

<210> SEQ ID NO 2
<211> LENGTH: 86
<212> TYPE: DNA
<213> ORGANISM: Artificial Sequence
<220> FEATURE:
<223> OTHER INFORMATION: pGL3-promoter- Saa3-3'UTR-wt

<400> SEQUENCE: 2
gttttctctt cctgttgttc ccagtcatgc tgccccccga aagaggagc aactactggg    60 ttgagatatt ttctaaaatc tggatc                                          86

<210> SEQ ID NO 3
<211> LENGTH: 168
<212> TYPE: DNA
<213> ORGANISM: Artificial Sequence
<220> FEATURE:
<223> OTHER INFORMATION: pGL3-promoter-SCRAMBLE

<400> SEQUENCE: 3
ggatatcttt tacccatacg atgttcctga ctatgcgggc tatccctatg acgtcccgga    60
ctatgcagga tcctatccat atgacgttcc agattacgct gctcagatcg ataagcttac    120
catgttccag gcggccgagc gcccccagga gtgggccatg gagggccc                  168

<210> SEQ ID NO 4
<211> LENGTH: 87
<212> TYPE: DNA
<213> ORGANISM: Artificial Sequence
<220> FEATURE:
<223> OTHER INFORMATION: Saa3-3'UTR deletion of segment C

<400> SEQUENCE: 4
gttttctctt cctgttgttc ccagtcatgc tgccccccga aagaggagc aactactggg    60 ttgagatatt ttctaaaatc tggatcc                                         87

<210> SEQ ID NO 5
<211> LENGTH: 45
<212> TYPE: DNA
<213> ORGANISM: Artificial Sequence
<220> FEATURE:
<223> OTHER INFORMATION: Saa3-3'UTR deletion of segment B+C

<400> SEQUENCE: 5
gttttctctt cctgttgttc ccagtcatgc tgccccccgt ctaga                     45

<210> SEQ ID NO 6
<211> LENGTH: 89
<212> TYPE: DNA
<213> ORGANISM: Artificial Sequence
<220> FEATURE:
<223> OTHER INFORMATION: Saa3-3'UTR deletion of segment A

<400> SEQUENCE: 6
```
agaagaggag caactactgg gttgagatat tttctaaaat ctggatccct aaacatccca    60
atgtgctgaa taaatacttg tgaaatgca                                     89

<210> SEQ ID NO 7
<211> LENGTH: 69
<212> TYPE: DNA
<213> ORGANISM: Artificial Sequence
<220> FEATURE:
<223> OTHER INFORMATION: Saa3-3'UTR deletion of segment B

<400> SEQUENCE: 7
gttttctctt cctgttgttc ccagtcatgc tgcccccga atgtgctgaa taaatacttg    60
tgaaatgca                                                            69

<210> SEQ ID NO 8
<211> LENGTH: 19
<212> TYPE: RNA
<213> ORGANISM: Artificial Sequence
<220> FEATURE:
<223> OTHER INFORMATION: siRNA targeting SRSF3 - ON-TARGETplus SMARTpool
      siRNA J-059214-09, Srsf3

<400> SEQUENCE: 8
gaaaggcacc ugagaauau                                                 19

<210> SEQ ID NO 9
<211> LENGTH: 19
<212> TYPE: RNA
<213> ORGANISM: Artificial Sequence
<220> FEATURE:
<223> OTHER INFORMATION: siRNA targeting SRSF3 - ON-TARGETplus SMARTpool
      siRNA J-059214-10, Srsf3

<400> SEQUENCE: 9
ccagaugaga uuuagguau                                                 19

<210> SEQ ID NO 10
<211> LENGTH: 19
<212> TYPE: RNA
<213> ORGANISM: Artificial Sequence
<220> FEATURE:
<223> OTHER INFORMATION: siRNA targeting SRSF3 - ON-TARGETplus SMARTpool
      siRNA J-059214-11, Srsf3

<400> SEQUENCE: 10
cuagcauaau uguguagua                                                 19

<210> SEQ ID NO 11
<211> LENGTH: 19
<212> TYPE: RNA
<213> ORGANISM: Artificial Sequence
<220> FEATURE:
<223> OTHER INFORMATION: siRNA targeting SRSF3 - ON-TARGETplus SMARTpool
      siRNA J-059214-12, Srsf3

<400> SEQUENCE: 11
cuagaagguu ccaacauga                                                 19

<210> SEQ ID NO 12
<211> LENGTH: 164
<212> TYPE: PRT
<213> ORGANISM: Mus musculus

<400> SEQUENCE: 12

```
Met His Arg Asp Ser Cys Pro Leu Asp Cys Lys Val Tyr Val Gly Asn
1               5                   10                  15

Leu Gly Asn Asn Gly Asn Lys Thr Glu Leu Glu Arg Ala Phe Gly Tyr
            20                  25                  30

Tyr Gly Pro Leu Arg Ser Val Trp Val Ala Arg Asn Pro Pro Gly Phe
        35                  40                  45

Ala Phe Val Glu Phe Glu Asp Pro Arg Asp Ala Ala Asp Ala Val Arg
    50                  55                  60

Glu Leu Asp Gly Arg Thr Leu Cys Gly Cys Arg Val Arg Val Glu Leu
65                  70                  75                  80

Ser Asn Gly Glu Lys Arg Ser Arg Asn Arg Gly Pro Pro Ser Trp
                85                  90                  95

Gly Arg Arg Pro Arg Asp Asp Tyr Arg Arg Ser Pro Pro Arg
                100                 105                 110

Arg Arg Ser Pro Arg Arg Arg Ser Phe Ser Arg Ser Arg Ser Arg Ser
    115                 120                 125

Leu Ser Arg Asp Arg Arg Glu Arg Ser Leu Ser Arg Glu Arg Asn
    130                 135                 140

His Lys Pro Ser Arg Ser Phe Ser Arg Ser Arg Ser Arg Ser
145                 150                 155                 160

Asn Glu Arg Lys
```

<210> SEQ ID NO 13
<211> LENGTH: 73
<212> TYPE: PRT
<213> ORGANISM: Mus musculus

<400> SEQUENCE: 13

```
Lys Val Tyr Val Gly Asn Leu Gly Asn Asn Gly Asn Lys Thr Glu Leu
1               5                   10                  15

Glu Arg Ala Phe Gly Tyr Tyr Gly Pro Leu Arg Ser Val Trp Val Ala
            20                  25                  30

Arg Asn Pro Pro Gly Phe Ala Phe Val Glu Phe Glu Asp Pro Arg Asp
        35                  40                  45

Ala Ala Asp Ala Val Arg Glu Leu Asp Gly Arg Thr Leu Cys Gly Cys
    50                  55                  60

Arg Val Arg Val Glu Leu Ser Asn Gly
65                  70
```

<210> SEQ ID NO 14
<211> LENGTH: 79
<212> TYPE: PRT
<213> ORGANISM: Mus musculus

<400> SEQUENCE: 14

```
Arg Ser Arg Asn Arg Gly Pro Pro Ser Trp Gly Arg Arg Pro Arg
1               5                   10                  15

Asp Asp Tyr Arg Arg Ser Pro Pro Arg Arg Ser Pro Arg
            20                  25                  30

Arg Arg Ser Phe Ser Arg Ser Arg Ser Arg Ser Leu Ser Arg Asp Arg
    35                  40                  45

Arg Arg Glu Arg Ser Leu Ser Arg Glu Arg Asn His Lys Pro Ser Arg
    50                  55                  60

Ser Phe Ser Arg Ser Arg Ser Arg Ser Asn Glu Arg Lys
65                  70                  75
```

<210> SEQ ID NO 15
<211> LENGTH: 25
<212> TYPE: DNA
<213> ORGANISM: Artificial Sequence
<220> FEATURE:
<223> OTHER INFORMATION: Antisense

<400> SEQUENCE: 15
ccaagggaca ggaatcacga tgcat                                           25

<210> SEQ ID NO 16
<211> LENGTH: 84
<212> TYPE: DNA
<213> ORGANISM: Mus musculus

<400> SEQUENCE: 16
ggtgggcctg tcggagcgtt aggatttgag cttgggcctt ttgaacccag gatctcgaaa     60
tgcatcgtga ttcctgtccc ttgg                                            84

<210> SEQ ID NO 17
<211> LENGTH: 25
<212> TYPE: DNA
<213> ORGANISM: Artificial Sequence
<220> FEATURE:
<223> OTHER INFORMATION: Antisense

<400> SEQUENCE: 17
ccaatggaca ggaatcacga tgcat                                           25

<210> SEQ ID NO 18
<211> LENGTH: 56
<212> TYPE: DNA
<213> ORGANISM: Homo sapiens

<400> SEQUENCE: 18
gccgccgcat tttttaaccc tagatctcga aatgcatcgt gattcctgtc cattgg         56

<210> SEQ ID NO 19
<211> LENGTH: 720
<212> TYPE: DNA
<213> ORGANISM: Homo sapiens

<400> SEQUENCE: 19
tttccaggtc acctgaccgg tctcctttgc tgtcggcgcc aagtcctgca agtttgcttg     60
agagacgaga aaccagcaag agttgggcaa actttccaaa ccaggctttt ccttcagtgt    120
ggaatctagg cggccacagt ctggtgccag ctgggtcaca aacagctccg tgacctgttt    180
gtaaacgcga tgctcttagt tccagactaa ccgctcacaa gggtgaagca cttaattaat    240
tcatctctta atcttgttag gggccaacgg ctcctattag tgtttgagcg tgacggcgac    300
ggtgctgttt atgaagccct agcctatttg gaggtgagga agaggagtct gtgggtaacc    360
tggaggtcga cagaccggga ggaacgctcg agggagcacc aggcctgtta caacgagcgc    420
gcgccgacgc acgtctccac ccacccggcg caaccgccag agcgcgctcc cagcaaccgc    480
ggctctcgct gcgtttgtag ccatacgtca cggcctcttc tgcttctcat tggggagcc    540 cgtccaatca tgtgattcca gtatggcgta taaataaagg cgaggagaag gcggtggtcc    600
gccatttcgt ggacgccggg tgagtgagag agttggttgg tgttgggccg gaggaaagcg    660
ggaagactca tcggagcgtg tggatttgag ccgccgcatt ttttaaccct agatctcgaa    720

<210> SEQ ID NO 20

```
<211> LENGTH: 22
<212> TYPE: PRT
<213> ORGANISM: Artificial Sequence
<220> FEATURE:
<223> OTHER INFORMATION: Fragment

<400> SEQUENCE: 20

Gly Asn Asn Gly Asn Lys Thr Glu Leu Glu Arg Ala Phe Gly Tyr Tyr
1               5                   10                  15

Gly Pro Leu Arg Ser Val
            20
```

USE OF SRSF3 AGENTS FOR THE TREATMENT AND/OR PREVENTION OF NEUROLOGICAL CONDITIONS, CANCER, BACTERIAL INFECTIONS OR VIRAL INFECTIONS

RELATED APPLICATIONS

This application is a 371 of International Application Serial No. PCT/CA2018/051452, filed on Nov. 15, 2018, which claims priority from U.S. Provisional Patent Application Ser. No. 62/586,567, filed on Nov. 15, 2017, the disclosure of which application is herein incorporated by reference in its entirety. This application claims priority from U.S. provisional application 62/586,567 filed Nov. 15, 2017.

TECHNICAL FIELD

The present invention relates to methods for the treatment, prognostic and diagnostic of neurological conditions, cancer or viral infections, kits related to such methods and methods to identify candidate compounds for preventing and treating neurological conditions, cancer or viral infections.

BACKGROUND

Microglia are the principal immune cells of the brain. Under physiological conditions microglial cells are essential for maintenance of the brain tissue homeostasis (Tremblay et al., 2011), however, in the context of disease and/or injury it is becoming increasingly clear that microglial cells have pivotal role in initiation and regulation of inflammatory responses in the brain (Hanisch and Kettenmann, 2007). The consensus today is that once activated, microglia can acquire a wide repertoire of immune profiles ranging from the classical pro-inflammatory to alternative, anti-inflammatory polarization phenotypes (David and Kroner, 2011; Kierdorf and Prinz, 2013; Ransohoff and Brown, 2012). Over the past decade, it was shown that optimal and timely activation of microglial cells is instrumental in the control of the inflammation-induced damage to the central nervous system (CNS) (Chen and Trapp, 2016; Gravel et al., 2016; Lalancette-Hebert et al., 2007; Lalancette-Hebert et al., 2009; Schwartz and Shechter, 2010). However, at present, the molecular mechanisms involved in the control of microglia polarization profiles remain elusive.

SUMMARY

The present description relates to the use of a SRSF3 agent for regulating the innate immune function of a myeloid cell, wherein the SRSF3 agent inhibits expression or function of SRSF3 or a fragment thereof.

The present description relates to the use of a SRSF3 agent for:
- the treatment and/or prevention of a neurological condition (e.g. vascular dementia, frontotemporal lobar degeneration (FTD), Alzheimer, motor neuron disease (e.g. Amyotrophic Lateral Sclerosis (ALS) including sporadic or familial ALS, Progressive bulbar palsy (PBP), Primary lateral sclerosis (PLS) or Kennedy's Disease) or Parkinson's disease);
- inhibiting the proliferation of a cancer of the central nervous system (e.g. glial tumor); or
- the treatment and/or prevention of a viral or bacterial infection (e.g. HIV);

in a patient in need thereof, wherein the SRSF3 agent inhibits expression or function of SRSF3 or a fragment thereof.

The present description relates to a method for:
- the treatment and/or prevention of a neurological condition (e.g. vascular dementia, frontotemporal lobar degeneration (FTD), Alzheimer, motor neuron disease (e.g. Amyotrophic Lateral Sclerosis (ALS) including sporadic or familial ALS, Progressive bulbar palsy (PBP), Primary lateral sclerosis (PLS) or Kennedy's Disease) or Parkinson's disease);
- inhibiting the proliferation of a cancer of the central nervous system (e.g. glial tumor); or
- the treatment and/or prevention of a viral or bacterial infection (e.g. HIV);

comprising administering an effective amount (e.g. a therapeutically effective amount) of at least one SRSF3 agent for in a patient in need thereof, wherein the SRSF3 agent inhibits expression or function of SRSF3 or a fragment thereof.

The present description relates to a method for the diagnostic and treatment of a subject predisposed or suspected of developing a neurological condition, a cancer of the central nervous system, a bacterial infection or a viral infection, or suffering from a neurological condition, a cancer of the central nervous system, a bacterial infection or a viral infection, the method comprising the step of:
- determining the level of SRSF3 or a fragment thereof in a biological sample of the subject;
- and
- administering an effective amount (e.g. a therapeutically effective amount) of at least one SRSF3 agent to the subject;

wherein observing an elevated level of SRSF3 or fragment thereof in the biological sample relative to a reference level of SRSF3 or fragment thereof, indicates that the subject is predisposed or suspected of a neurological condition, a cancer of the central nervous system, a bacterial infection or a viral infection or is suffering from a neurological condition, a cancer of the central nervous system, a bacterial infection or a viral infection.

The present description relates to a method for the diagnostic of a subject predisposed or suspected of developing a neurological condition, a cancer of the central nervous system, a bacterial infection or a viral infection, or suffering from a neurological condition, a cancer of the central nervous system, a bacterial infection or a viral infection, the method comprising the step of:
- determining the level of SRSF3 or a fragment thereof in a biological sample of the subject wherein observing an elevated level of SRSF3 or fragment thereof in the biological sample relative to a reference level of SRSF3 or fragment thereof, indicates that the subject is predisposed or suspected of a neurological condition, a cancer of the central nervous system, a bacterial infection or a viral infection or is suffering from a neurological condition, a cancer of the central nervous system, a bacterial infection or a viral infection.

The present description relates to a method for the diagnostic of a subject predisposed or suspected of developing a neurological condition, a cancer of the central nervous system, a bacterial infection or a viral infection, or suffering from a neurological condition, a cancer of the central nervous system, a bacterial infection or a viral infection, the method comprising the step of:
- identifying a profile of upregulated and untranslated mRNA in a biological sample of the subject, wherein observing a profile of upregulated and untranslated mRNA coding for a polypeptide implicated in an innate immune response of a microglial cell, indicates that that the subject is predisposed or suspected of a neurological condition, a cancer of the central nervous system, a bacterial infection or a viral infection or is suffering from a neurological condition, a cancer of the central nervous system, a bacterial infection or a viral infection.

The present description relates to a method for the diagnostic and treatment of a subject predisposed or suspected of developing a neurological condition, a cancer of the central nervous system, a bacterial infection or a viral infection, or suffering from a neurological condition, a cancer of the central nervous system, a bacterial infection or a viral infection, the method comprising the step of:
  identifying a profile of upregulated and untranslated mRNA in a biological sample of the subject,
  administering an effective amount (e.g. a therapeutically effective amount) of at least one SRSF3 agent to the subject;
  wherein observing a profile of upregulated and untranslated mRNA coding for a polypeptide implicated in an innate immune response of a microglial cell, indicates that that the subject is predisposed or suspected of a neurological condition, a cancer of the central nervous system, a bacterial infection or a viral infection or is suffering from a neurological condition, a cancer of the central nervous system, a bacterial infection or a viral infection.

The present description relates to a method for identifying a candidate compound useful in the treatment and/or prevention of a neurological condition, a cancer of the central nervous system, a bacterial infection or a viral infection, the method comprising the steps of:
  a) contacting the candidate compound with a biological system comprising SRSF3 or fragment thereof,
  b) measuring the ability of the candidate compound to inhibit SRSF3 expression of function,
  c) determining if the candidate compound is useful in the treatment and/or prevention of a neurological condition, a cancer of the central nervous system, a bacterial infection or a viral infection based on the result of step b).

The present description relates to a method for identifying a candidate compound useful in the treatment and/or prevention of a neurological condition, a cancer of the central nervous system, a bacterial infection or a viral infection, the method comprising the steps of:
  a) contacting the candidate compound with a biological system comprising SRSF3 or fragment thereof and at least one 3'UTR of a mRNA coding for a polypeptide implicated in an innate immune response of a microglial cell comprising at least of SRSF3 binding site,
  b) measuring the ability of the candidate compound to inhibit the binding between SRSF3 or a fragment thereof and at least one 3'UTR SRSF3 binding site of the mRNA,
  c) determining if the candidate compound is useful in the treatment and/or prevention of a neurological condition, a cancer of the central nervous system, a bacterial infection or a viral infection based on the result of step b).

The present description relates to a method for monitoring the progression or the regression of a neurological condition, a cancer of the central nervous system, a bacterial infection or a viral infection in a subject, the method comprising the step of:
  determining the level of SRSF3 or fragment thereof in a biological sample of the subject,
  wherein observing an increased level of SRSF3 or fragment thereof indicates a progression of the neurological condition and wherein observing a decreased level of SRSF3 thereof indicates a regression of the neurological condition, the cancer of the central nervous system, the bacterial infection or the viral infection.

The present description relates to the use of the level of SRSF3 or fragment thereof in a biological sample as a biochemical marker for monitoring the progression or the regression of a neurological condition, a cancer of the central nervous system, a bacterial infection or a viral infection in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The sequence of the anti-human SRSF3 morpholinos is: 5'-CCAATGGACAGGAATCACGATGCAT-3'(SEQ ID NO: 17). Brackets have been inserted around the mRNA target to illustrate its position in the human sequence of SRSF3[shown below]. Note that the brackets are laced on a sense strand.

(SEQ ID NO: 18)
5'-gccgccgcattttttaaccctagatctcgaa[(atg)catcgtga ttcctgtccattgg]-3'.

Figure 13:
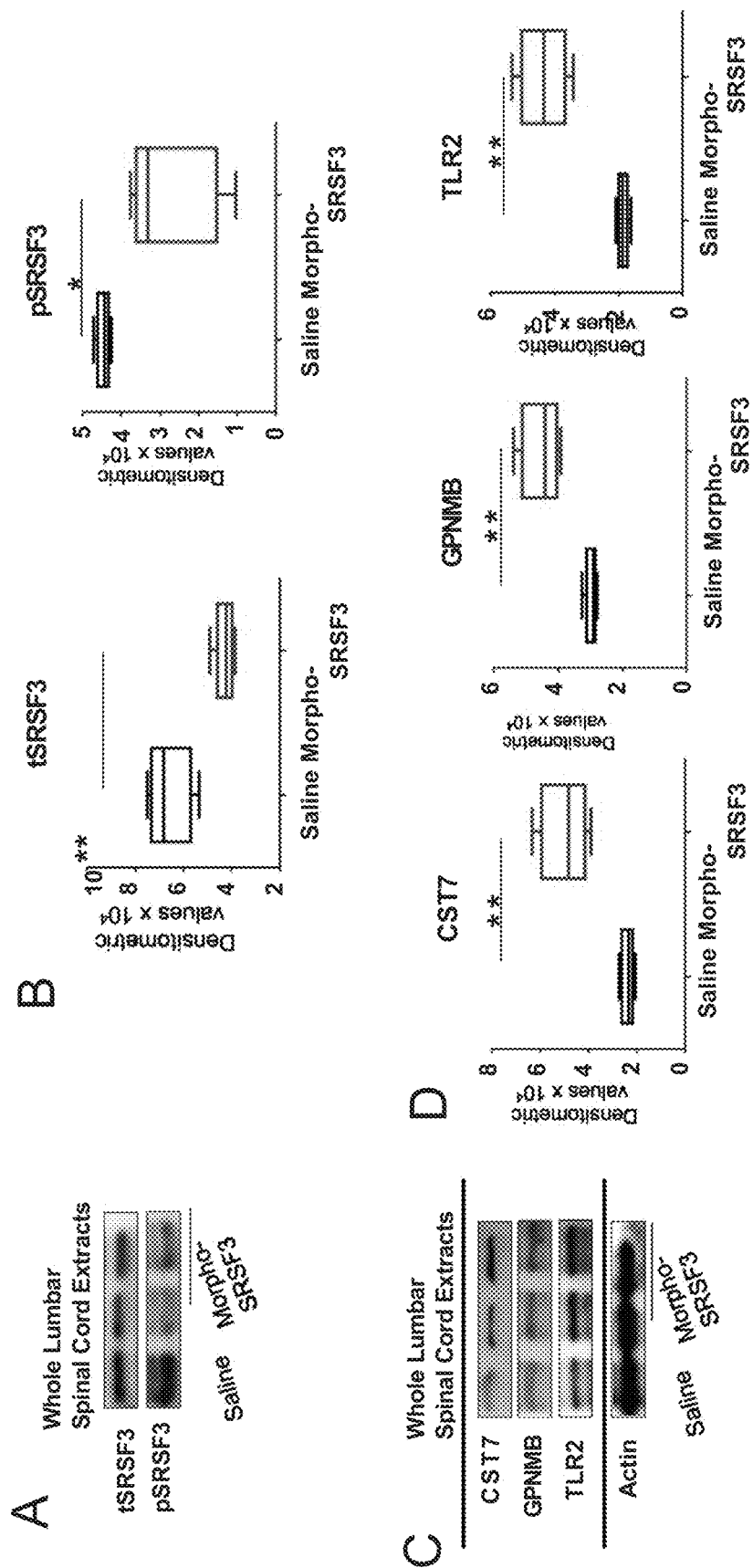

FIG. 13 De novo synthesis of the proteins after knockdown of SRSF3. (A) Western blot analysis of whole lumbar spinal cord homogenates from SOD1G93A transgenic mice after intrathecal delivery of 50 μg of anti-SRSF3 morpholinos or saline. (B) Quantitative analysis of western blot showed the expression level of endogenous total SRSF3 (tSRSF3) and phospho-SRSF3 (pSRSF3) after anti-SRSF3 morpholinos administration. Data are mean±SEM (n=3; tSRSF3: Saline vs anti-SRSF3 morpholinos, **p<0.01; pSRSF3: Saline vs anti-SRSF3 morpholinos, *p<0.05). (C) Western blot analysis of whole lumbar spinal cord extracts after intrathecal delivery of 50 ug of anti-SRSF3 morpholinos or Saline in SOD1G93A mice. (D) Quantitative analysis of western blot showed the increase of the expression level of endogenous CST7, GPNMB and TLR2 proteins after the knockdown of SRSF3. Data represent mean±SEM (n=3; **p<0.01). Actin is used as loading control.

Figure 14:
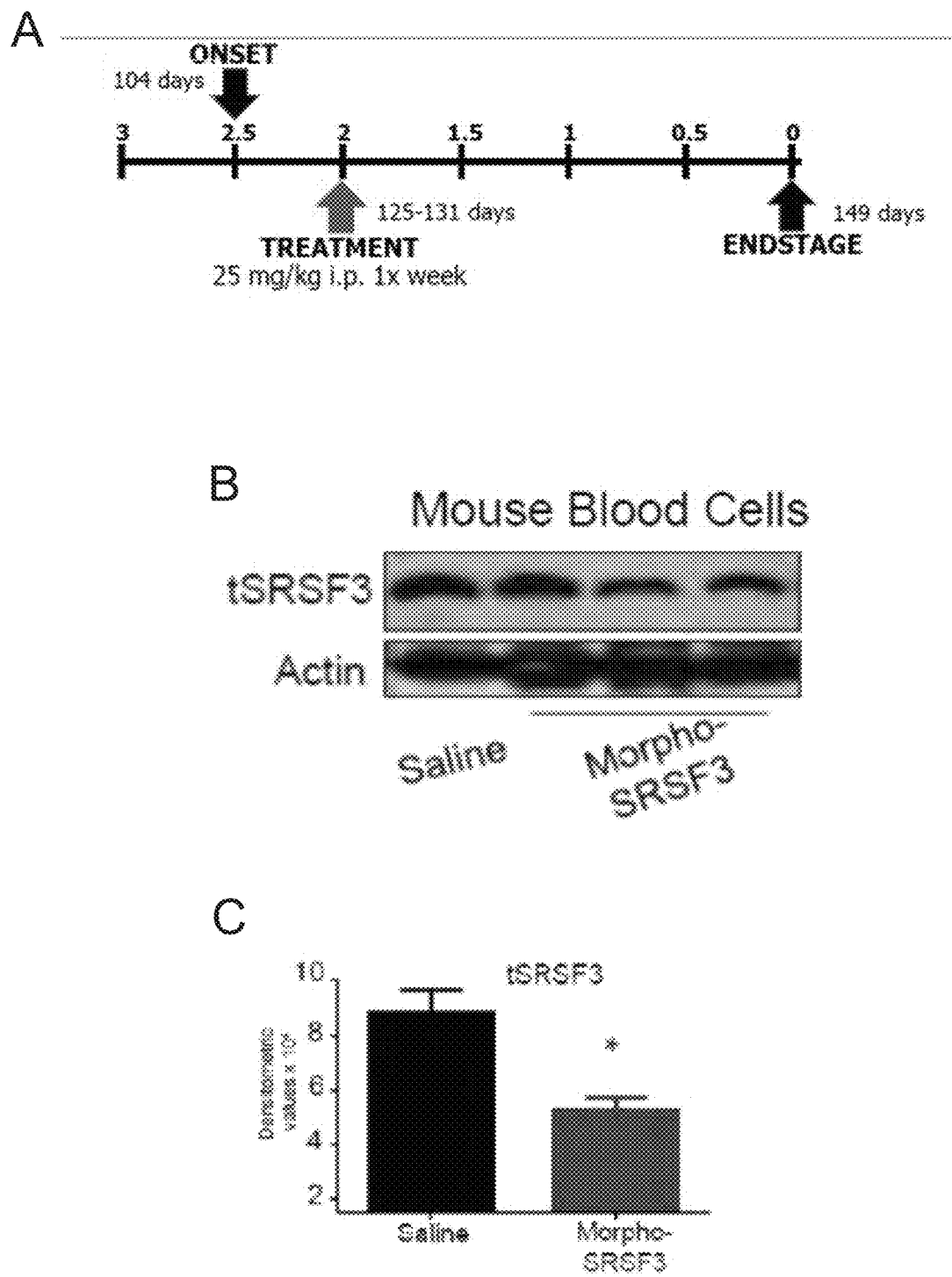
Figure 14:
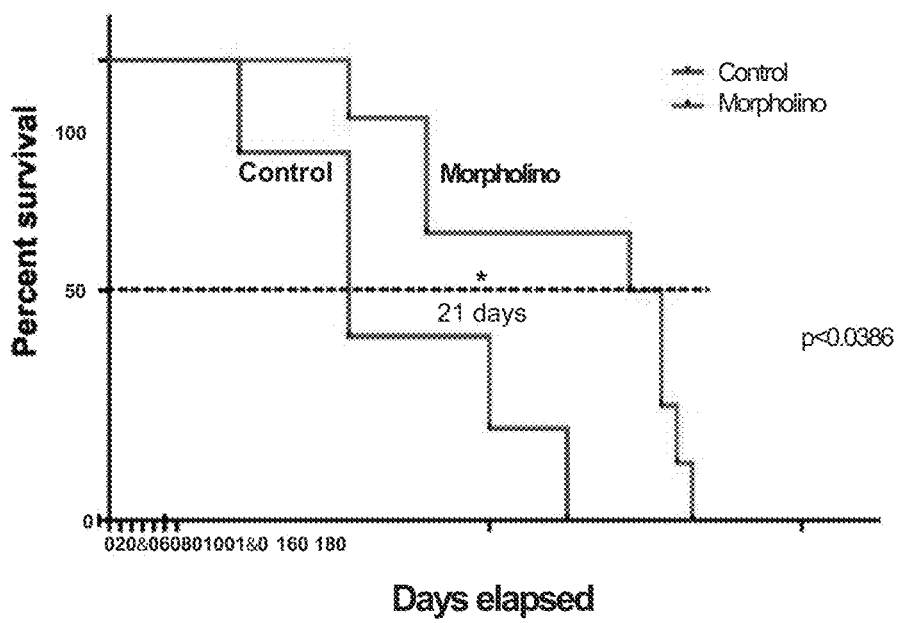
Figure 14:
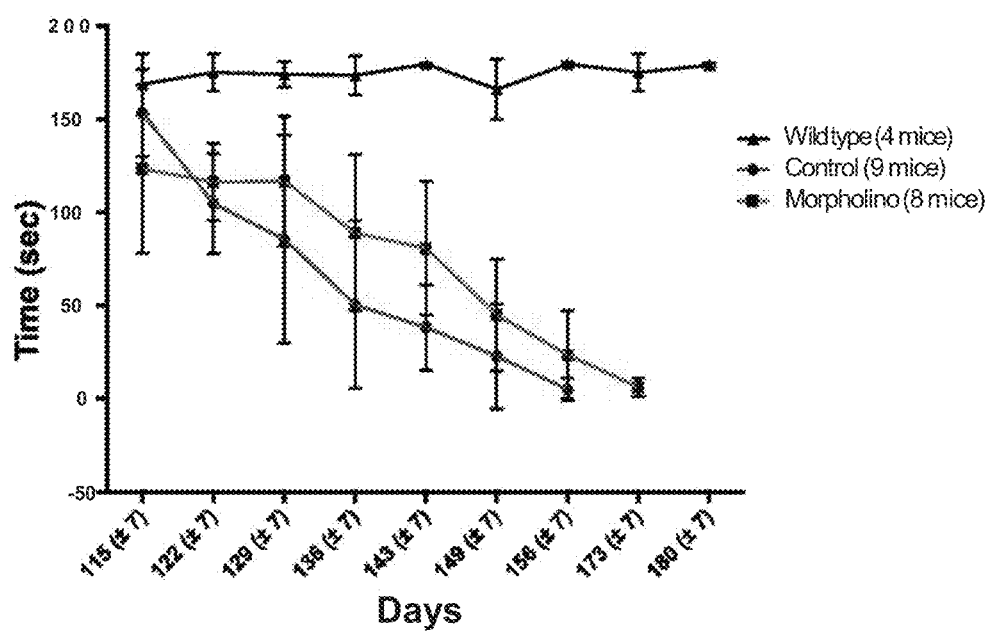

FIG. 14 Anti-SRSF3 morpholino treatment initiated after paralysis onset increased survival of SOD1G93A transgenic mice and improved their motor Function. (A) Schematic representation of the experiment timeline. (B) Western blot analysis of purified mouse blood cells with Ficoll after i.p. injection of anti-SRSF3 morpholinos or Saline. (C) Quantitative analysis of western blot showed the decrease of the expression level of endogenous SRSF3 six days post morpholino administration. (Data are mean±SEM, n=3; *p<0.05) Actin is used as a loading control. (D) Kaplan-Meier survival curves from anti-SRSF3 morphlinos- or control-treated SOD1$^{G93A}$ transgenic mice. SOD1$^{G93A}$ transgenic mice were treated intraperitoneal with anti-SRSF3 morpholinos (25 mg/kg once per week, n=8, red line) or with control morpholinos (scramble, n=9, blue line). There was a statistically significant difference in the probability of survival for morpholinos-treated group when compared with control-treated group according to the log-rank test of the Kaplan-Meier analysis (p<0.0386 for morpholinos). (E) Rotarod assessment of motor function was performed throughout treatment in transgenic SOD1$^{G93A}$ mice injected intraperitoneally with morpholinos (25 mg/kg once per week; data represent mean±SEM, n=8, red line) or with control morpholinos (scramble, 25 mg/kg once per week; data represent mean±SEM, n=9, blue line). Wild type mice (WT) were not treated and used as control (Data represent mean±SEM, n=4, black line).

Figure 15:
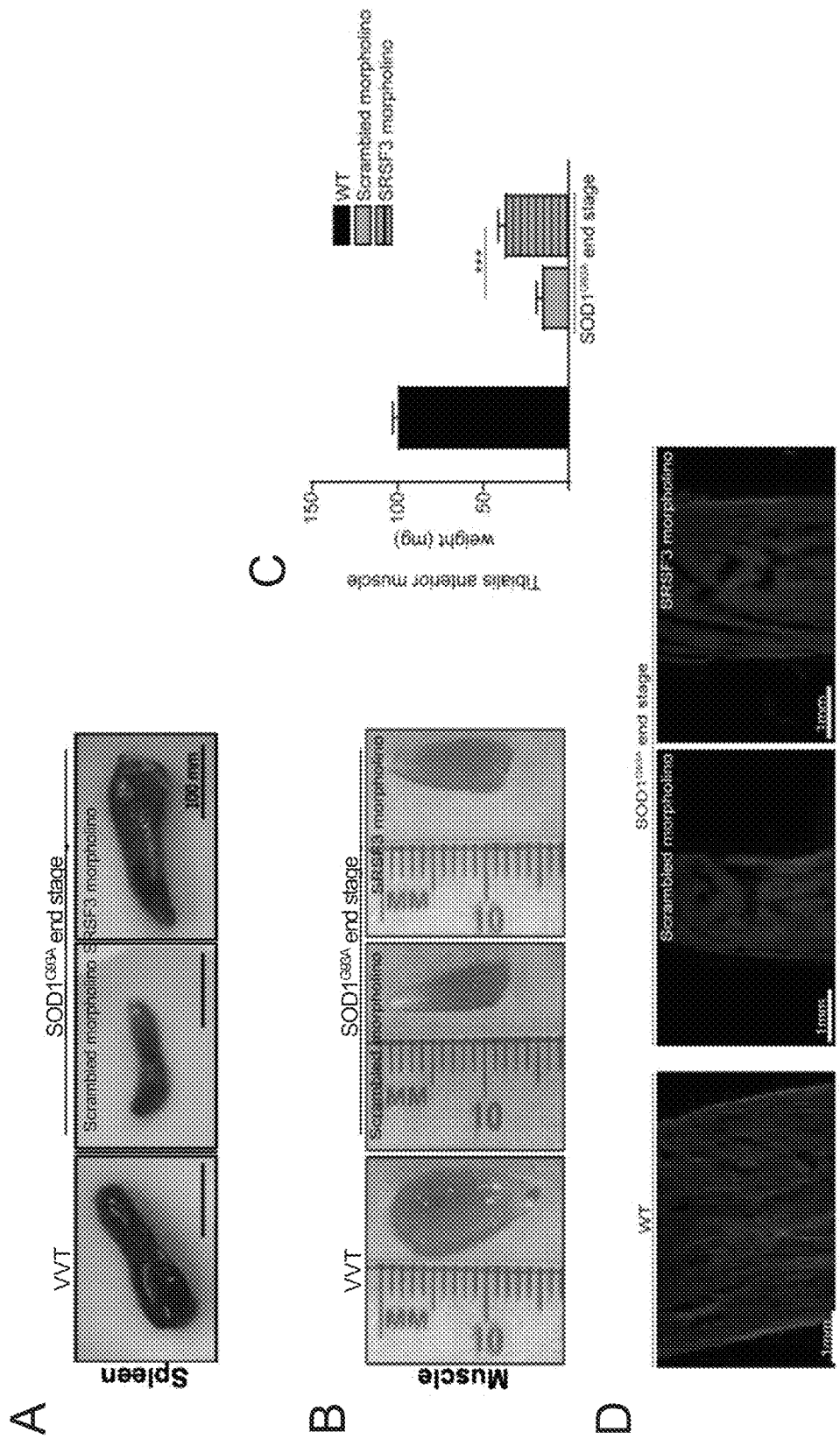

FIG. 15 Treatment with anti-SRSF3 morpholinos reverses spleen and muscle atrophy in SOD1$^{G93A}$ mice. (A) Morphology and size of spleens from SOD1$^{G93A}$Tg mice and WT littermates. Intraperitoneal treatment with anti-SRSF3 morpholinos initiated in symptomatic SOD1$^{G93A}$ transgenic mice (25 mg/kg once per week) reverses spleen atrophy when compared to controls (scramble, 25 mg/kg once per week). (B) Morphology and size of the muscle from SOD1$^{G93A}$ Tg mice and WT littermates. Intraperitoneal treatment with anti-SRSF3 morpholinos treatment initiated in symptomatic SOD1$^{G93A}$ mice (25 mg/kg once per week) reversed muscle atrophy when compared to the control (scramble, 25 mg/kg once per week). (C) Mean Tibialis anterior (TA) muscle weights were compared between SOD1$^{G93A}$ treated with anti-SRSF3 morpholinos or scrambled morpholinos. Wild type mice (WT) were used as control. (Data represent mean±SEM, n=3 mice/group, ***p<0.001) (D) Representative photomicrographs of NFH-stained TA muscle (green). Scale bar 1 mm.

Figure 16:
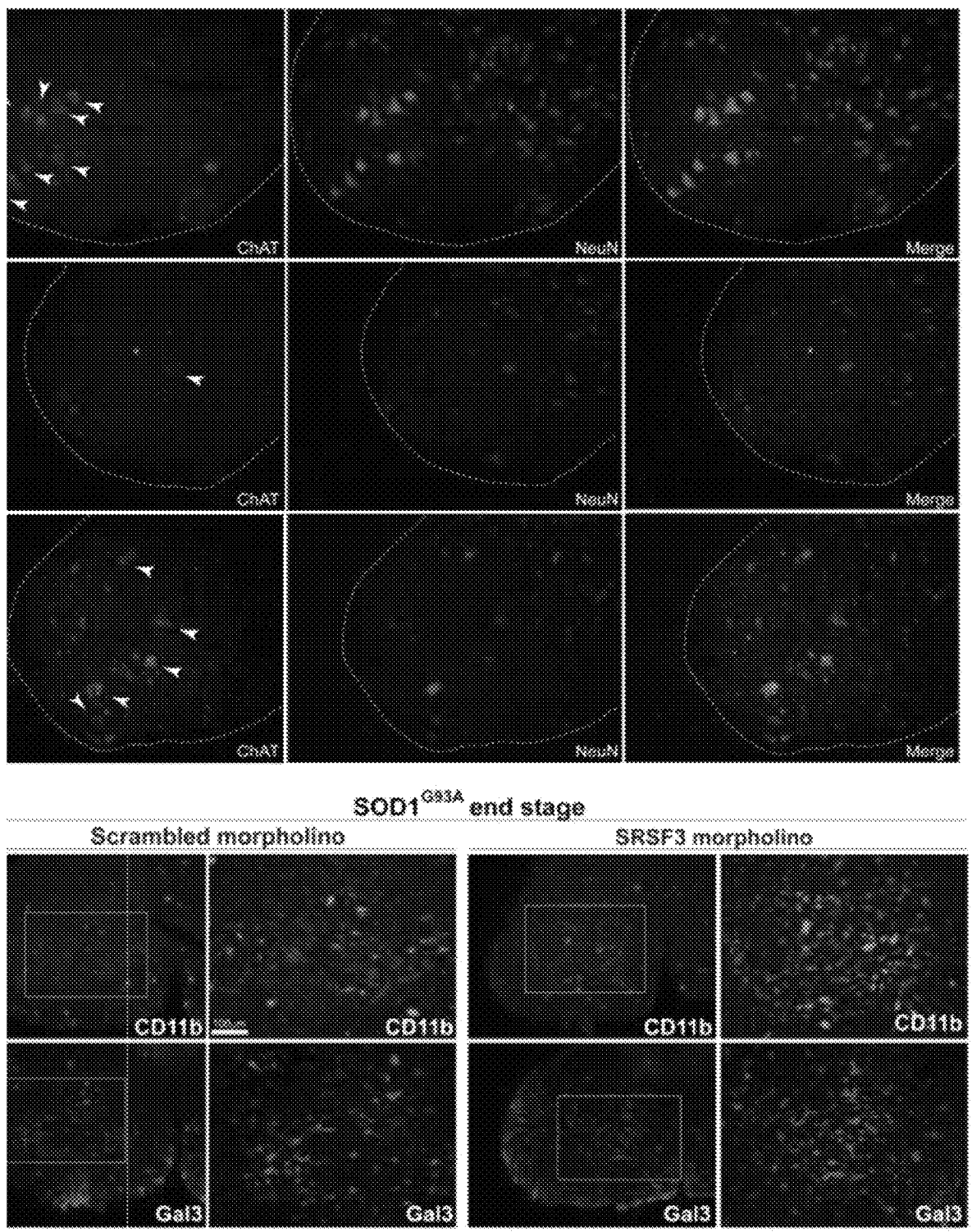

FIG. 16 Treatment with anti-SRSF3 morpholinos preserves motor neurons and increases microglial activation in the spinal cord of SOD1$^{G93A}$ mice. (A) Representative photomicrographs of ChAT and NeuN-stained lumbar spinal cord sections from late symptomatic SOD1$^{G93A}$ transgenic mice injected with anti-SRSF3 morpholinos or scramble. Wild type (WT) mice were used as control (n=3 per group). (B) Representative photomicrographs of Iba1-stained lumbar spinal cord sections from late symptomatic SOD1$^{G93A}$ transgenic mice injected with anti-SRSF3 morpholinos or Saline. Wild type (WT) mice were used as control (n=3 per group).

Figure 4:
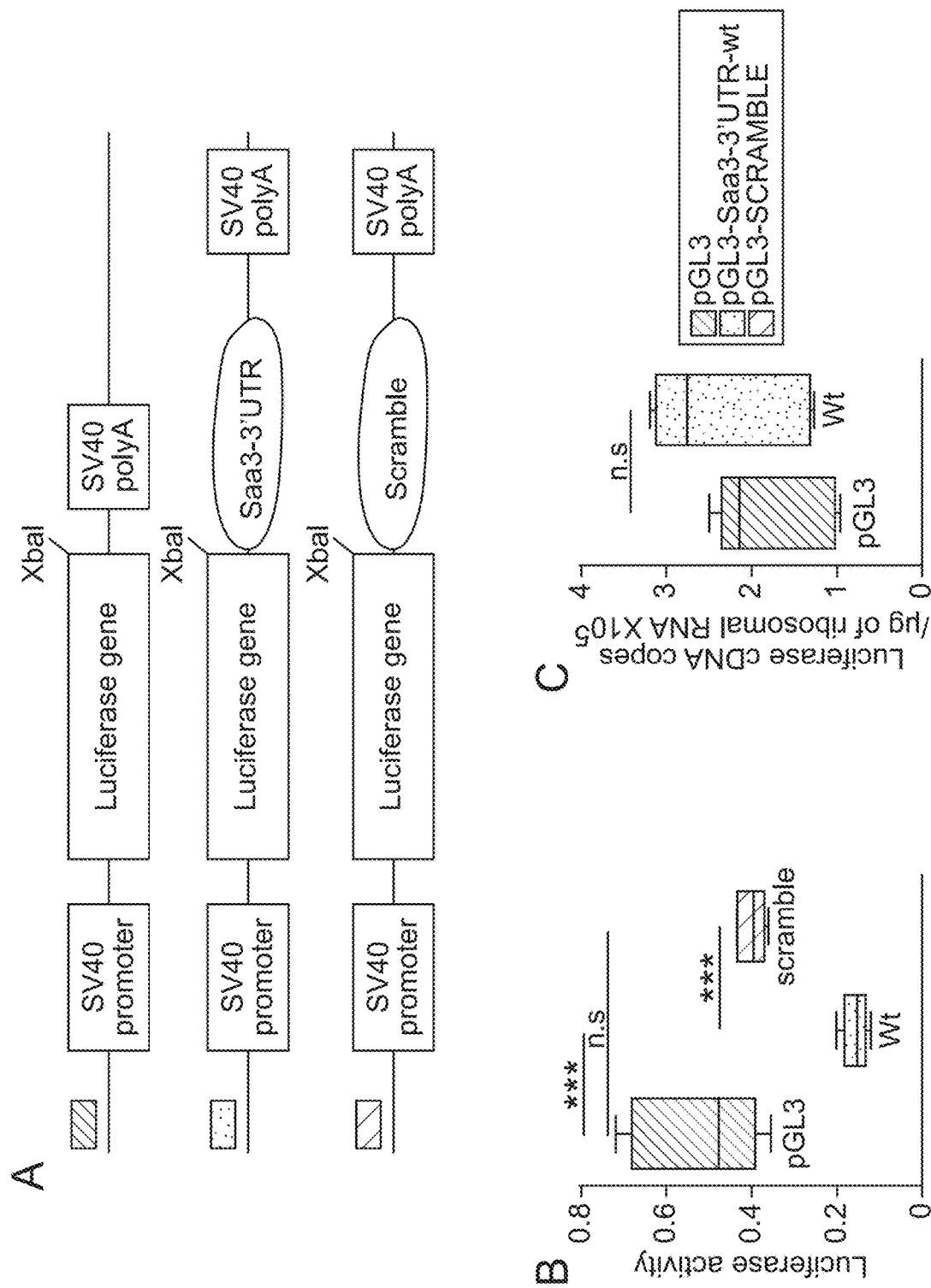
FIG. 4 Inhibition of Luciferase Reporter Gene Activity by Saa3-3'UTR. (A) Schematic representation of pGL3-promoter (pGL3) (GenBank Accession Number U47298), pGL3-promoter-Saa3-3'UTR-wt (SEQ ID NO:2) (pGL3-Saa3-3'UTR) and pGL3-promoter-SCRAMBLE (SEQ ID NO:3) (pGL3-SCRAMBLE) used for luciferase assay. Firefly luciferase reporter gene (brown box), Saa3-3'UTR sequence (orange circle) and SV40 poly A region (light gray box) are shown. (B) HEK 293 cells were transfected with each construct and assayed for luciferase activity after 48 hours. Data represent mean±SEM of three independent experiments conducted in triplicate (n.s.: p>0.05; ***p<0.001). (C) Relative firefly luciferase mRNA level measured by RT-qPCR of BV2 cells stably expressing F/EGFP-Rpl10a plasmid transfected with pGL3 vector or the pGL3-Saa3-3'UTR-wt vector. The ribosome-associated mRNA was extracted using TRAP protocol 48 hours after the transfection. Data are representative of three individual experiments each one conducted in technical duplicates (n=6; mean±SEM; n.s.: p=0.5676). (D) Putative RNA binding proteins (RBPs) position along the Saa3-3'UTR segments according to RBP map with a high stringency level. Each circle represented one RBP binding site. RBPs identified by mass spectrometer analysis after LPS injection are framed in blue. (E) Schematic representations of the Saa3-3'UTR deletions (SEQ ID NOS: 4 to 7). Saa3-3'UTR was divided in three segments: A, B and C. (F) HEK 293 were transfected with each construct and assayed for luciferase assay 48 hours after transfection. Data are representative of two individual experiments conducted in triplicate (mean SEM, n=6; comparison to pGL3: *p<0.05, p<0.01, *p<0.001; comparison to pGL3-Saa3-3'UTR-wt: n.s.: p>0.05, ##p<0.01, ###p<0.001; pGL3-Saa3-3'UTR-DelB+C vs. pGL3-Saa3-3'UTR DelB: &p<0.05).
Figure 4:
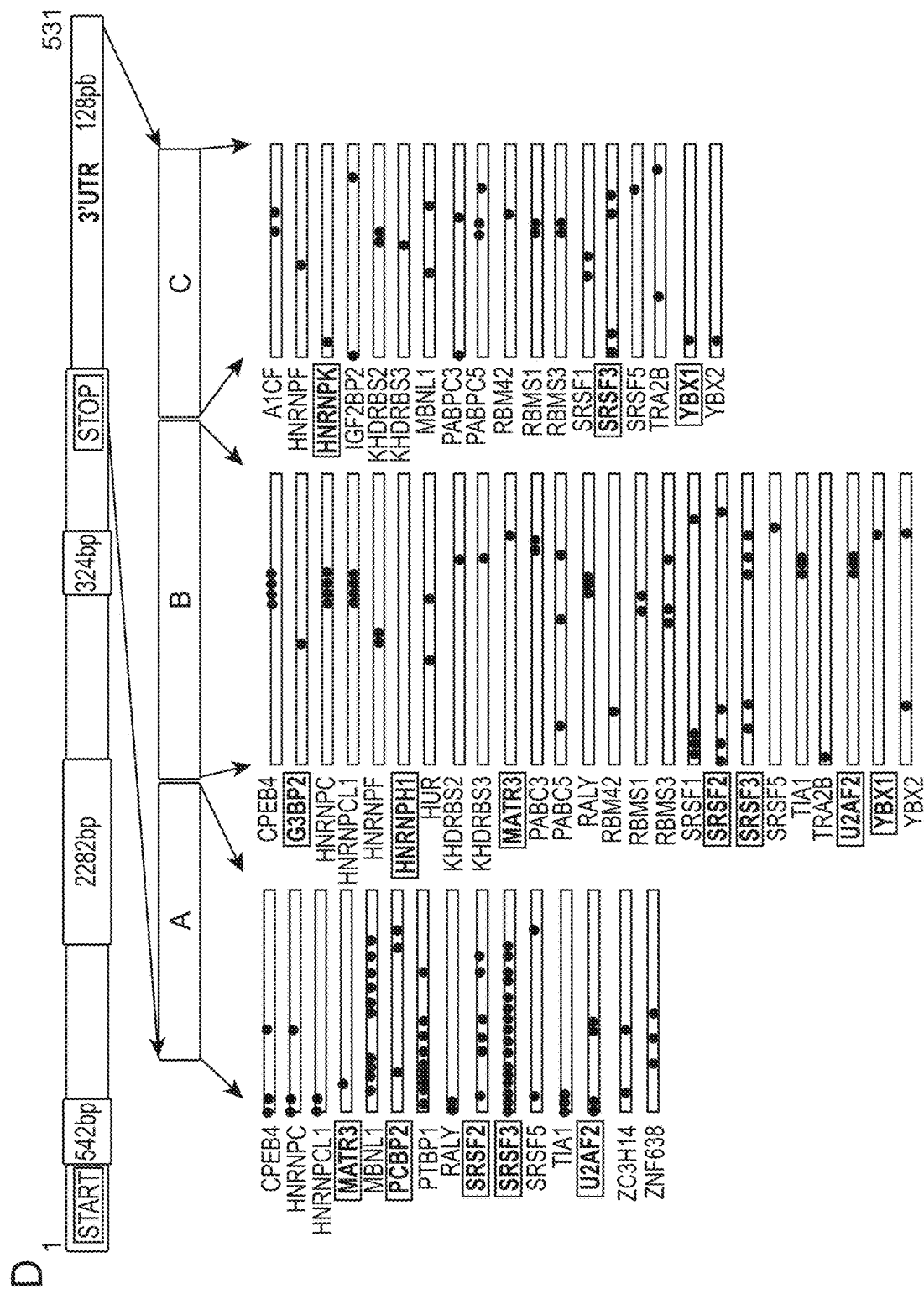
Figure 4:
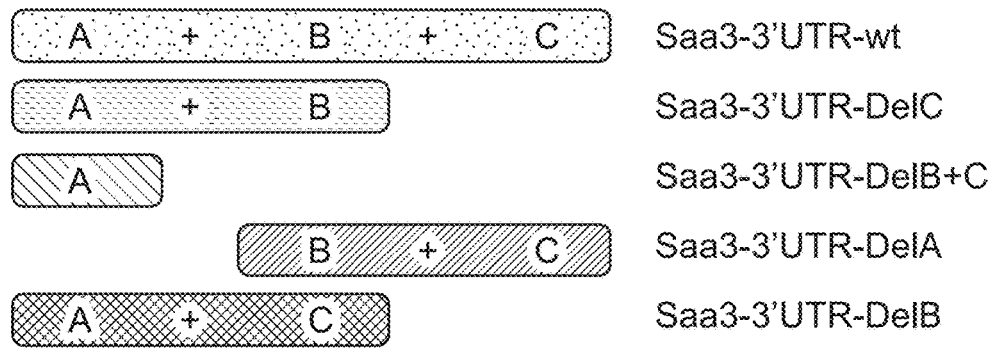
Figure 4:
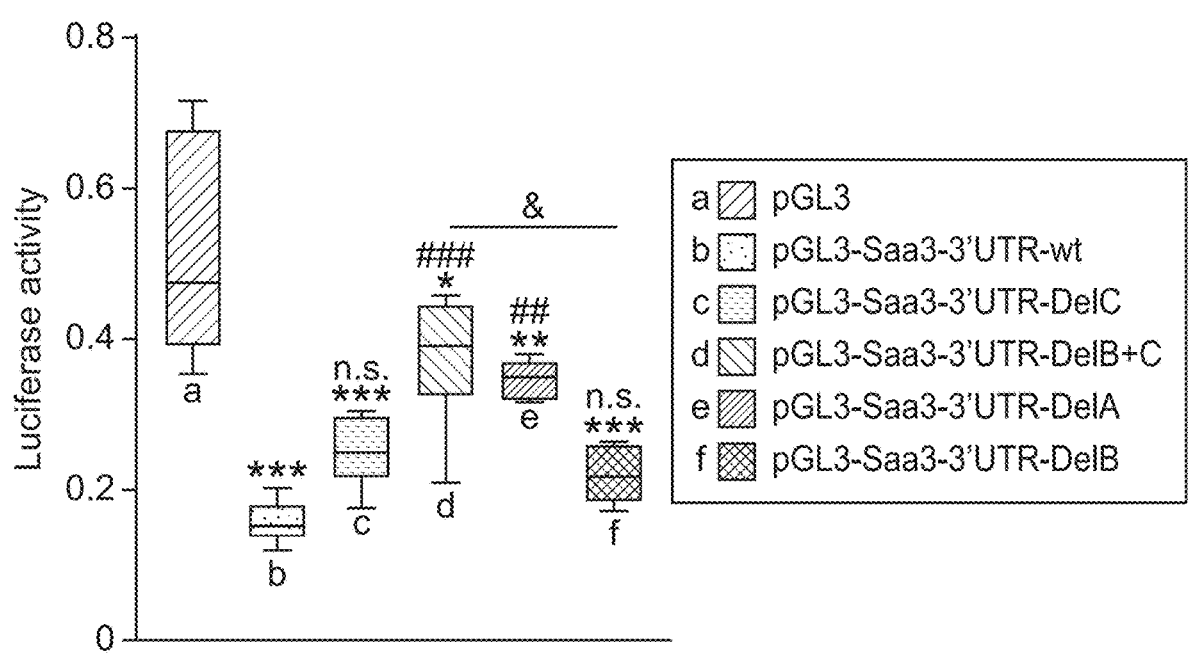
Figure 17:
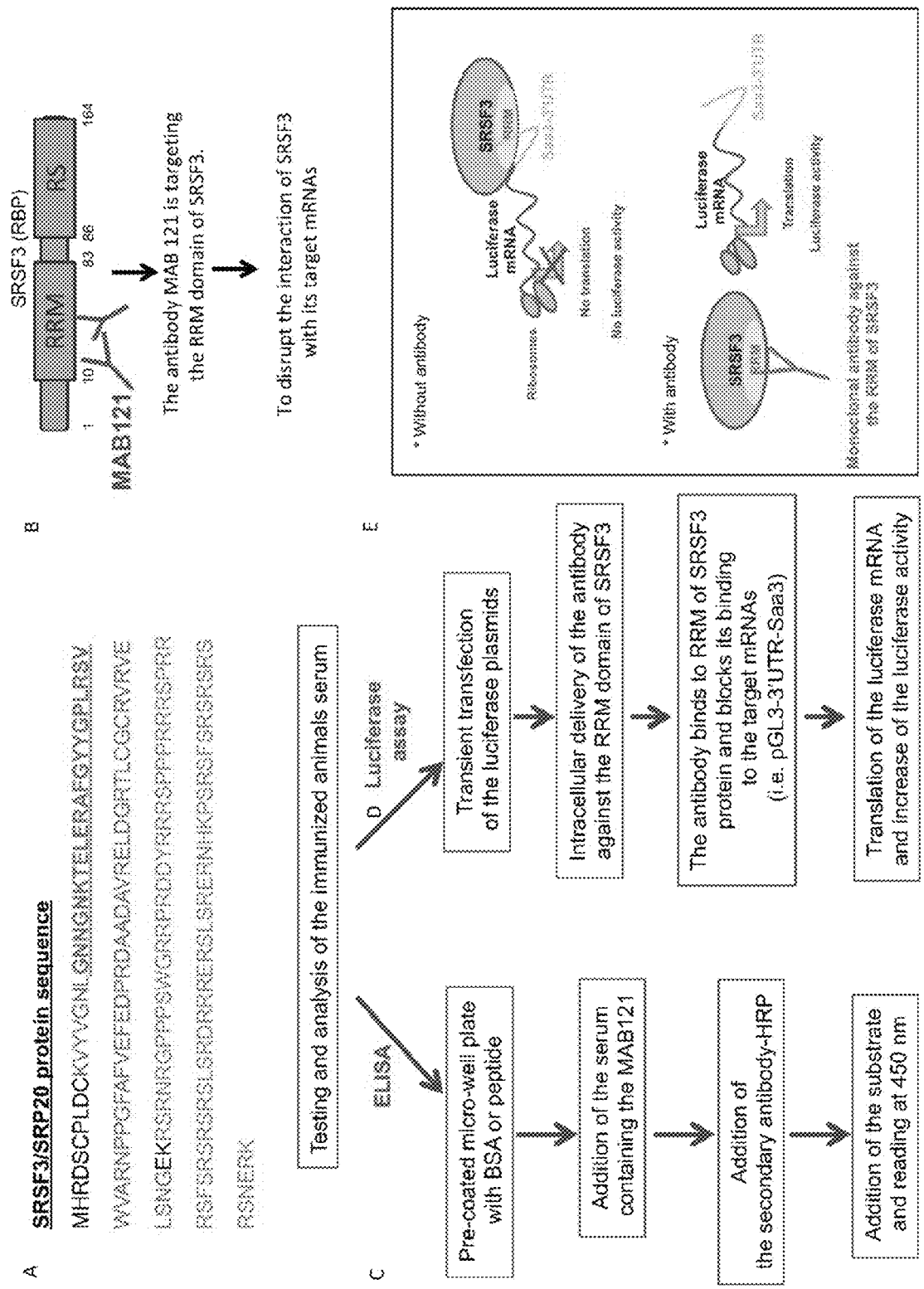

FIG. 17 Production and validation of MAB121 targeting the RNA binding domain of SRSF3 (RRM domain). (A) The sequence of SRSF3 protein. The sequence of the RRM domain (SEQ ID NO 13). is shown in green and the sequence of the RS domain (SEQ ID NO 14) is shown in orange. The unique immunogenic sequence (GNNGNKTELERAFGYYGPLRSV) SEQ ID NO. 20) is shown in bold. (B) Schematics of the involvement of MAB121 antibody in the blocking of the SRSF3 action. Testing and analysis of the immunized animals' serum by (C) ELISA and (D) Luciferase assay. I Schematics of the luciferase assay analysis to check the efficiency of the antibody MAB121 to disrupt the interaction of SRSF3 with its target mRNAs and enhance the luciferase activity. The luciferase reporter system shown in FIG. 4 is used for this experiment.

Figure 18:
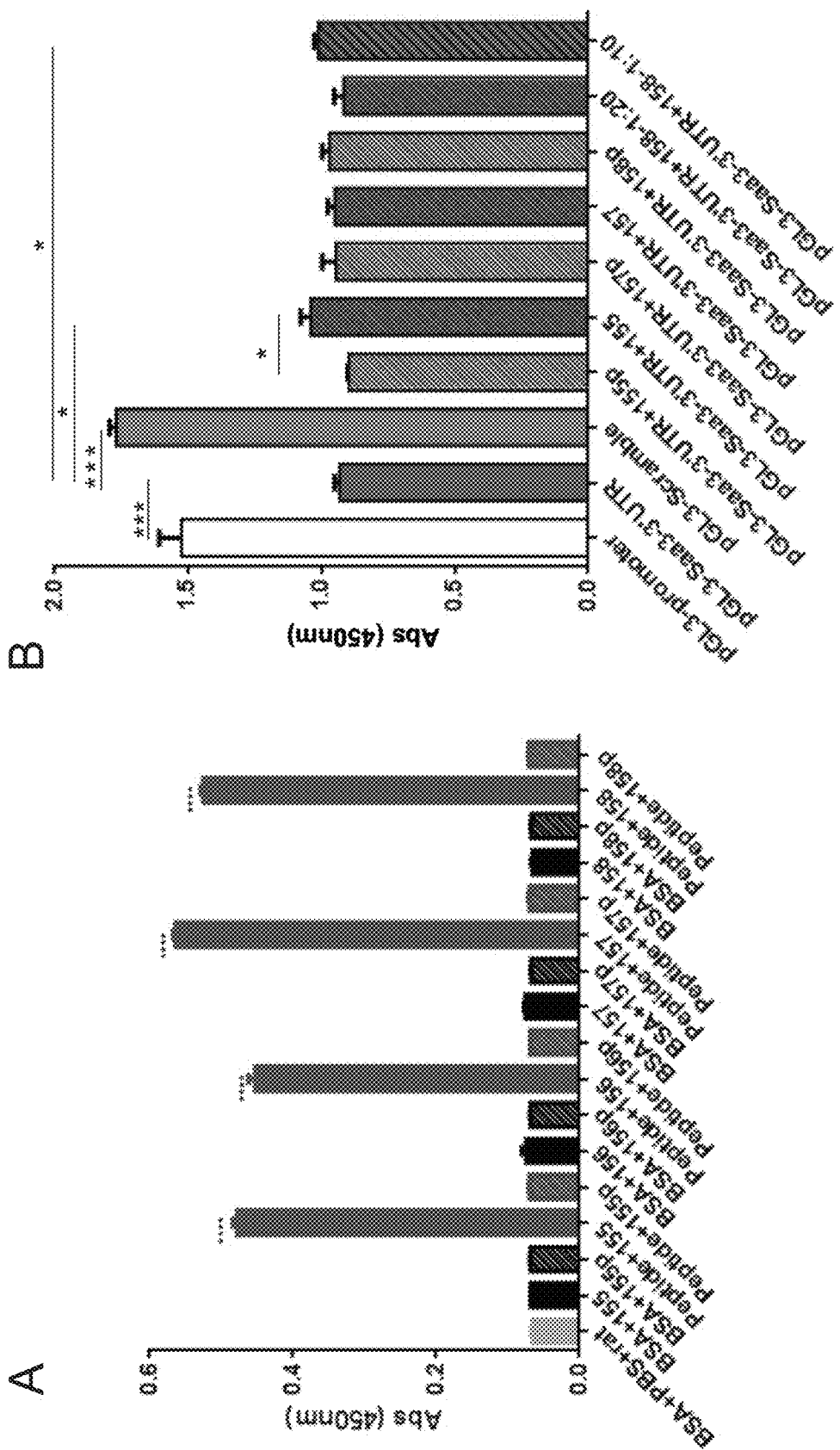

FIG. 18 Analysis of the affinity of different rat serum by (A) ELISA using the synthesized peptide as immunogen or BSA. BSA or the synthesized peptide was incubated with the serum containing the MAB121 antibody or the pre-immune serum (p). Data represent mean±SEM (n=3; **p<0.0001) or by (B) Luciferase assay. HEK 293 cells were transfected with pGL3-promoter (pGL3) (GenBank Accession Number U47298), pGL3-promoter-Saa3-3'UTR-wt (SEQ ID NO:2) (pGL3-Saa3-3'UTR) and pGL3-promoter-SCRAMBLE (pGL3-Scramble) constructs. HEK293 cells transfected with pGL3-Saa3-3'UTR were treated with serum from different immunized animals (Pre-immune serum from each animal was used as control) and assayed for luciferase activity after 48 hours. Data represent mean±SEM (n=3; pGL3-promoter vs pGL3-Saa3-3'UTR: *p<0.001; pGL3-Saa3-3'UTR vs pGL3-Scramble: ***p<0.001; pGL3-Saa3-3'UTR vs pGL3-Saa3-3'UTR+rat #155 (155): *p<0.05; pGL3-Saa3-3'UTR+ pre-immune serum of rat #155 (155p) vs pGL3-Saa3-3'UTR+rat #155: *p<0.05 pGL3-Saa3-3'UTR vs pGL3-Saa3-3'UTR+rat #158 (158): *p<0.05).

Figure 19:
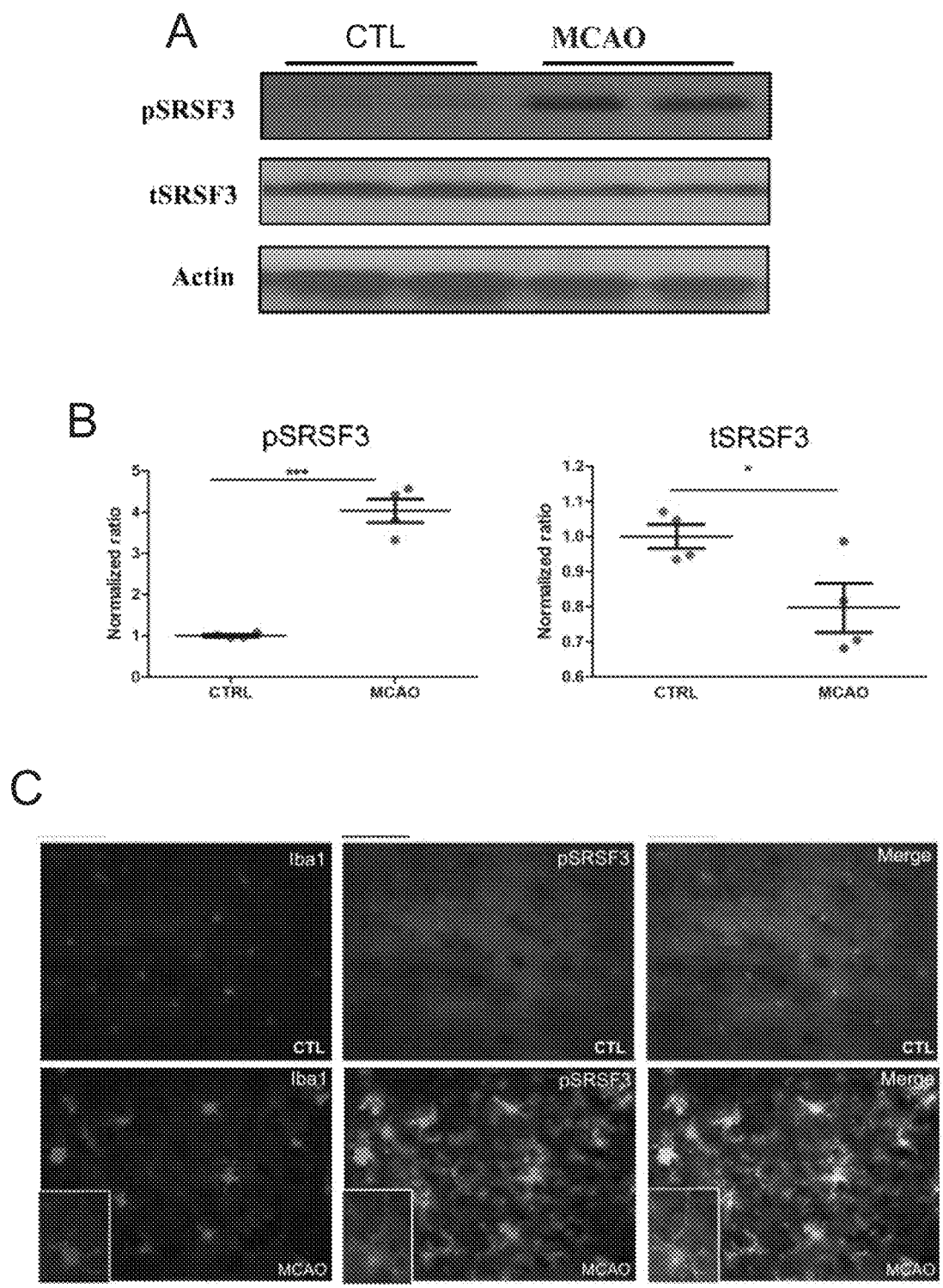

FIG. 19 SRSF3 is implicated in modulation of microglial activation after stroke (A) Western blot analysis of pSRSF3 revealed significant increase in the expression levels 24 hrs after 80 min Middle cerebral artery occlusion (MCAO) when compared to the non-stroked control (CTL) whereas the tSRSF3 is decreased. (B) Quantitative analysis of the western blot. Data represent mean±SEM (n=4; pSRSF3-MCAO vs pSRSF3-CTL: ***p<0.001; tSRSF3-MCAO vs tSRSF3-CTL: *p<0.05). Actin is used as a loading control. (C) Representative double-immunofluorescence images of Iba1 (red) and pSRSF3 (green) in CTL and MCAO.

Figure 20:
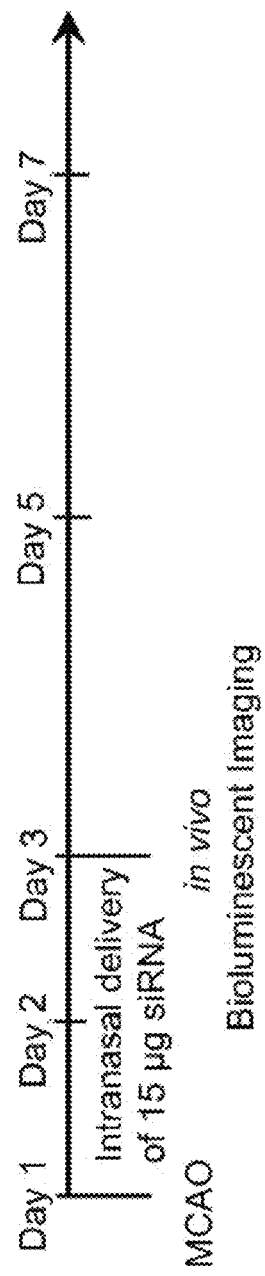
Figure 20:
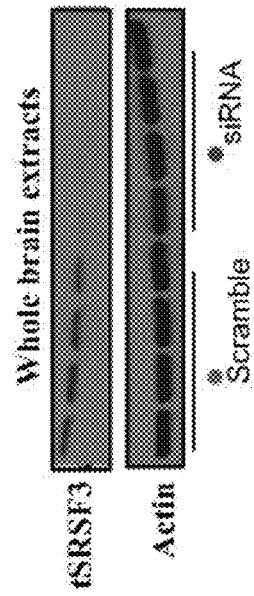
Figure 20:
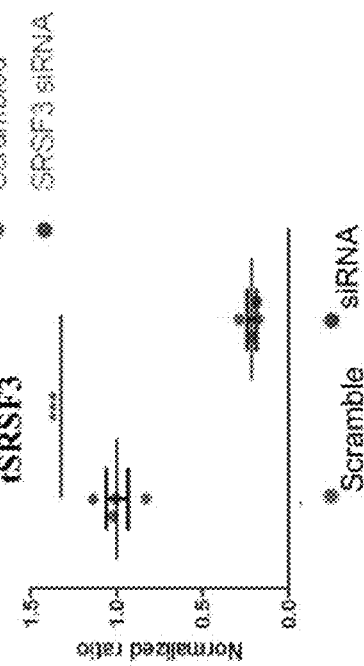
Figure 20:
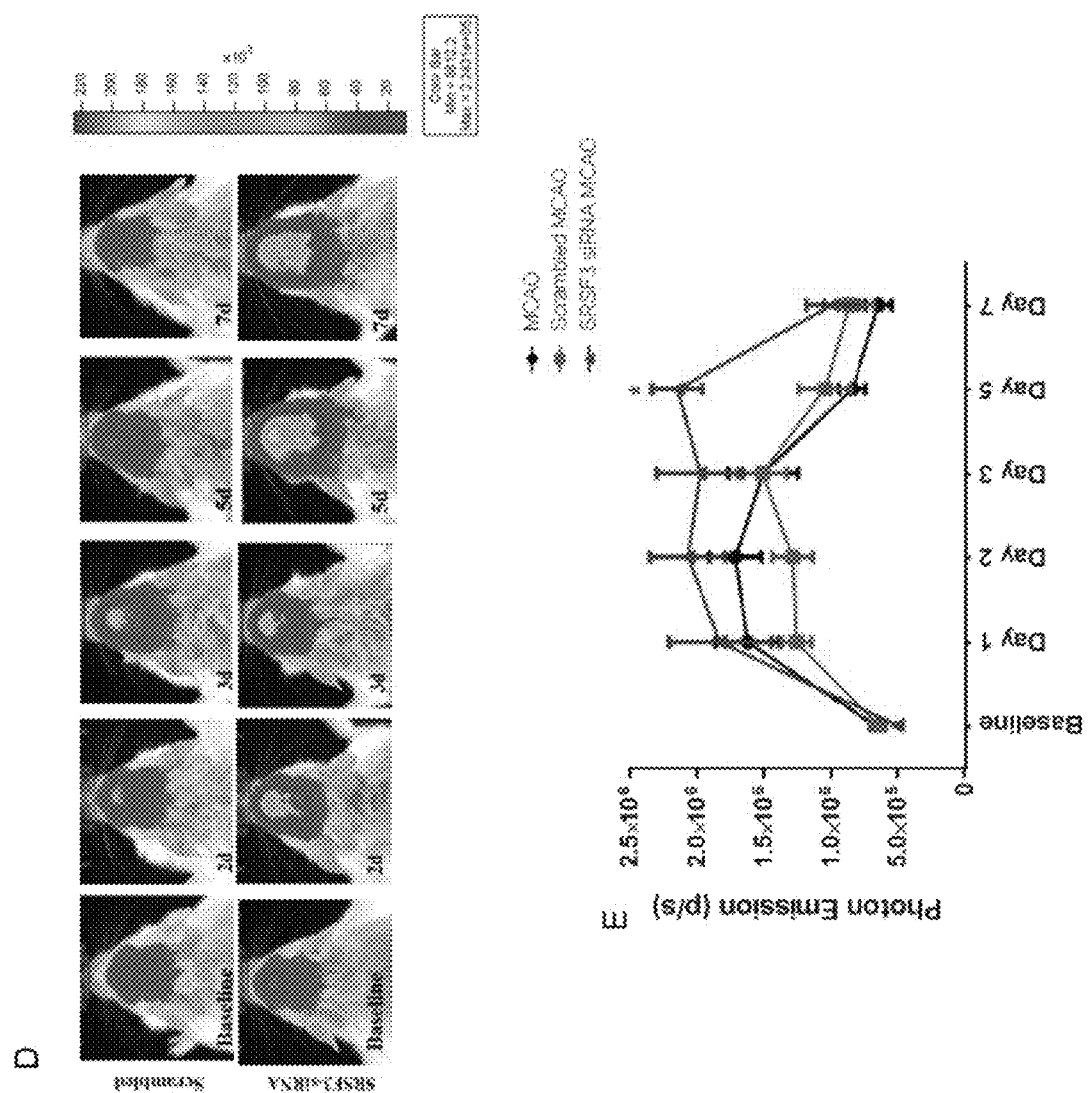

FIG. 20 Increase in microglial activation after the siRNA mediated knockdown of SRSF3 in MCAO (A) Schematic representation of the experiment timeline. (B) Western blot analysis of whole brain extracts after intranasal administration of Scramble-siRNA or SRSF3-siRNA in MCAO condition. (C) Quantitative analysis of the western blot showed the decrease of SRSF3 level after siRNA administration. Data represent mean±SEM (n=4; Scrambled vs SRSF3 siRNA ***p<0.001). Actin was used as a loading control. (D) 2D reconstruction of bioluminescent signal before (baseline) and 2, 3, 5 and 7 days after MCAO induction. I The longitudinal quantitative analysis of the total photon emissions from the brain represented by the photon emission in the TLR2-luc-GFP mice that received SRSF3-siRNA or Scrambled-siRNA 24 hrs after MCAO induction (Data are mean±SEM, MCAO group: n=5; Scramble-siRNA+MCAO: n=6; SRSF3-siRNA+MCAO: n=7; Scrambled-siRNA+ MCAO vs SRSF3-siRNA+MCAO: *p<0.05).

Figure 21:
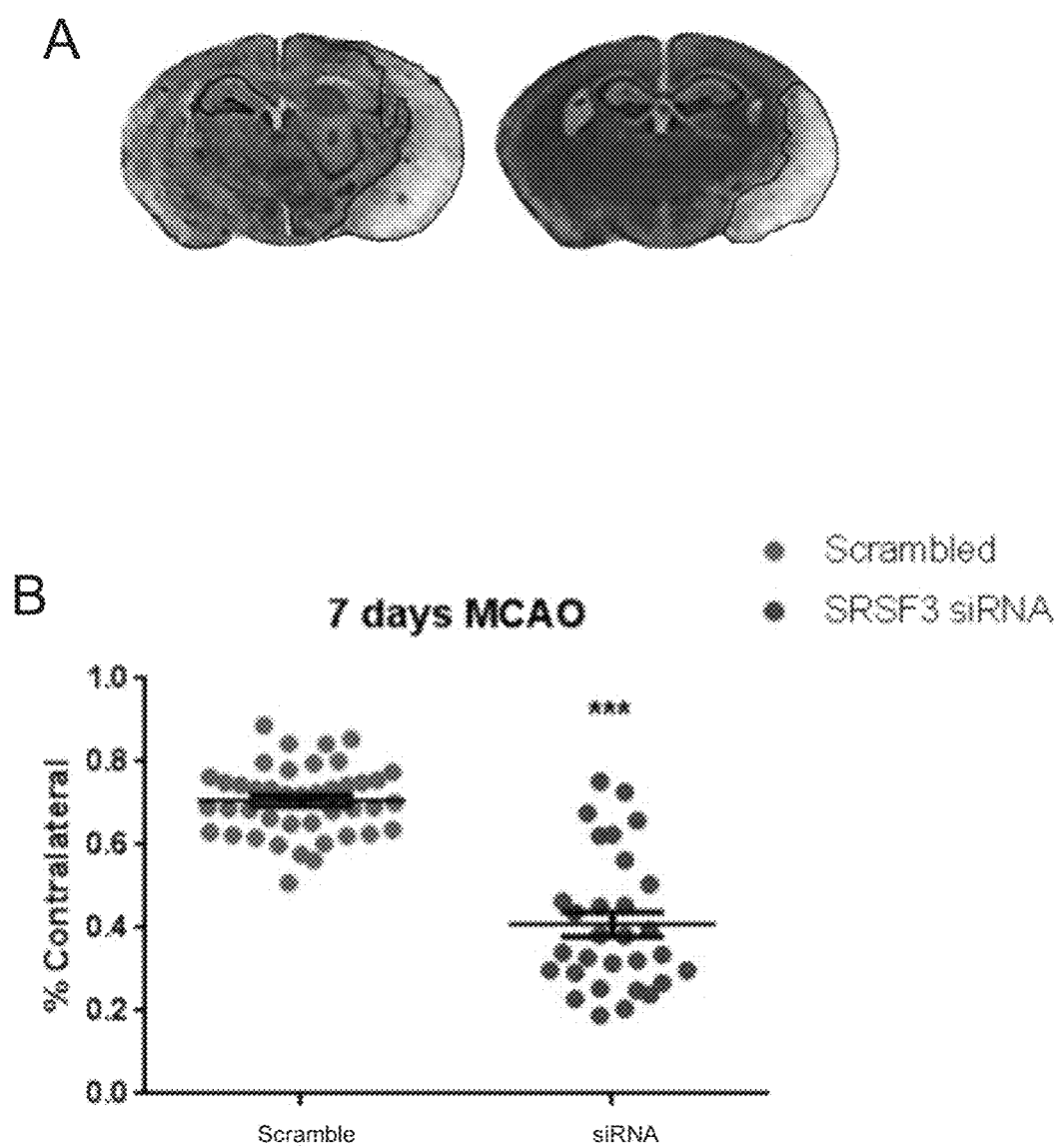
Figure 21:
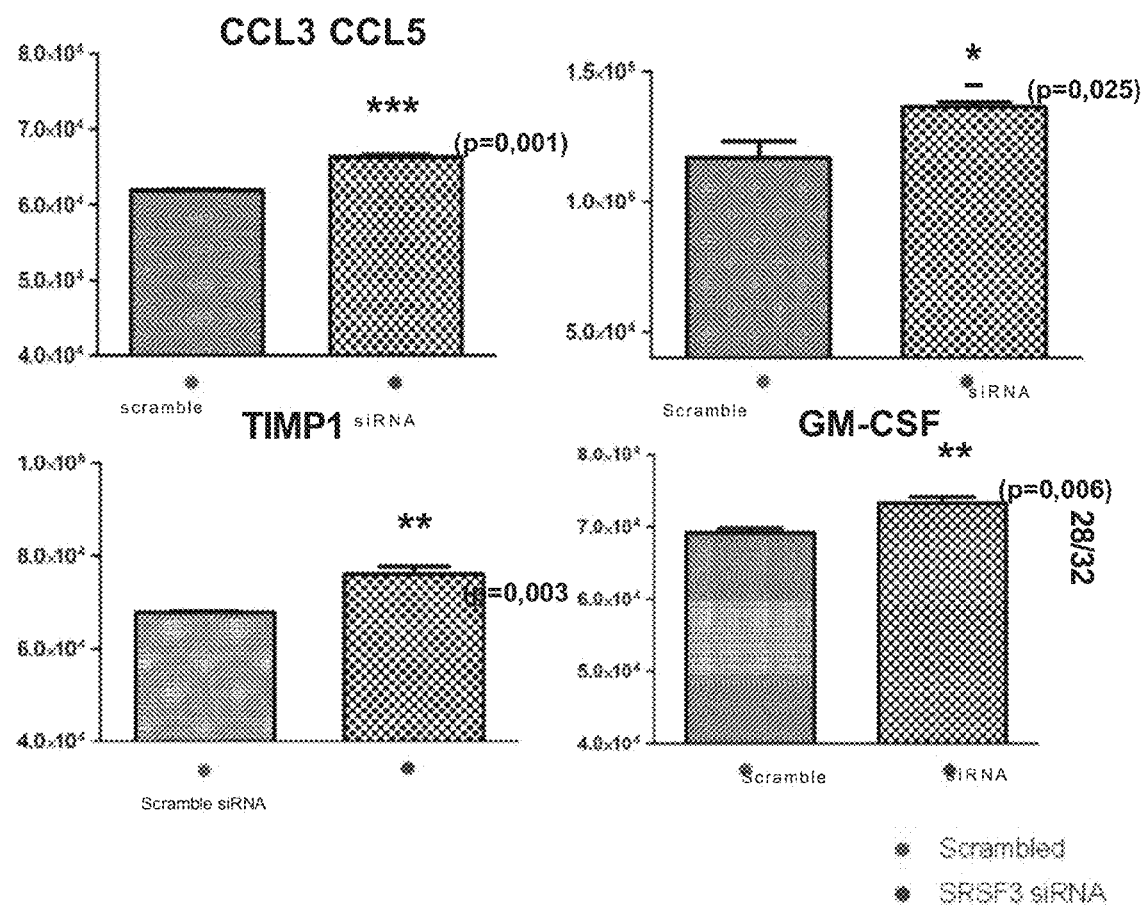

FIG. 21 Intranasal delivery of siRNA 24 hrs after stroke significantly reduced the size of ischemic lesion after stroke. (A) Cresyl violet staining of brain sections showed the infarct volume 7 days after MCAO in Scrambled or SRSF3-siRNA treated mice. (B) Quantification of the infarct volumes showed a significant decrease of the stroke volume after SRSF3-siRNA administration when compared to the scrambled-siRNA. (Data are mean±SEM, *p<0.001). (C) Cytokine array analysis of the stroke area 3 days after MCAO showed a significant increase of the expression of CCL3, CCL5, TIMP1 and GM-CSF after SRSF3-siRNA administration when compared to the Scrambled-siRNA. (Data are mean±SEM, CCl3: *p<0.001; CCL5: *p<0.05; TIMP1: p<0.01; GM-CSF: p<0.01).

Figure 22:
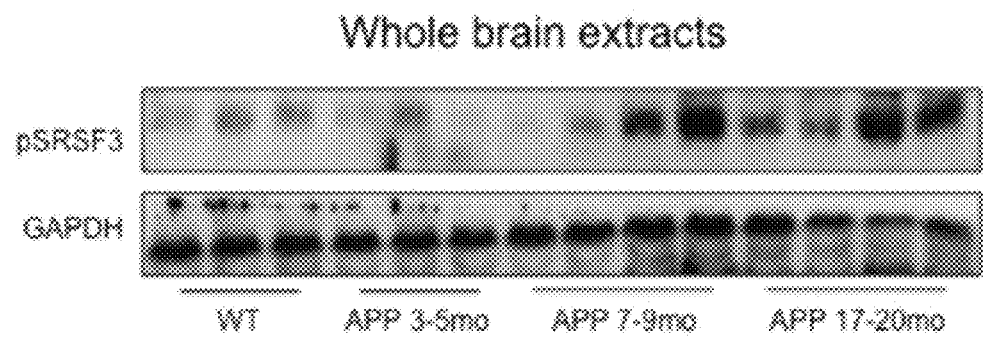
Figure 22:
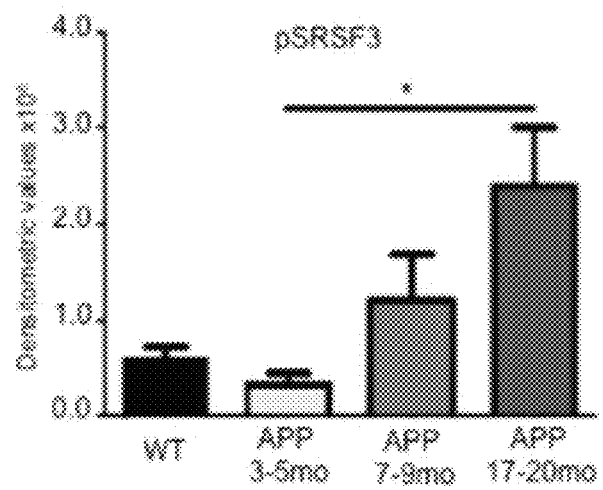
Figure 22:
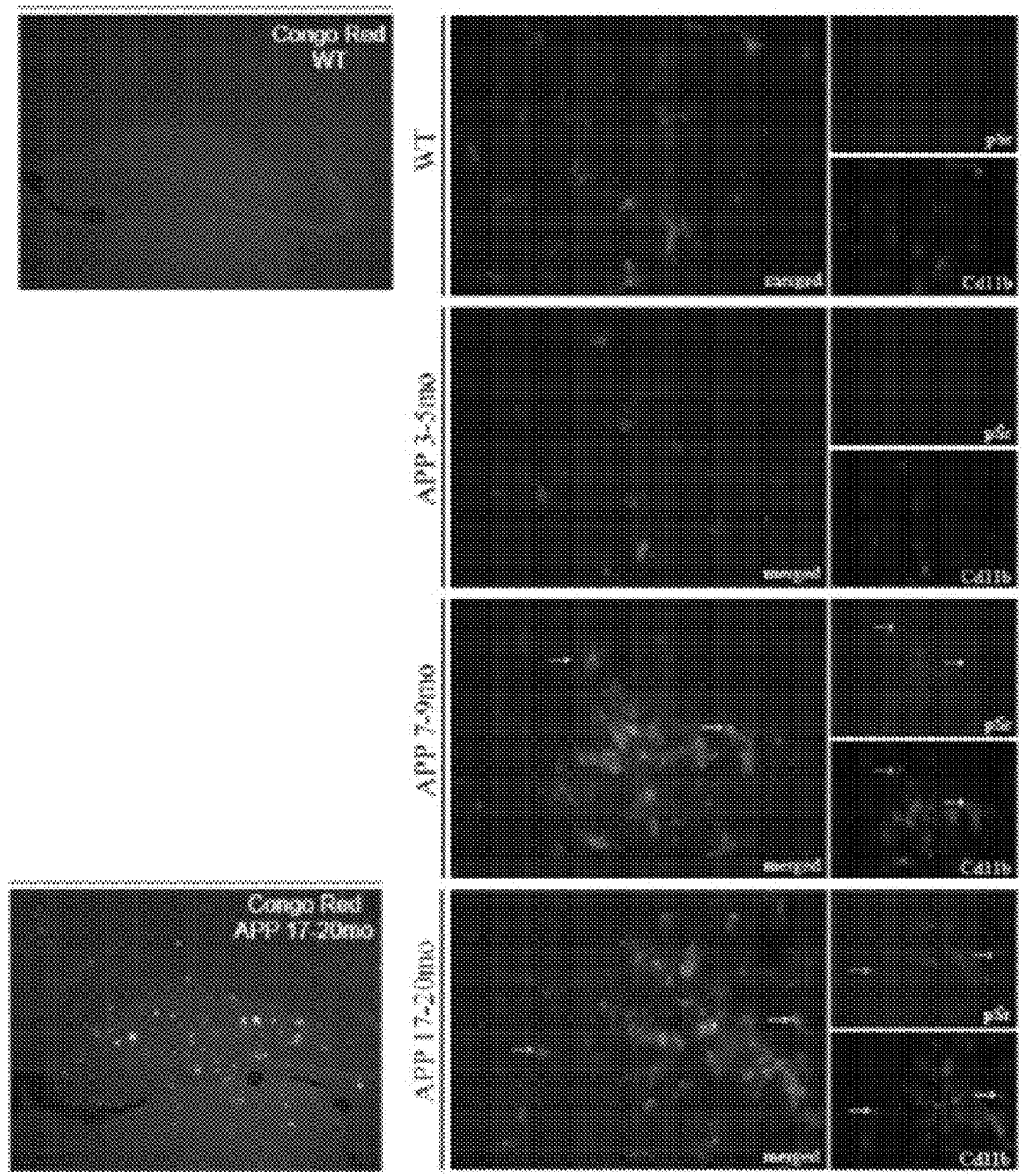

FIG. 22 SRSF3 is implicated in AD pathogenesis as the level of pSRSF3 increases over time in the brains of amyloid precursor protein (APP) transgenic mice. (A) Western blot analysis of phosphorylated form of SRSF3 protein (pSRSF3) in whole brain extracts of APP mice 3-5 months (mo), APP 7-9mo and APP 17-20mo. (B) The quantitative analysis showed that the phosphorylation of SRSF3 is significantly increased starting at the time of onset of disease/onset of cognitive deficits in APP mice. Data represent mean±SEM; (n=3 *p<0.05). GAPDH was used as loading control. (C) Representative photomicrographs of APP transgenic brain sections showed that the phosphorylation of SRSF3 is increased across the disease and starts from 7-9 months. Anti-pSRSF3 protein staining co-localized with CD11b marker in activated microglia. WT mice were used as a negative control. The pictures have been taken from the hippocampus region. The Congo Red was used to stain the amyloid plaques in APP mice 17-20mo and compared to WT mice.

Figure 23:
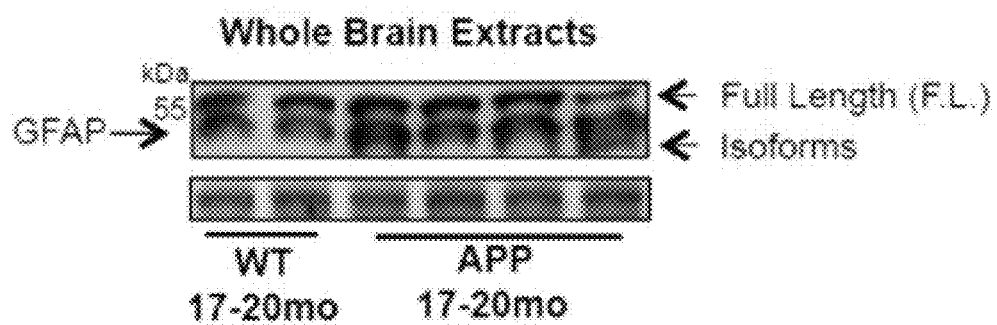
Figure 23:
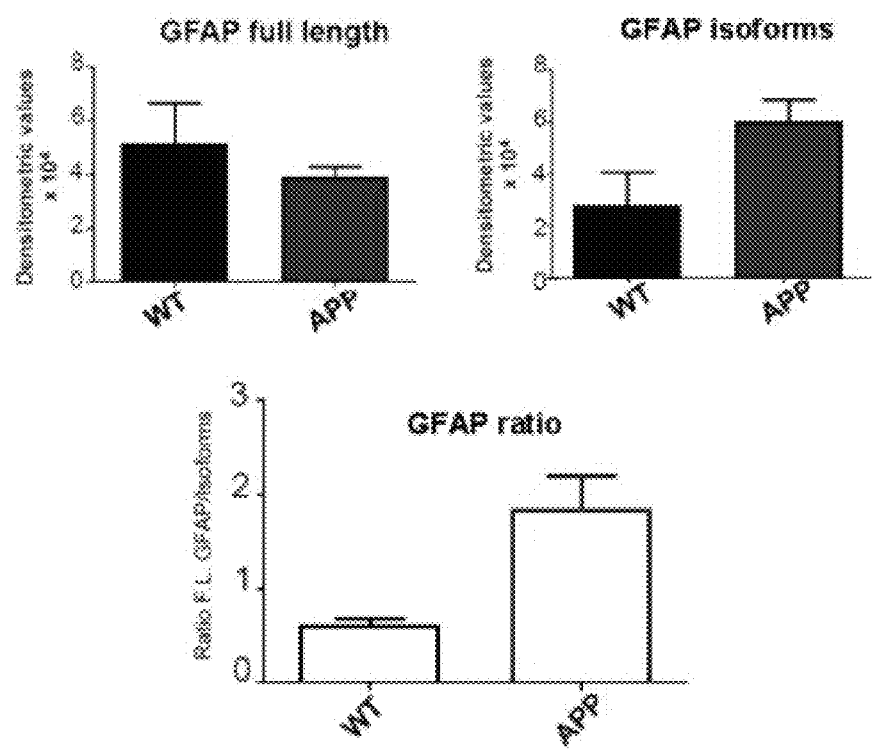
Figure 23:
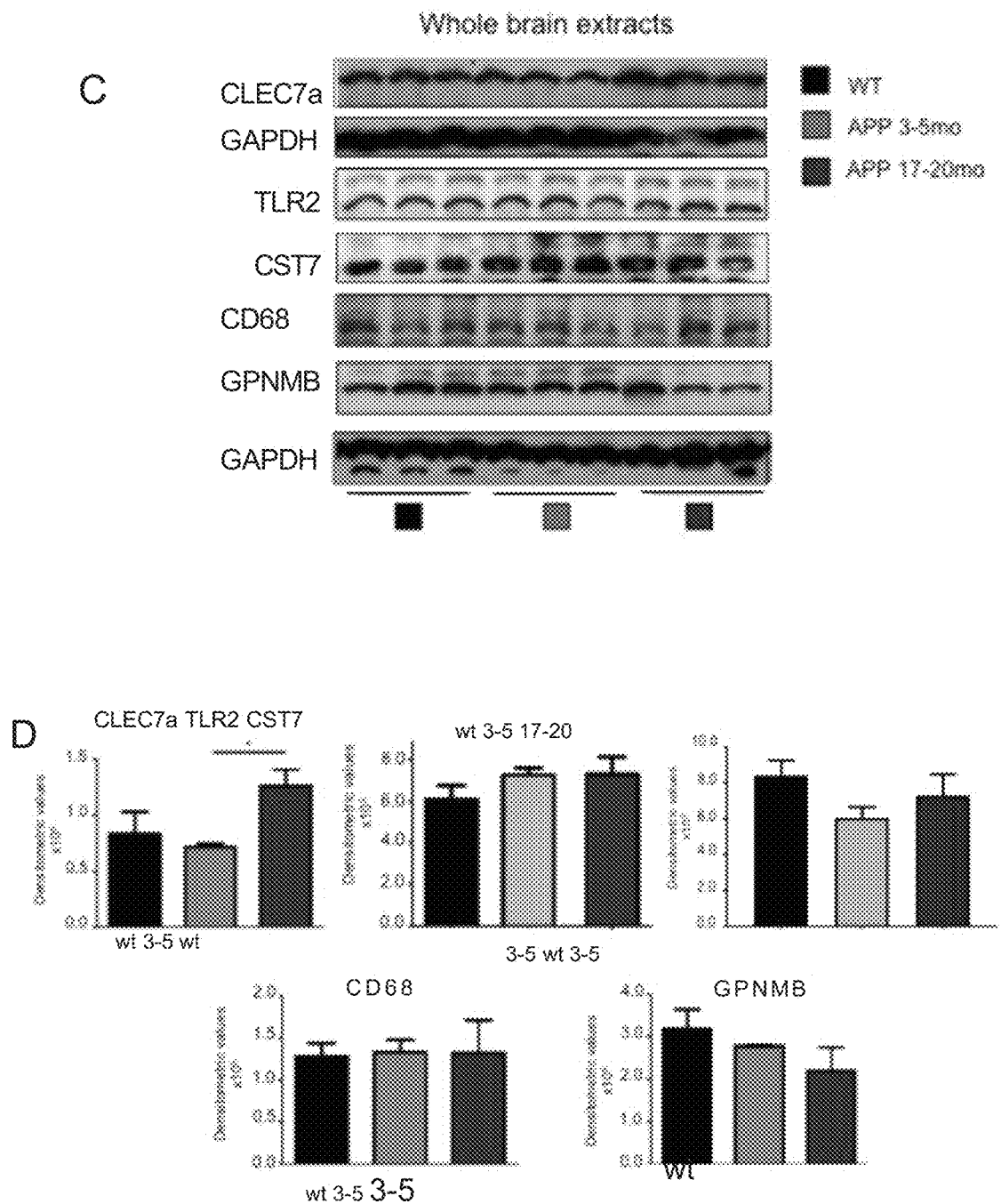

FIG. 23 Highly up-regulated mRNAs are not translated in APP mouse model. (A) Western blot analysis of GFAP protein expression in whole brain extracts from WT or APP mice 17-20mo. GFAP is used as a positive control of the disease progression in APP transgenic mice model (B) The quantitative analysis of the western blot showed a significant increase of the GFAP isoforms expression in APP mice 17-20mo when compare to the age-matched WT mice. Data represent mean±SEM; *p<0.05. Actin was used as loading control. (C) Western blot analysis of CLEC7a, TLR2, CST7, CD68 and GPNMB expression in whole brain extracts of APP transgenic mice (3-5mo and 17-20mo). (D) The quantitative analysis showed no significant difference of TLR2, CST7, CD68 and GPNMB expression level across the disease except for CLEC7a for which we observed an increase of its level expression in APP-17-20mo. Data represent mean±SEM; (n=3 *p<0.05). GAPDH was used as loading control.

Figure 24:
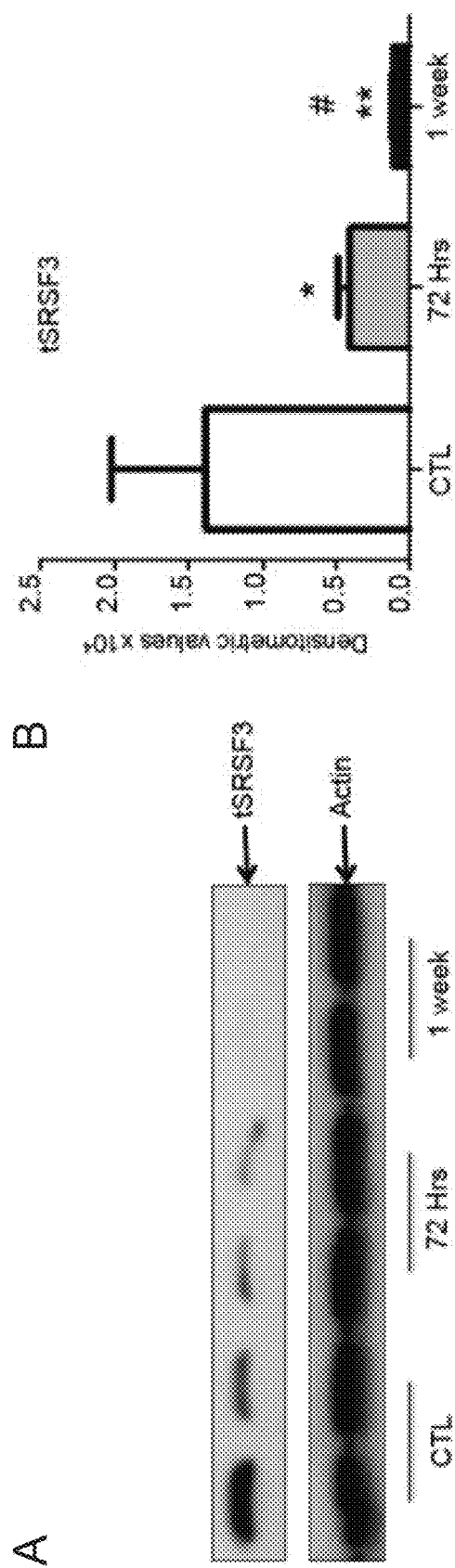

FIG. 24 Knockdown of total SRSF3 after intranasal delivery of morpholino against SRSF3 mRNA (50 μg). (A) Western blot analysis of the total SRSF3 knockdown three days and 1 week after intranasal delivery of the morpholino targeting Srsf3 mRNA. (B) Densitometric analysis of western blot obtained from whole brain extracts. Data represent mean±SEM; (n=3 CTL vs 72 Hrs: *p<0.05, CTL vs 1 week; **p<0.01, 72 Hrs vs 1 week: #p<0.05). Actin was used as loading control.

Figure 25:
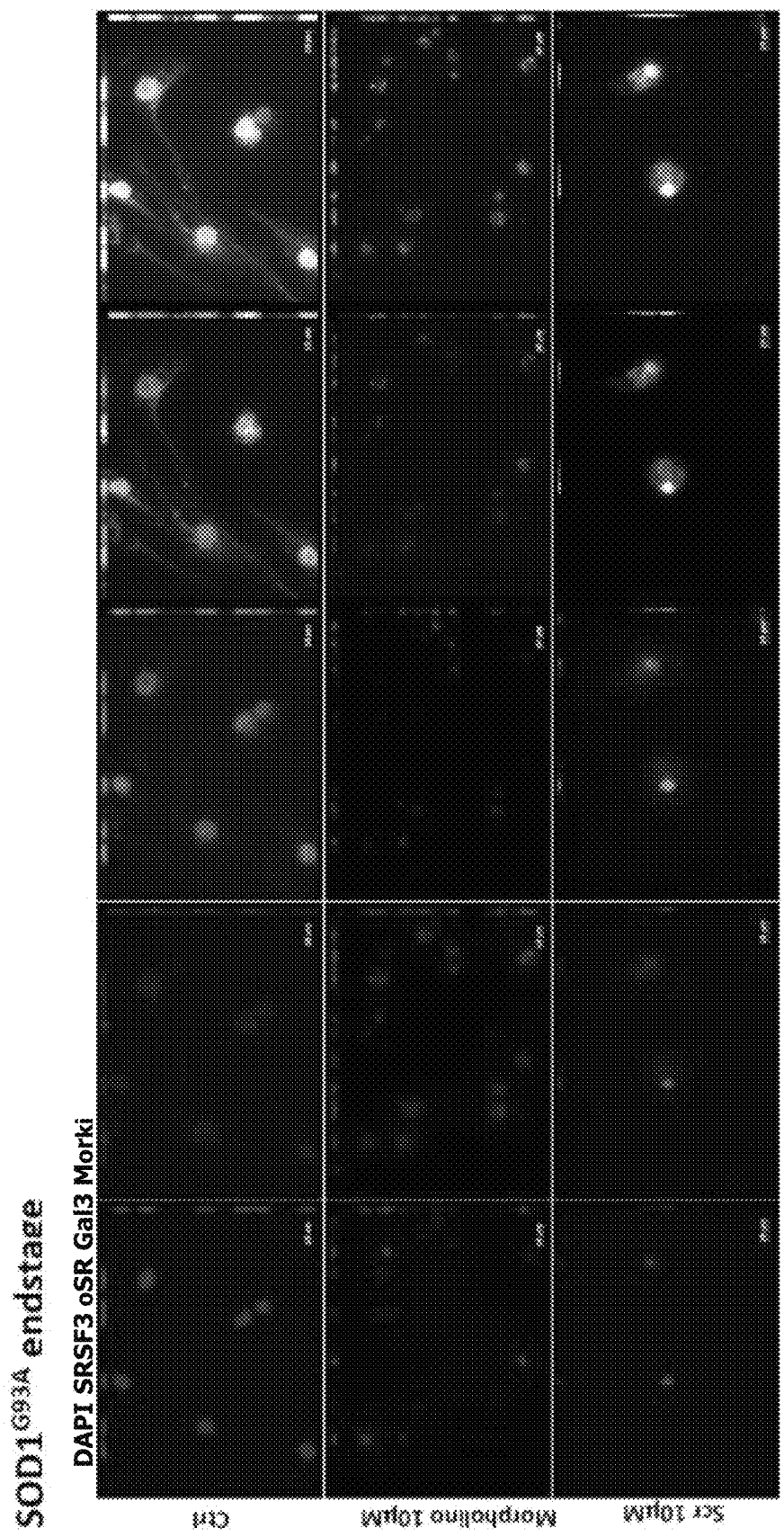

FIG. 25 Treatment of primary adult microglial cells derived from spinal cord of symptomatic SOD1G93A mice with 10 μM anti SRSF3 morpholino decreases expression of Gal3, one of the markers associated with aberrant ALS microglia.

DETAILED DESCRIPTION

The present description relates to the surprising finding that by blocking translation of highly regulated LPS genes, SRSF3 (Serine/Arginine-Rich Splicing Factor 3 (SRSF3/SRp20/SFRS3)) serves as a master regulator of innate immune response in resident microglia.

To decipher the molecular mechanisms of microglial activation in vivo, the present inventors created a transgenic model in which the Flag/EGFP was fused to the N-terminus of the large subunit ribosomal protein L10a and expressed under the transcriptional control of a myeloid specific gene promoter (SEQ ID NO:1). By isolating both, the ribosome-attached mRNAs and peptides, the present inventors obtained a snapshot of a dynamic translational state of microglia ribosomes with mRNAs as input and newly synthesized peptides as output. Using this strategy, mRNA and protein signatures associated with microglial activation were identified. A parallel analysis of the ribosome bound peptides revealed that the most highly up-regulated mRNAs were not translated. Contrary to highly up-regulated pro-inflammatory mRNAs, a majority of the sequenced peptides, including peptides forming the key immune NF-κB interactome, were either down-regulated and/or un-regulated. A ribosome-based check point/control: a selective 3'UTR-mediated translational repression of highly expressed, ribosome-bound and "actively translating" mRNAs was identified. It was found that the translational repression of the highly regulated genes was orchestrated by RBP Serine/Arginine-Rich Splicing Factor 3 (SRSF3/SRp20/SFRS3) that possess multiple putative binding sites in all domains of 3'UTR of Saa3 and other highly regulated LPS genes.

By investigating the molecular patterns of microglial activation in response to innate immune challenge, a marked dissociation in microglia mRNA and protein molecular signatures was discovered. The most striking divergence was observed in the key immune NF-κB network where it was found that cluster of highly up-regulated LPS-induced and ribosome-associated mRNAs were not translated. This rather selective translational repression of the highly regulated LPS-induced mRNAs resulted in formation of two distinct microglia molecular signatures: i) a highly specialized immune and pro-inflammatory mRNA signature and ii) a more immunomodulatory homeostatic protein signature. Notably, the observed translational repression was restricted to a cluster of the highly up-regulated LPS-induced genes while the un-regulated transcripts were normally translated and detected at expected level by mass spectrometry and western blot analysis. Next, it was found that the 3'UTR region plays a key role in the translational control of highly up-regulated and ribosome-attached immune transcripts. Moreover, the RNA binding protein SRSF3 was identified as a master regulator of the innate immune genes translation in microglial cells. It was also found that SRSF3 possesses putative binding sites on several up-regulated innate immune genes. In addition, a selective knockdown of the endogenous SRSF3 by siRNA in the context of LPS challenge alleviates translation repression of several highly regulated innate immune genes, thus resulting in a robust increase in protein synthesis of immune mediators including SAA3, CCL5 and CCL3. Given the fact that SRSF3-mediated suppression of protein production targets the ribosome bound mRNA, this strongly suggest the existence of a regulatory mechanism/check point of immune gene translation that operates after initiation of protein synthesis and controls microglia activation.

Under physiological conditions microglial cells are instrumental in the maintenance of brain homeostasis, however, uncontrolled and long term activation of microglial cells is detrimental to neurons (Prinz and Priller, 2014). Thus, there is an increasing interest in understanding the molecular mechanisms involved in microglia activation. While published studies have been focusing on identification/description of a context-dependent microglia immune transcripts (Beutner et al., 2013; Butovsky et al., 2014; Hickman et al., 2013; Zhang et al., 2014), the in vivo microglia proteomics and associated regulatory mechanisms are less well defined. The first comprehensive adult mouse brain proteome has been presented by Sharma and colleagues (Sharma et al., 2015). However, their analysis was restricted to the adhesion molecule Lsamp and its expression patterns across the brain and different cell-types. One of the limiting factors in better understanding of the molecular mechanism of microglial activation has been a lack of adequate in vivo models. By studying translation dynamics of the microglial ribosomes a marked divergence of mRNA and protein molecular signatures following LPS challenge was found. Translation of mRNA into proteins in innate immune response, is a highly regulated process and to date several post-transcriptional mechanisms targeting the stability of the transcripts have been described (Anderson, 2010; Carpenter et al., 2014; Mino et al., 2015). However, the results described herein revealed that the regulation of the mRNAs occurs after the initiation of translation. The described process was selective for the highly regulated innate immune mRNAs, while the un-regulated transcripts were normally translated and detected at expected levels by quantitative mass spectrometry. Importantly, the 3'UTR region of the targeted mRNAs was highly enriched in putative binding sites for the RBP SRSF3. Therefore, the observed divergence of mRNA and protein response following LPS challenge can be in part explained by the 3'UTR-mediated inhibitory effects exerted by SRSF3.

Figure 11:
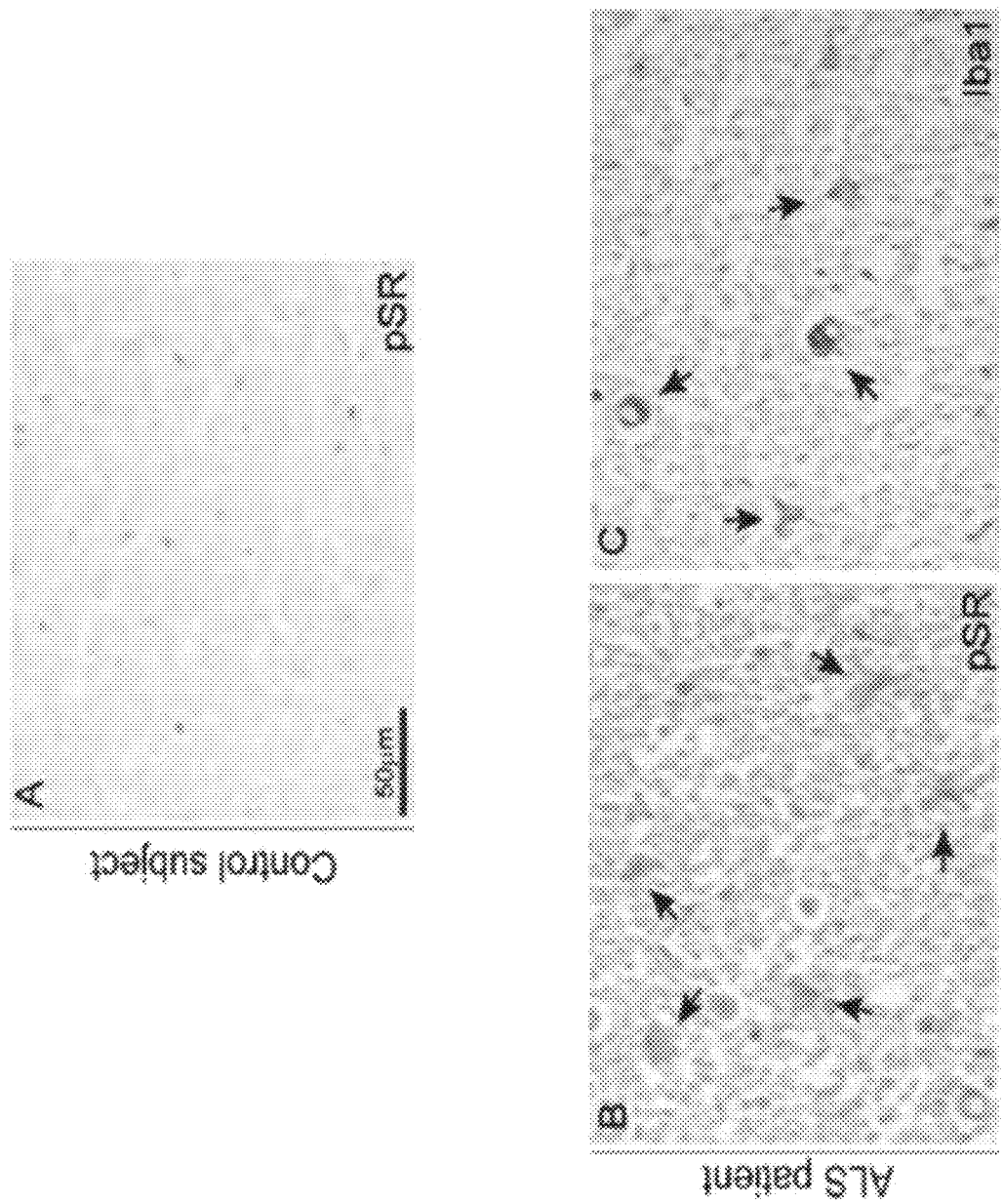
FIG. 11 pSRSF3 levels are elevated in the Cerebrospinal fluid (CSF) of sporadic ALS patients 11 pSRSF3 is detected in Human Spinal Cord, Cerebrospinal fluid (CSF) and plasma. pSR immunohistochemistry was performed on paraffin-embedded post-mortem human spinal cord sections from ALS patients (B, C) and Control subject (A). (D) Western blot analysis of plasma from ALS patients and Control subjects. (E) Quantitative analysis of western blot showed the increase of pSRSF3 level in the ALS patients when compare to the control subjected. Data are mean±SEM (n=4; *p<0.01). (F) Western blot analysis of CSF from ALS patients and Control subjects. *Faint band observed in a higher exposure. (G) Quantitative analysis of western blot showed the increase of pSRSF3 level in the ALS patients when compare to the control subjected. Data are mean±SEM (n=5; **p<0.01).
Figure 11:
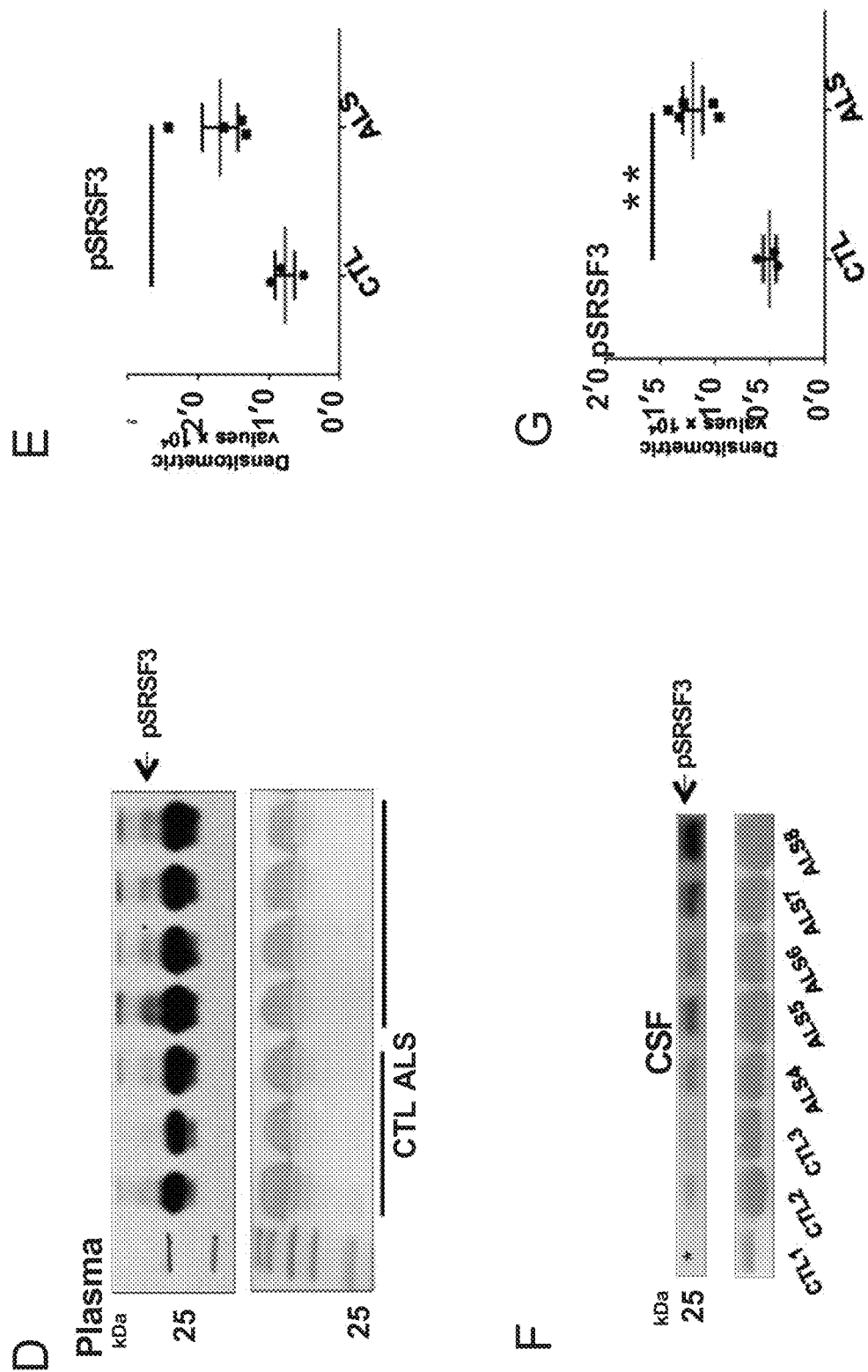

In addition, it was also found that SRSF3 is upregulated in the spinal cord of ALS induced SOD1 model mutant mice (FIG. 9) and in the cerebrospinal fluid (CSF) of sporadic ALS patients (FIG. 11). It was also found, as disclosed herein, that SRSF3 is upregulated in normal aging and in a mouse model of Frontotemporal dementia (FTD) (TDP-43$^{G348C}$). Without being bound to any specific theory, the present inventors believe that a mechanism similar to the one observed in LPS challenged microglial cells exist in neurological conditions, cancer of the central nervous system, antiviral and bacterial infections (especially infections that target immune cells). The inventors believe that translational repression operated by SRSF3, or phosphorylated SRSF3, will silence immune functions in myeloid cells that would otherwise be relevant for the control and treatment of neurological conditions, cancer of the central nervous system and infections.

Neuroinflammation and activation of microglia is a hallmark of many brain pathologies. In ALS as well as in other neurodegenerative disorders, over the course of disease, microglial cells change their phenotypes from initially beneficial into highly neurotoxic and aberrant cells resistant to any therapeutic interventions (including conventional anti-inflammatory approaches). Furthermore, increasing evidence suggests that chronic brain inflammation in ALS and/or AD may be associated with a marked deregulation of innate immunity at periphery (Zang et al 2005, 2009, 2013). A series of our recent experiments revealed that changes in SRSF3 activity (e.g. changes and its expression levels and/prosphorylation) may regulate innate immune response in the brain and at periphery. Indeed, the present inventors have revealed the role of SRSF3 in the microglial response to systemic injection of endotoxin LPS (a model of acute innate immune response to infection). Targeted knockdown of endogenous SRSF3 by siRNA approach was shown to alleviate translational arrest of the SRSF3 modulated innate immune genes and was associated with de novo synthesis of proteins.

In one aspect, SRSF3 could be used as a target for regulating/normalizing the phenotype of myeloid cells (e.g. microglial or monocyte cells) to regain of immune functions in different pathological conditions.

In one aspect, the SRSF3 agent are used for the treatment of cerebrovascular accident (CVA) such as an ischemic stroke caused by a blockage or a hemorrhagic stroke caused by the rupture of a blood vessel. Analysis of the post-ischemic inflammation revealed that SRSF3 is involved in modulation of microglial activation after stroke. As shown in FIG. 19A, levels of pSRSF3 were significantly increased after stroke Double immunfluorescence analysis revealed that expression of pSRSF3 after stroke was restricted to lba1 positive activated microglia. Intranasal delivery of siRNA targeting SRSF3 24 hrs after stroke induced a significant knockdown of endogenous protein (FIG. 20A-C). The intranasal delivery of siRNA as a therapeutic approach is described herein. The therapy was designed as a single dose that would transiently reprogram delayed/proregenerative phase of the immune response after stroke. siRNa mediated knockdown of endogenous SRSF3 induces a marked increase in innate immune response 3-5 day after stroke that was visualized in vivo using the TLR2 reporter mice. Importantly, delayed induction of innate immune response/microglial activation was associated with a significant decrease in the size of ischemic lesion and delayed increase in expression levels (proteins) of certain immune molecules known to be regulated by SRSF3, such as CCL3, CCL5 and related genes. Hence, targeted knockdown of SRSF3 initiated 24 hrs after stroke increases delayed inflammatory response after stroke and decreases ischemic lesion (FIG. 21).

In summary, the present inventors discovered a ribosome-based mechanism/check point involved in the molecular control of myeloid cells (e.g. microglial activation). The present inventors also showed that RNA binding protein SRSF3 acts as a master regulator of the highly up-regulated innate immune gene translation and thus plays a pivotal role in the control of innate immune response. This opens avenues for targeted therapeutic regulation of myeloid cells (e.g. microglial activation) and innate immune response.

SEQUENCE LISTING

TABLE 1

Figure 12:
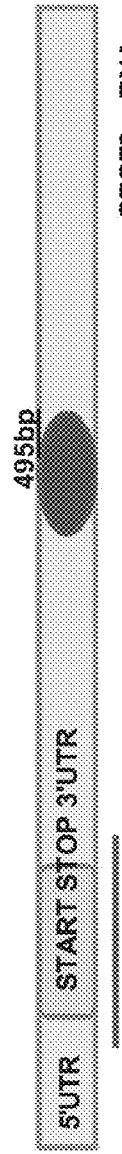
FIG. 12 Schematics of anti-SRSF3 Morpholinos mechanism in the cytosol. The anti-SRSF3 morpholinos are short chains of 25 nucleic acid bases targeting the 5'UTR of the SRSF3 mRNA. They bind to the complementary RNA and act via an RNAse H-independent mechanism to block the translation initiation of SRSF3 in the cytosol. The sequence of the anti-*Mus musculus* SRSF3 morpholinos is: 5'-CCAAGGGACAGGAATCACGATGCAT-3' (SEQ ID NO: 15). Brackets have been inserted around the mRNA target to illustrate its position in the *Mus musculus* sequence of SRSF3 [shown below]. Note that the brackets are placed on a sense strand (SEQ ID NO: 16)
5'ggtgggcctgtcggagcgttaggatttgagcttgggccttttgaac ccaggatctcgaa[(atg)catcgtgattcctgtcccttgg]-3'.

| SEQ ID NO: | Name |
|---|---|
| 1 | CD11b p-I-Flag-EGFP-Rpl10a-II |
| 2 | Saa3-3'UTR-wt (pGL3-promoter) |
| 3 | Scramble (pGL3-promoter) |
| 4 | Saa3-3'UTR-DelC |
| 5 | Saa3-3'UTR-DelB + C |
| 6 | Saa3-3'UTR-DelA |
| 7 | Saa3-3'UTR-DelB |
| 8 | siRNA-1 GAAAGGCACCUGAGAAUAU (SEQ ID NO: 8) |
| 9 | siRNA-2 CCAGAUGAGAUUUAGGUAU (SEQ ID NO: 9) |
| 10 | siRNA-3 CUAGCAUAAUUGUGUAGUA (SEQ ID NO: 10) |
| 11 | siRNA-4 CUAGAAGGUUCCAACAUGA (SEQ ID NO: 11) |
| 12 | SRSF3 |
| 13 | RRM domain of SRSF3 |
| 14 | RS domain of SRSF3 |
| 15 | Mouse antisense (5'-3') (FIG. 12) |
| 16 | mRNA mouse 5'UTR target sequence (FIG. 12) |
| 17 | Human antisense (5'-3') (FIG. 12) |
| 18 | mRNA human 5'UTR target sequence (FIG. 12) |
| 19 | Pre-mRNA 5' UTR human SRSF3 tttccaggtcacctgaccggtctcctttgctgtcggcgccaagtc ctgcaagtttgcttgagagacgagaaaccagcaagagttgggcaa actttccaaaccaggcttttccttcagtgtggaatctaggcggcc acagtctggtgccagctgggtcacaaacagctccgtgacctgttt gtaaacgcgatgctcttagttccagactaaccgctcacaagggtg aagcacttaatttaattcatctcttaatcttgttaggggccaacgg ctcctattagtgtttgagcgtgacggcgacggtgctgtttatgaa gccctagcctatttggaggtgaggaagaggagtctgtgggtaacc tggaggtcgacagaccgggaggaacgctcgagggagcaccaggcc tgttacaacgagcgcgcgccgacgcacgtctccacccacccggcg caaccgccagagcgcgctcccagcaaccgcggctctcgctgcgtt tgtagccatacgtcacggcctcttctgcttctcattgggggagcc cgtccaatcatgtgattccagtatggcgtataaataaaggcgagg agaaggcggtggtccgccatttcgtggacgccgggtgagtgagag agttggttggtgttgggccggaggaaagcgggaagactcatcgga gcgtgtggatttgagccgccgcatttttttaaccctagatctcgaa (SEQ ID NO: 19) |
| 20 | Immunogenic SRSF3 sequence |

Definitions

The term "subject" refers to any subject susceptible of suffering or suffering from neurological condition, a cancer of the central nervous system, a viral infection or a bacterial infection. Specifically, such a subject may be, but not limited to, human, an animal (e.g. cat, dog, cow, horse, etc.). More specifically, the subject consists of a human.

The terms "predisposed" and "suspected" refer to a subject who does not yet experience or display the pathology or symptomatology of a neurological condition, a cancer of the central nervous system, a viral infection or a bacterial infection but who may have increased probability or increased risk of developing a neurological condition, a cancer of the central nervous system, a viral infection or a bacterial infection.

The term "mRNA" or "gene transcripts" refers to pre-mRNA transcript(s), transcript processing intermediates and mature mRNA(s) ready for translation. Transcript processing may include splicing, editing and degradation.

The term "upregulated mRNA" refers to levels of mRNA encoding a specific polypeptide which are detectably increased in a sample from a subject predisposed or suspected of developing a neurological condition, a cancer of the central nervous system, a viral infection or a bacterial infection, or suffering from a neurological condition, a cancer of the central nervous system, a viral infection or a bacterial infection compared with the reference level of the mRNA encoding the same specific polypeptide in a sample from an healthy subject.

As used herein, "mRNA encoding polypeptides implicated in innate immune response" include mRNA from genes encoding polypeptides implicated in immune functions which are upregulated but untranslated following for example an LPS challenge such as SAA3, LCN2, CCL5, IRF7, CCL3, IFI44, IRGM1, GBP2, PLIN4, CP, GPR84, OASL2, IFIT1, USP18, GBP7, GM7676, CLEC7A, OLFR110, CH25H, LILRB4, GPNMB, CST7, OLFR111, CTLA2B, CD68, EIF4A2, TREM2 or APOE.

Polypeptide implicated in innate immune response include polypeptide that are upregulated but untranslated following for example an LPS challenge such as SAA3, LCN2, CCL5, IRF7, CCL3, IFI44, IRGM1, GBP2, PLIN4, CP, GPR84, OASL2, IFIT1, USP18, GBP7, GM7676, CLEC7A, OLFR110, CH25H, LILRB4, GPNMB, CST7, OLFR111, CTLA2B, CD68, EIF4A2, TREM2 or APOE. mRNA encoding polypeptides implicated in innate immune response also include Up-regulated mRNAs after LPS injection as described herein (e.g. in a mouse model as described in example 2) such as those described in table 1 below.

TABLE 2

Relative SRSF3 Binding Sites on the 3'UTR of Up-regulated mRNAs After LPS Injection

| Gene Symbol | Name | mRNA fold change | 3'UTR length (bp) | Relative SRSF3 binding sites |
|---|---|---|---|---|
| Cluster 1 | | | | |
| Saa3 | Serum amyloid A3 | 29.52 | 128 | 24 |
| Lcn2 | Lipocalin 2 | 23.71 | 224 | 32 |
| Ccl5 | Chemokine (C—C motif) ligand 5 | 15.93 | 198 | 16 |
| Irf7 | Interferon regulatory factor 7 | 7.8 | 41 | 3 |
| Ccl3 | Chemokine (C—C motif) ligand 3 | 5.19 | 428 | 29 |
| Cluster 2 | | | | |
| Ifi44 | Interferon-induced protein 44 | 7.15 | 1458 | 173 |
| Irgm1 | Immunity-related GTPase family M member 1 | 6.17 | 552 | 83 |

TABLE 2-continued

Relative SRSF3 Binding Sites on the 3'UTR of Up-regulated mRNAs After LPS Injection

| Gene Symbol | Name | mRNA fold change | 3'UTR length (bp) | Relative SRSF3 binding sites |
|---|---|---|---|---|
| Gbp2 | Guanylate binding protein 2 | 5.01 | 515 | 91 |
| Plin4 | Perilipin 4 | 4.8 | 1416 | 60 |
| Cp | Ceruloplasmin | 4.35 | 411 | 82 |
| Gpr84 | G protein-coupled receptor 84 | 3.69 | 213 | 8 |
| Oasl2 | 2'-5' oligoadenylate synthetase-like 2 | 3.69 | 878 | 166 |
| Ifit1 | Interferon-induced protein with tetratricopeptide repeats 1 | 3.42 | 1152 | 38 |
| Usp18 | Ubiquitin specific peptidase 18 | 3.21 | 400 | 17 |
| Gbp7 | Guanylate binding protein 7 | 3.04 | 3577 | 367 | mRNA encoding polypeptides implicated in innate immune response also include mRNAs shown in table 2 below.

TABLE 3 mRNA overexpressed at advance stage of disease (in ALS mouse model) implicated in microglia immune functions and not detected at proteomics analysis

| Symbol | Name | Fold Change | p-value | Number of Srsf3 binding sites at 3'UTR |
|---|---|---|---|---|
| Clec7a | C-type lectin domain family 7 member A | 38.04 | 0.024969 | 16 |
| Olfr110 | Olfactory receptor | 22.33 | 0.019223 | ? |
| Ch25h | Cholesterol 25-hydroxylase | 18.26 | 0.001887 | 11 |
| Lilrb4 | Leukocyte immunoglobulin-like receptor subfamily B membe r4 | 16.57 | 0.000155 | 41 |
| Gpnmb | Transmembrane glycoprotein NMB | 16.52 | 0.001199 | 17 |
| Cst7 | Cystatin-F | 14.16 | 0.009823 | 19 |
| Olfr111 | Olfactory receptor | 13.3 | 0.00493 | ? |
| Ctla2b | Protein CTLA-2-beta | 13.2 | 0.017815 | 8 |
| Cd68 | Macrosialin | 12.81 | 0.00005 | 5 |
| Eif4a2 | Eukaryotic initiation factor 4A-II | 12.41 | 0.02398 | 17 |
| Trem2 | Triggering receptor expressed on myeloid cells 2 | 7.4 | 0.0064 | 21 |
| Apoe | Apolipoprotein E | 1.78 | 0.04 | 6 |

The expressions "nucleic acid" or "nucleic acid sequence" refers to a sequence of nucleoside or nucleotide monomers consisting of naturally occurring bases, sugars and inter-sugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases.

The expression "3'UTR" refers to the 3'-untranslated region corresponding to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence.

The expression "3'UTR binding site" refers to a nucleic acid sequence comprised in the 3'UTR sequence of a mRNA capable of specifically associating with a polypeptide capable of binding to the sequence. The nucleic acid sequence may vary in length. A single 3'UTR sequence may comprise multiple 3'UTR binding sites.

The expression "neurological condition" refers to a condition which involves the progressive loss of structure or function of neurons. Neurological conditions include vascular dementia, frontotemporal lobar degeneration (FTD), Alzheimer, motor neuron disease (e.g. Amyotrophic Lateral Sclerosis (ALS), Progressive bulbar palsy (PBP), Primary lateral sclerosis (PLS) or Kennedy's Disease) and Parkinson's disease.

The expression cancer of the central nervous system includes astrocytoma, glioblastoma or oligodendroglioma.

The expression "viral infection" refers to an infection resulting from a virus. The infection may or may not be clinically apparent. All forms of viral infections are included within this definition including infection with HIV, dengue virus, influenza virus, EB virus, etc.

The expression "bacterial infection" refers to an infection resulting from a bacteria. The infection may or may not be clinically apparent. All forms of bacteria are included within this definition including cocci, bacilli, spirochetes, spheroplasts, protoplasts, etc. Also included within this term are prokaryotic organisms that are Gram negative or Gram positive.

The expression "polypeptide or fragments thereof" refers to peptides, oligopeptides and proteins. This term also does not exclude post-expression modification of polypeptides. For example, polypeptides that include the covalent attachment of glycosyl groups, acetyl groups, lipid groups and the like are encompassed by the term polypeptide. The term 'fragment thereof', as used herein, refers to polypeptide that may comprise for example 50%, 60%, 70%, 80%, 90%, 95% or more of the polypeptide sequence of the full-length reference polypeptide. In one aspect the fragment is a fragment that is functional (e.g. retains the activity of the complete polypeptide or polynucleotide)

SRSF3 (also known as SFRS3 or SRp20) is a protein known as Serine and arginine rich splicing factor 3 (SEQ ID NO:12). SRSF3 is well know in the art. For example, see GenBank NM_003017.4 or UniProt P84103. In one aspect, SRSF3 as used herein refers to the full length of SRSS3 or fragments thereof. In one aspect, SRSF3 comprises at least one RRM (RNA Recognition Motif) binding domain (SEQ ID NO:13). In a further aspect, SRSF3 comprises an RS (serine-arginine dipeptide repeat) domain (SEQ ID NO:14). In one aspect, SRSF3 comprises at least one RRM (RNA Recognition Motif) binding domain (SEQ ID NO:13) at least one RS (serine-arginine dipeptide repeat) domain (SEQ ID NO:14). In one aspect SRSF3 is phosphorylated.

In a further aspect, SRSF3 comprises the native sequence of the SRSF3 protein of GenBank NM_003017.4 or UniProt P84103 or functional fragments thereof. In one embodiment, the SRSF3 polypeptide comprises a sequence at least 65% to 95% identical, at least 65%, 70%, 75%, 80%, 85%, 90% identical or at least 95% identical to part or all of the sequence shown in SEQ ID NO:12, GenBank NM_003017.4 or UniProt P84103.

In one embodiment, a SRSF3 polynucleotide includes a sequence coding for a SRSF3 polypeptide as defined herein.

In one embodiment, SRSF3 polynucleotide comprises a polynucleotide at least 65% to 95% identical, at least 65%, 70%, 75%, 80%, 85%, 90% identical or at least 95% identical to part or all of the sequence shown in GenBank NM_003017.4 or UniProt P84103 or fragments thereof.

The expression "phosphorylated SRSF3" as used herein, refers to all forms of SFSR3 that have been post translationally modified by phosphorylation. In particular, it refers to SRSF3 where the hydroxy groups of the side chains of threonine, serine, hydroproline, hydroxylysine, tyrosine, and/or any other non-natural hydroxy amino acid is esterified with a phosphate group. SRSF3 comprises at least one phosphorylation site. The term "phosphorylation site" refers to an amino acid or amino acid sequence which is recognized by a kinase or phosphatase for the purpose of phosphorylation or dephosphorylation, respectively.

The expression "SRSF3 agent" refers to an agent capable of modifying SRSF3 function or expression. In one aspect, a SRSF3 agent can inhibit SRSF3 translation repression activity. In a further aspect, the agent can inhibit SRSF3 ability to bind to the 3'UTR of at least one mRNA coding for a polypeptide implicated in an innate immune response. By modifying SRSF3 translation repression activity, the SRSF3 agent may restore mRNA translation completely or in part and may in turn result in an increased translation of at least one mRNA coding for a polypeptide implicated in an innate immune response.

"SRSF3 agent" includes SRSF3 agent which can inhibit expression or function of SRSF3. In one aspect, the SRSF3 agent inhibits the activity or function of a SRSF3 which is phosphorylated. In a further aspect, the SRSF3 agent is a SRSF3 specific antibody (e.g, a monoclonal antibody, a single chain antibody (a single chain variant fragment), a humanized antibody, and/or an antibody that is specific for phosphorylated SRSF3), a nucleic acid (e.g. an antisense, an interfering RNA molecule, an siRNA, or an miRNA) a polypeptide, a low molecular weight compound or a gene editing system.

In a further aspect, the gene editing system includes a CRISPR system, a zinc finger nuclease system (ZFN), or a transcription activator-like effector nuclease system (TALENs). In one aspect, the SRSF3 agent increases the translation of at least one mRNA coding for a polypeptide implicated in an innate immune response. In a further aspect, the SRSF3 agent inhibits the binding between SRSF3 (e.g. at least one RRM site) and at least one mRNA (e.g. at least one 3'UTR SRSF3 binding site) coding for a polypeptide implicated in an innate immune response.

The expression "CRISPR system" refers to an endonuclease in combination with an RNA guide strand. The endonuclease may be, but is not limited to, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, CasX or CasY.

The expression "guide RNA" (also referred to herein as "DNA-targeting RNA") refers to a RNA molecule or a group of RNA molecules that can bind to a nuclease (such as Cas9 or its nuclease variant) and target the nuclease to a specific location within a target DNA. A guide RNA comprises two segments, a "DNA-targeting segment" and a "protein-binding segment." These two segments can be on the same RNA molecule or on two or more separate RNA molecules. The DNA-targeting segment comprises a nucleotide sequence that is complementary to a specific sequence within a strand of a target DNA (i.e., the complementary strand of the target DNA). The protein-binding segment interacts with a nuclease, such as a Cas9 or Cas9 related polypeptide. As mentioned above, in the case of Cas9, site-specific cleavage of the target DNA occurs at locations determined by both (i) base-pairing complementarity between the DNA-targeting segment and the target DNA; and (ii) a short motif referred to as the PAM sequence in the target DNA. Guide RNAs may include modified bases or backbone.

The expression "inhibit the binding" refers to the ability of an agent to prevent or disrupt the capacity of SRSF3 to specifically enter in physical contact with a specific nucleic acid sequence. Inhibition may occur by inducement of conformational changes in the secondary or tertiary structure of SRSF3, obstruction of the binding domains of SRSF3 and/or binding sites on a nucleic acid sequence, prevention of SRSF3 phosphorylation, dephosphorylation of SRSF3, proteolysis of SRSF3, competitional binding, alternative splicing of SRSF3 pre-mRNA, prevention of SRSF3 mRNA translation, mutation of the SRSF3 gene, deletion of the SRSF3 gene from the genome of a cell, or any other mechanism which inhibits the capacity of SRSF3 to specifically associate with a specific nucleic acid sequence.

The expression "increased level of polypeptide" refers to the level of polypeptide (e.g. an upregulated but untranslated polypeptide) translated from a mRNA detectably increased in a sample relative to a control. The sample can be from a subject that was treated with a SRSF3 agent. The control can be the reference level of polypeptide translated from the same mRNA in an untreated subject.

The expressions "SRSF3-specific antibody" and "phosphorylated SRSF3-specific antibody" refer to antibodies that bind to one or more epitopes of SRSF3 or a phosphorylated version of SRSF3 respectively, but which do not substantially recognize and bind to other molecules in a sample containing a mixed population of antigenic molecules. In one embodiment, a SRSF3-specific antibody recognizes a region of SRSF3 comprising at least a part of the RRM domain (SEQ ID NO:13) of SRSF3, while a phosphorylated SRSF3-specific antibody recognizes a region of SRSF3 comprising at least the SRSF3 phosphorylation site and at least a part of the RS domain of SRSF3 (SEQ ID NO:14).

The term "siRNA" refers to small inhibitory RNA duplexes whose presence within a cell results in RNA interference and leads to reduced expression of a transcript to which the siRNA is targeted. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

The expression "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. This expression includes oligonucleotides composed of naturally-occurring nucleobases, sugars and covalent internucleoside (backbone) linkages as well as oligonucleotides having non-naturally-occurring portions which function similarly. Such modified or substituted oligonucleotides may be preferred over native forms because of desirable properties such as, for example, enhanced cellular uptake, enhanced affinity for nucleic acid target and increased stability in the presence of nucleases.

Antisense according to the present description are complementary to a target sequence of a target nucleic acid which encodes mammalian SRSF3. The term "target sequence" as used herein refers to a sequence of nucleotides present in the target nucleic acid which comprises a nucleic acid sequence which is complementary to the antisense according to the present description. In some embodiments, the target sequence consists of a region on the target nucleic acid which is complementary to the contiguous nucleotide sequence of the antisense according to the present description. In some embodiments the target sequence is longer than the complementary sequence of a single oligonucleotide, and may, for example represent a preferred region of the target nucleic acid which may be targeted by several antisense according to the present description.

According to a first aspect, the antisense inhibits the translation of the mRNA coding for SRSF3. According to another aspect, the antisense targets the 5'UTR ("Untranslated Transcribed Region") of SRSF3, i.e. the portion of mRNA located upstream of the start codon (ATG) or overlapping said start codon. By binding to this region, the antisense will interfere with transcription and/or translation and therefore at least partially inactivate the SRSF3 gene. In a further aspect, the antisense targets the region comprising the 100 nucleotides located upstream of the ATG. In a further aspect, the antisense targets the region located between positions +1 and +25 with reference to the ATG.

The expression "low molecular weight compound" includes any chemical or other moiety, other than polypeptides and nucleic acids, that can act to affect biological activity of SRSF3. Small molecules can include any number of therapeutic agents presently known and used, or can be small molecules synthesized in a library of such molecules for the purpose of screening for biological function(s).

The expression "myeloid cell" refers to myeloid lineage cells including, but not limited to monocyte, macrophage and microglial cells.

The expression "monocyte" refers to a type of white blood cell involved in first-line defensive mechanism and is recognized as able to differentiate into a dendritic cell or macrophage precursor. Monocytes normally move in the blood system. In response to external stimulating signals, monocytes secrete many immuno-regulatory cytokines, move to the site of infection in the tissues and differentiate into macrophages.

The expressions "microglial cell" or "microglia" refers to a class of glial cells involved in the mediation of an immune response within the central nervous system. Microglial cells are capable of producing exosomes, and further include different forms of microglial cells, including amoeboid microglial cells, ramified microglial cells and reactive, or "activated", microglial cells. Microglial cells include reactive microglia, which are defined as quiescent ramified microglia that transform into a reactive, "activated", macrophage-like state and accumulate at sites of brain injury and inflammation to engage in immune functions and assist in tissue repair and neural regeneration (Kreutzberg, 1996). Microglia immune activity is restrained by dedicated immune inhibitory pathways that suppress unwanted inflammatory responses and tissue destruction that are often associated with immune activation. Microglial often acquire a stable phenotype essential for the brain protection and homeostasis.

The term "phenotype" generally refers to any observable character of a cell or organism.

The expression "innate immune response" refers to a variety of innate resistance mechanisms by which a cell or individual recognizes and responds to the presence of a pathogen and/or injury. As used herein, an "innate immune response" includes the intracellular and intercellular events and reactions that occur when a cell recognizes injury and/or pathogen associated molecular patterns or signals. Microglial cells may exhibit innate immune response once activated.

The expression "myeloid regulation" refers to the modification, or the prevention of a modification, to the phenotype of a myeloid cell through the action of a SRSF3 agent. For example, in the context of a neurological condition, cancer, bacterial or a viral infection, the SRSF3 agent may increase the level of a polypeptide translated from an upregulated mRNA implicated in the immune response of a myeloid cell, thus modifying its phenotype from a first phenotype (e.g. aberrant) to a second phenotype (e.g. immune).

The expression "microglial cell regulation" refers to the modification, or the prevention of a modification, to the phenotype of a microglial cell through the action of a SRSF3 agent. For example, in the context of a neurological condition, cancer, bacterial or a viral infection, the SRSF3 agent may increase the level of a polypeptide translated from an upregulated mRNA implicated in the immune response of a microglial cell, thus modifying its phenotype from a first phenotype (e.g. aberrant) to a second phenotype (e.g. immune.) Furthermore, microglial cell regulation may prevent the development of an aberrant phenotype at the beginning of the development of a neurological condition, for example. In one embodiment, a microglial cell exhibiting an aberrant phenotype refers to a microglial cell unable to generate an effective innate immune response in the context of a neurological condition, cancer, bacterial or a viral infection. In one embodiment, a microglial cell exhibiting an immune phenotype refers to a microglial cell able to generate innate immune response functions such as, but not limited to, phagocytosis.

The term "sample" refers to a variety of sample types obtained from a subject and can be used in a diagnostic assay. The definition encompasses blood, urine, cerebrospinal fluid and other liquid samples of biological origin. The definition also encompasses solid tissue samples such as a biopsy of specimen or tissue culture or cells derived therefrom such as cortical neurons, microglial cells, myeloid cells or spinal cord extract.

The expression "candidate compound" includes compounds such as small molecules, nucleic acids, antibodies or polypeptides capable of interacting with a biological target molecule, in particular with a protein, in such a way as to modify the biological activity thereof. In one embodiment, a candidate compound is a SRSF3 agent.

The expression "biological system" refers to a suitable biological assay or biological model. In one aspect, the biological assay can be an in vitro assay wherein the interaction between SRSF3 (or a RRM binding site) and the mRNA (or its 3' UTR) is measured, or the activity or expression of SRSF3 is measured. The biological model can be any suitable model allowing the evaluation of the interaction between SRSF3 (or a RRM binding site) and the mRNA (or its 3' UTR), or the evaluation of the activity or expression of SRSF3. The model can be an organism that has been modified in order to over-express SRSF3.

It is noted that the present description is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers.

The expression "pharmaceutically acceptable salts" refers to those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune p sulphonic, tartaric, acetic, trifluoroacetic, citric, methanesulphonic, formic, benzoic, malonic, naphthalene 2 sulphonic and benzenesulphonic acids. Salts derived from amino acids are also included (e.g. L-arginine, L-Lysine). Salts derived from appropriate bases include alkali metals (e.g. sodium, lithium, potassium) and alkaline earth metals (e.g. calcium, magnesium).

With regards to pharmaceutically acceptable salts, see also the list of FDA approved commercially marketed salts listed in Table I of Berge et al., Pharmaceutical Salts, J. of Phar. Sci., vol. 66, no. 1, January 1977, pp. 1-19.

It will be appreciated by those skilled in the art that compounds can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will be appreciated that the amount of compounds required for use in treatment will vary not only with the particular compound selected but also with the route of administration, the nature of the condition for which treatment is required and the age and condition of the patient and will be ultimately at the discretion of the attendant physician.

The desired dose may conveniently be presented in a single dose or as divided dose administered at appropriate intervals, for example as two, three, four or more doses per day. While it is possible that, for use in therapy, the compounds may be administered as the raw chemical it is preferable to present the active ingredient as a pharmaceutical composition. The description thus further provides a pharmaceutical combination or composition of the compounds as described herein or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, intra-nasal, mucosal, topical (including buccal and sub-lingual), transdermal, vaginal or parenteral (including intramuscular, sub-cutaneous and intravenous) administration or in a form suitable for administration by inhalation or insufflation. The compositions may, where appropriate, be conveniently presented in discrete dosage units and may be prepared by any of the methods well known in the art of pharmacy. All methods include the step of bringing into association the active with liquid carriers or finely divided solid carriers or both and then, if necessary, shaping the product into the desired composition.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds or combinations may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds or combinations are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds or combinations may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

As used herein, the expression "an acceptable carrier" means a vehicle for the combinations and compounds described herein that can be administered to a subject without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

It will be appreciated that the amount of a compound required for use in treatment will vary not only with the particular compound selected but also with the route of administration, the nature of the condition for which treatment is required and the age and condition of the patient and will be ultimately at the discretion of the attendant physician. In general however a suitable dose will be in the range of from about 0.001 to about 100 mg/kg of body weight per day, for example, in the range of 0.01 to 50 mg/kg/day, or, for example, in the range of 0.1 to 40 mg/kg/day. The compound is conveniently administered in unit dosage form; for example containing 1 to 2000 mg, 10 to 1500 mg, conveniently 20 to 1000 mg, most conveniently 50 to 700 mg of active ingredient per unit dosage form.

In another embodiment of the present description, dosages may be estimated based on the results of experimental models, optionally in combination with the results of assays of the present description. Generally, daily oral doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition.

The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the preferred methods and materials are described. The issued patents, published patent applications, and references that are cited herein are hereby incorporated by reference to the same extent as if each was specifically and individually indicated to be incorporated by reference. In the case of inconsistencies, the present disclosure will prevail.

EXAMPLES

Example 1

Generation and Characterization of the CD11brGFP Transgenic Mice

Figure 1:
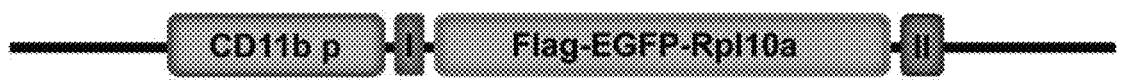
FIG. 1 Characterization of the CD11brGFP Transgenic Mice. (A) Schematic representation of Flag/EGFP tagged murine Rpl10a construction under control of the CD11b promoter, I: Intervening sequence (IVS); II: SV40 polyA (SEQ ID NO:1). (B) Visualization of the transgene by PCR using oligonucleotides that amplify 329 bp of the EGFP gene only from transgenic mice (Tg) and not WT. (C) Schematic representation of coronal brain section. The red rectangle locates the region where the pictures have been done in (D) and (E). (D and E) EGFP expression in brain sections in control (D) or 24 hrs after LPS injection mice (E). GFP immunostaining co-localized with CD11b (blue) and Ibal (red). (F) Western blot after immunoprecipitation of microglia primary culture lysates demonstrate the immuno-binding of the Flag/EGFP-Rpl10a transgene by the Flag beads. Scale bars, 25 and 50 μm.
Figure 1:
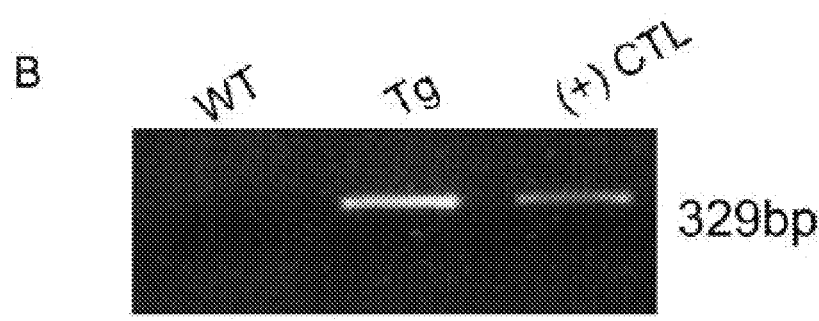
Figure 1:
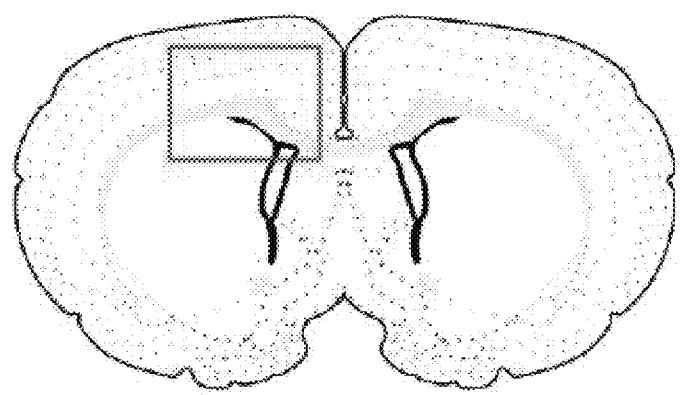
Figure 1:
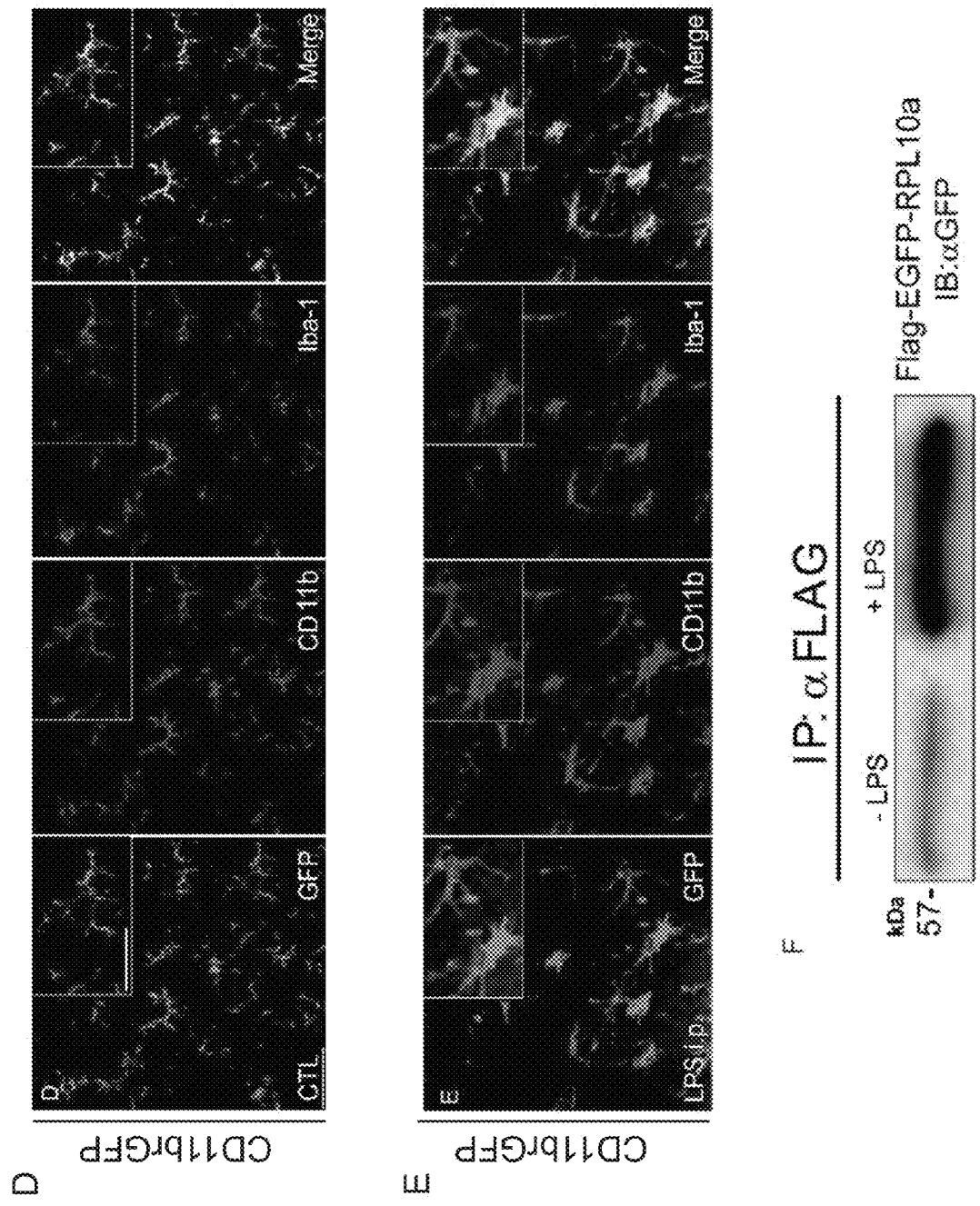

To identify the cell-type specific mRNA and protein profiles in vivo from the microglial cells, a transgenic mouse model expressing Flag-EGFP fused to the N-terminus of the large subunit ribosomal protein L10a (Flag-EGFP-RPL10a) under transcriptional control of the human CD11b promoter (FIGS. 1 A and 1 B) was created (SEQ ID NO:1). In previous work, the human CD11b promoter has been shown to efficiently drive the microglial transgene expression (Gowing et al., 2006; Lalancette-Hebert et al., 2007). The transgenic mice are viable and do not develop overt phenotypes. In the present experiments, a mouse line called CD11brGFP exhibiting the appropriate microglia-specific transgene expression was selected. To confirm that expression of the Flag/EGFP-RPL10a (F/EGFP-L10a) transgene was indeed restricted to microglial cells, double immunofluorescence analysis for EGFP and CD11b/Iba1, two commonly used microglial markers, was performed. As shown in FIGS. 1 C to 1 E, the double immunofluorescence analysis revealed that in brain tissue the CD11b driven transgene (GFP staining) co-localizes with the endogenous CD11b and Iba1 immunostaining in baseline conditions and following LPS stimuli. As previously reported (Gravel et al., 2016; Lalancette-Hebert et al., 2009), the systemic LPS injection induces a marked change in microglial morphology and increases expression of the GFP fluorescence (FIG. 1 E). As an additional proof-of-concept control, microglial ribosomes from the CD11brGFP primary microglia culture using a Flag epitope were selectively immunoprecipitated (IP). As shown in FIG. 1 F, western blot analysis confirmed the immunobinding of the F/EGFP-L10a transgene by the Flag beads, thus further validating the transgenic model-system.

Example 2

Figure 2:
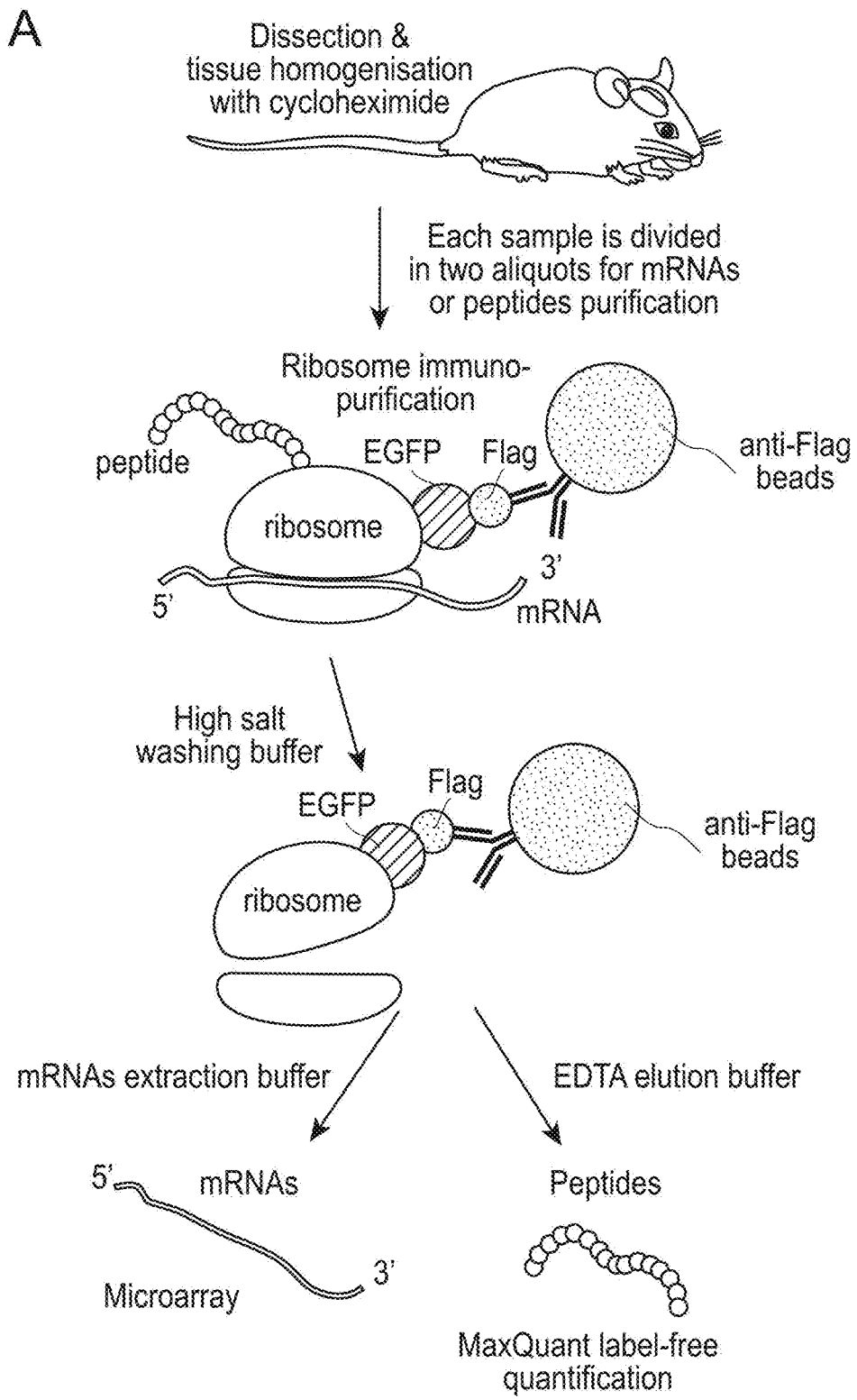
FIG. 2 Highly Upregulated Immune Genes are Not Translated. (A) Schematic representation of the ribosome affinity purification method from transgenic mice brains. (B) Heat map and hierarchical clustering of microglia analyzed with the Affymetrix 2.0 ST chip. Experiments are conducted in three biological replicates (n=5 mice/condition). (C) Differences between transcriptomic and proteomic data analysis. All up-regulated immune genes presented in the cluster 1 (zoom1) and cluster 2 (zoom2) were not observed in the sequenced peptides list (the table only shows cluster 1). Cap2 and Ywhaz are used as control. (D) Validation of proteomic results by immunoblots after polysomes immunoprecipitation. CAP2 and actin were used as internal control. Whole-brain extracts were used as input. (E) Quantitative western blot analysis from the whole brain extract of mice treated or not with LPS. (Data are mean±SEM; n=3; SAA3: p=0.3224; LCN2: *p=0.0297; CCL5: p=0.3709; CAP2: p=0.8280).
Figure 2:
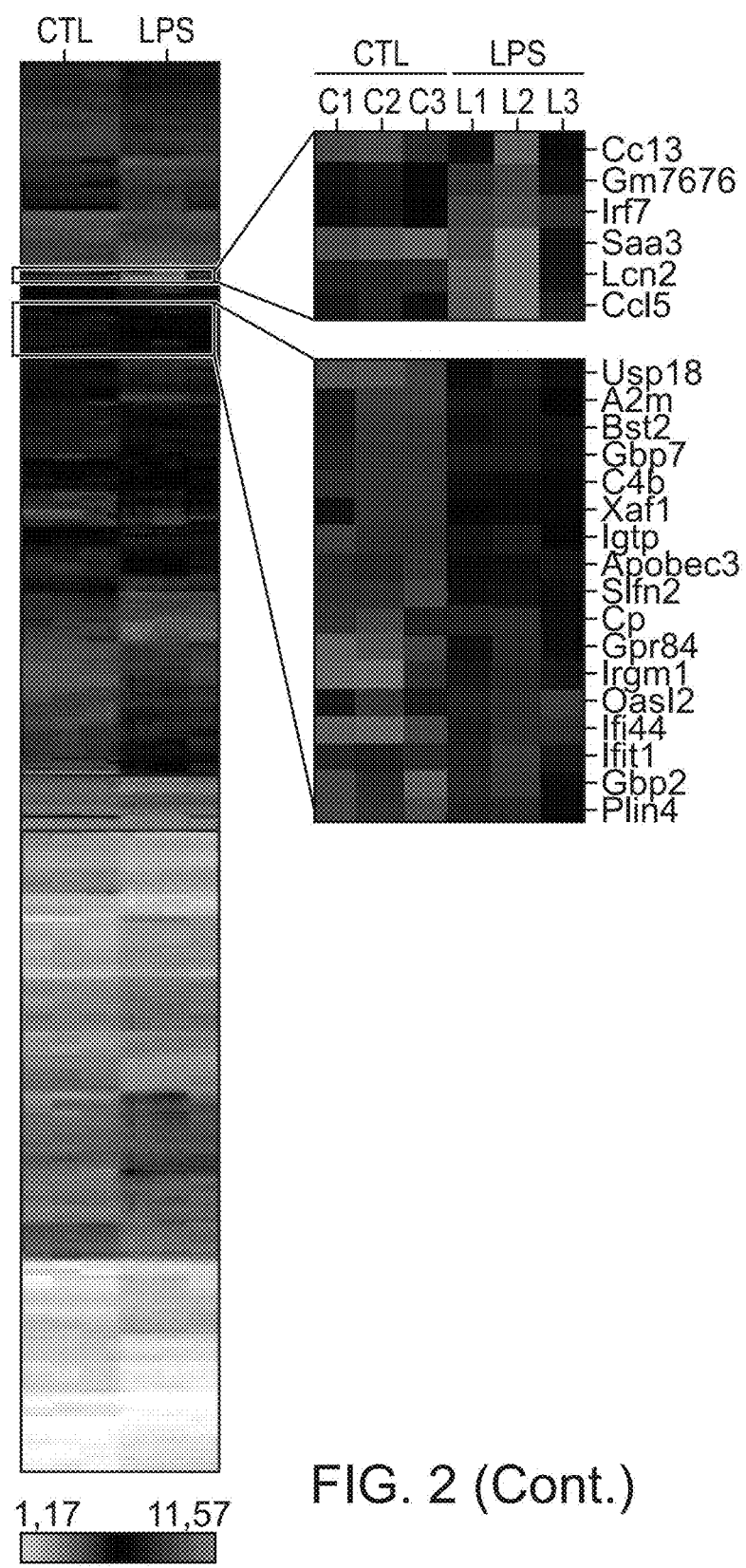
Figure 2:
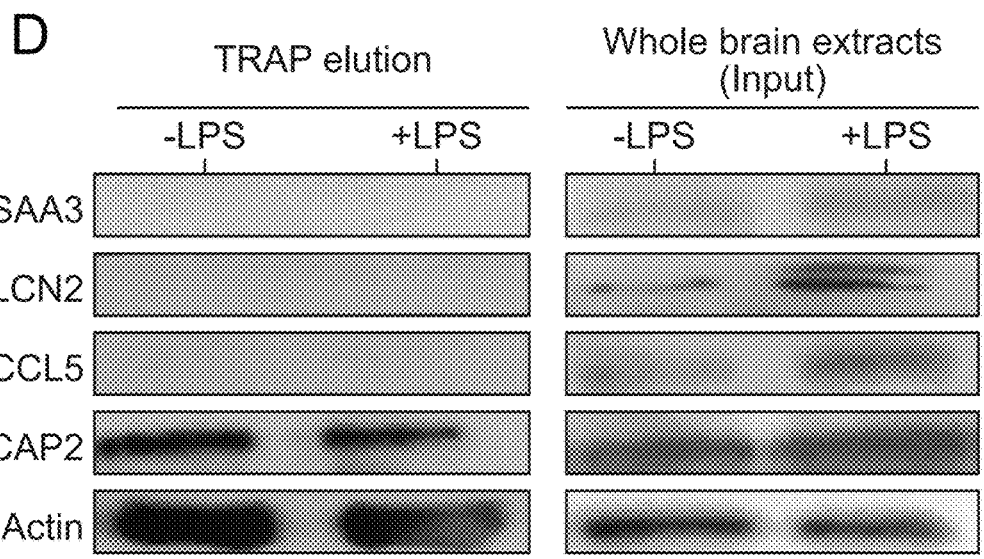
Figure 2:
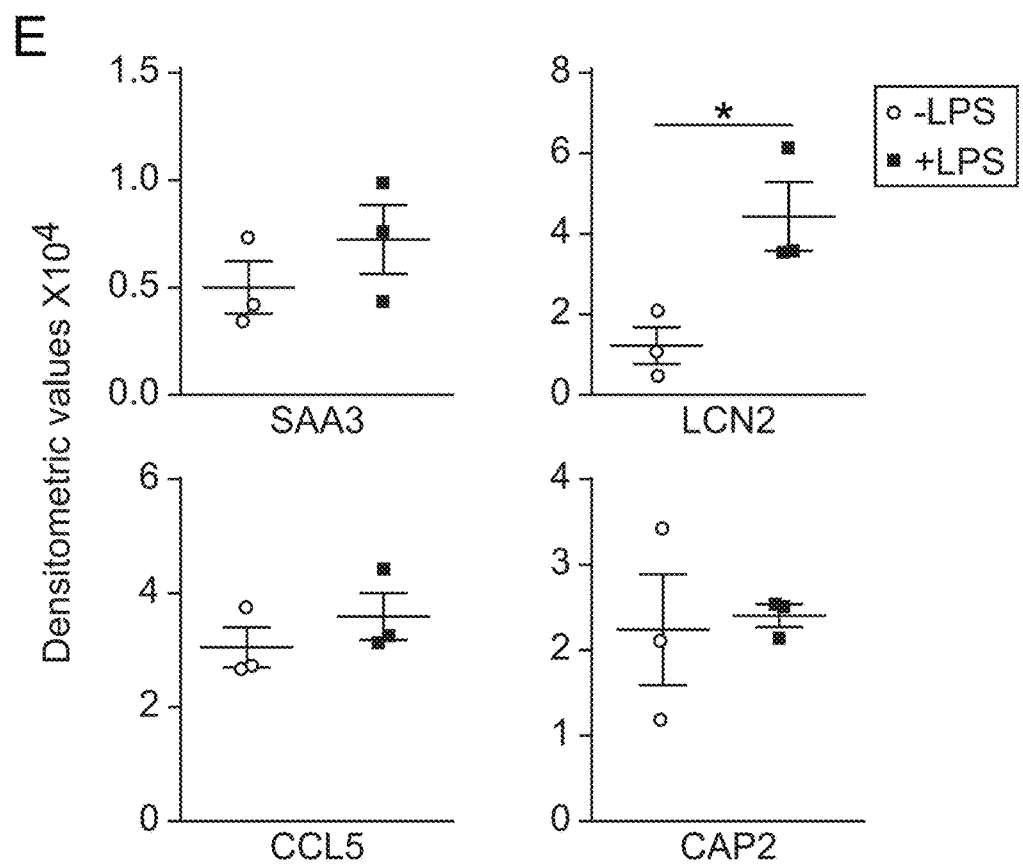

Translational Profiling of Activated Microglia Reveals a Cluster of the Highly Regulated Innate Immune Genes To date, a variety of regulatory mechanisms involved in the tight transcriptional and posttrancriptional control of the immune genes have been proposed (for review (Anderson, 2010; Carpenter and Fitzgerald, 2015; Carpenter et al., 2014)). However, in vivo mechanisms remain elusive. To assess the molecular signatures of microglial activation in vivo, the CD11brGFP mouse model and modified Translational Affinity Purification (TRAP) approach were taken advantage of by performing parallel transcriptome and proteome analysis in the baseline conditions and following an acute innate immune challenge. As experimental paradigm, a standard LPS challenge (Laflamme et al., 2001; Lalancette-Hebert et al., 2009) was used. Importantly, the systemic LPS does not lead to infiltration of the peripheral cells, thus innate immune response is mediated by the CD11b positive resident microglia (Chen et al., 2012). It was previously demonstrated that systemic (i.p.) injection of LPS induces a wave of resident microglial activation peaking 24 hrs after injection (Lalancette-Hebert et al., 2009), thus at 24 hrs after LPS the brain tissue homogenates were immunoprecipitated using an anti-Flag agarose affinity resin and the polyribosome complexes were used either for i) mRNA extraction followed by Affymetrix Mouse Genome 430 analysis or ii) peptide extraction followed by a high resolution label-free proteomic analysis. The experimental strategy is schematically presented in FIG. 2 A. Statistical analyses revealed that LPS significantly altered the expression of 661 transcripts compared to control. Of these, 394 genes were up-regulated whereas 267 genes were down-regulated (1.2-fold difference or greater). For data visualization, hierarchical clusters were constructed with statistically significant ($p<0.05$) genes (FIG. 2 B). Based on the clustering, two clusters (FIG. 2 B: zoom1 and zoom2) were observed in which the LPS condition includes the most up-regulated transcripts markedly dissociated from control. Furthermore, the majority of those transcripts were classified as being involved in the immune response. Consistent with previous work (Madeddu et al., 2015) the most highly up-regulated transcripts were: serum amyloid gene (Saa3), (29.52 fold change) and lipocalin 2 (Lcn2)(23.71 fold change). Both genes are linked to the acute phase immune response to infection (Flo et al., 2004; O'Brien and Chait, 2006). The third most up-regulated transcript was chemokine (C-C motif) ligand 5 (Ccl5/Rantes, 15.93 fold increase). RANTES is a member of the C-C subfamily of chemokines implicated in a number of chronic inflammatory and autoimmune processes (Danoff et al., 1994). Table 4 summarizes the top 50 up-regulated transcripts.

TABLE 4

Top50 of Up-Regulated Transcripts

| Transcript Cluster ID | Gene Symbol | Description | LPS Bi-weight Avg Signal (log2) | CTL Bi-weight Avg Signal (log2) | Fold Change (linear) (LPS vs. CTL) | ANOVA p-value (LPS vs. CTL) | FDR p-value (LPS vs. CTL) |
|---|---|---|---|---|---|---|---|
| 17491193 | Saa3 | serum amyloid A 3 | 9.26 | 4.38 | 29.52 | 0.009823 | 0.999886 |
| 17383892 | Lcn2 | lipocalin 2 | 9.98 | 5.41 | 23.71 | 0.020288 | 0.999886 |
| 17266946 | Ccl5 | chemokine (C—C motif) ligand 5 | 9.7 | 5.71 | 15.93 | 0.012908 | 0.999886 |
| 17497813 | Irf7 | interferon regulatory factor 7 | 9.02 | 6.06 | 7.8 | 0.002712 | 0.999886 |
| 17497718 | Ifitm3 | interferon induced transmembrane protein 3 | 10.25 | 7.36 | 7.39 | 0.015107 | 0.999886 |

TABLE 4-continued

Top50 of Up-Regulated Transcripts

| Transcript Cluster ID | Gene Symbol | Description | LPS Bi-weight Avg Signal (log2) | CTL Bi-weight Avg Signal (log2) | Fold Change (linear) (LPS vs. CTL) | ANOVA p-value (LPS vs. CTL) | FDR p-value (LPS vs. CTL) |
|---|---|---|---|---|---|---|---|
| 17411147 | Ifi44 | interferon-induced protein 44 | 7.69 | 4.85 | 7.15 | 0.000323 | 0.999886 |
| 17262202 | Irgm1 | immunity-related GTPase family M | 7.2 | 4.57 | 6.17 | 0.033453 | 0.999886 |
| 17278328 | Serpina3n | serine (or cysteine) peptidase inhibitor, clade A, member 3N | 10.49 | 7.96 | 5.77 | 0.004401 | 0.999886 |
| 17266967 | Ccl3 | chemokine (C—C motif) ligand 3 | 6.97 | 4.59 | 5.19 | 0.043495 | 0.999886 |
| 17335467 | Cdkn1a | cyclin-dependent kinase inhibitor 1A (P21) | 10.22 | 7.9 | 5.01 | 0.031101 | 0.999886 |
| 17403268 | Gbp2 | guanylate binding protein 2 | 7.51 | 5.19 | 5.01 | 0.006397 | 0.999886 |
| 17499394 | Gm7676 | predicted gene 7676 | 8.34 | 6.03 | 4.95 | 0.033008 | 0.999886 |
| 17346125 | Plin4 | perilipin 4 | 7.53 | 5.27 | 4.8 | 0.003028 | 0.999886 |
| 17396260 | Cp | ceruloplasmin | 7.51 | 5.39 | 4.35 | 0.029458 | 0.999886 |
| 17362973 | Ms4a6d | membrane-spanning 4-domains, subfamily A, member 6D | 6.29 | 4.23 | 4.19 | 0.002525 | 0.999886 |
| 17254059 | Ccl12 | chemokine (C—C motif) ligand 12; c-C motif chemokine 12-like | 6.13 | 4.23 | 3.75 | 0.005152 | 0.999886 |
| 17322355 | Gpr84 | G protein-coupled receptor 84 | 6.89 | 5 | 3.69 | 0.012957 | 0.999886 |
| 17441037 | Oasl2 | 2'-5' oligoadenylate synthetase-like 2 | 7.67 | 5.79 | 3.69 | 0.001239 | 0.999886 |
| 17358832 | Ifit1 | interferon-induced protein with tetratricopeptide repeats 1 | 7.42 | 5.65 | 3.42 | 0.002767 | 0.999886 |
| 17462492 | A2m | alpha-2-macroglobulin | 7.07 | 5.33 | 3.34 | 0.011525 | 0.999886 |
| 17230045 | Ifi204 | interferon activated gene 204 | 3.99 | 2.3 | 3.21 | 0.012104 | 0.999886 |
| 17462437 | Usp18 | ubiquitin specific peptidase 18 | 6.76 | 5.08 | 3.21 | 0.006077 | 0.999886 |
| 17450501 | Gbp10 | guanylate-binding protein 10 | 8.07 | 6.43 | 3.11 | 0.014126 | 0.999886 |
| 17403224 | Gbp7 | guanylate binding protein 7 | 7.16 | 5.55 | 3.04 | 0.000506 | 0.999886 |
| 17329759 | Apod | apolipoprotein D | 10.87 | 9.36 | 2.83 | 0.010331 | 0.999886 |
| 17324446 | Rtp4 | receptor transporter protein 4 | 8.07 | 6.57 | 2.81 | 0.000303 | 0.999886 |
| 17510345 | Bst2 | bone marrow stromal cell antigen | 6.87 | 5.4 | 2.77 | 0.001195 | 0.999886 |
| 17403205 | Gbp5 | guanylate binding protein 5 | 5.12 | 3.66 | 2.75 | 0.043254 | 0.999886 |
| 17219662 | Pyhin1 | pyrin and HIN domain family member 1 | 4.34 | 2.92 | 2.68 | 0.007792 | 0.999886 |
| 17249980 | Igtp | interferon gamma induced GTPase | 6.98 | 5.58 | 2.64 | 0.01158 | 0.999886 |
| 17272785 | Lgals3bp | lectin, galactoside-binding, soluble, 3 binding protein | 8.41 | 7.01 | 2.64 | 0.012358 | 0.999886 |
| 17434023 | Isg15 | ISG15 ubiquitin-like modifier | 6.17 | 4.78 | 2.63 | 0.001235 | 0.999886 |
| 17254166 | Slfn2 | schlafen 2 | 6.92 | 5.54 | 2.6 | 0.010334 | 0.999886 |
| 17249977 | Gm12250 | predicted gene 12250 | 5.79 | 4.43 | 2.57 | 0.008446 | 0.999886 |
| 17549822 | Apod | apolipoprotein D | 8.5 | 7.23 | 2.42 | 0.00267 | 0.999886 |
| 17354589 | Gm4841 | predicted gene 4841 | 5.18 | 3.92 | 2.4 | 0.001244 | 0.999886 |
| 17343918 | C4b | complement component 4B (Chido blood group); complement C4-B-like | 6.75 | 5.53 | 2.33 | 0.000324 | 0.999886 |
| 17549820 | Apod | apolipoprotein D | 8.68 | 7.47 | 2.32 | 0.002208 | 0.999886 |
| 17313050 | Apobec3 | apolipoprotein B mRNA editing enzyme, catalytic polypeptide 3 | 6.79 | 5.59 | 2.3 | 0.028469 | 0.999886 |
| 17270354 | Gfap | glial fibrillary acidic protein | 9.78 | 8.59 | 2.28 | 0.026052 | 0.999886 |
| 17477331 | Klk1b27 | kallikrein 1-related peptidase b27 | 3.78 | 2.6 | 2.27 | 0.004312 | 0.999886 |
| 17398912 | Gm19439 | predicted gene, 19439 | 7.24 | 6.07 | 2.24 | 0.010813 | 0.999886 |
| 17407363 | S100a9 | S100 calcium binding protein A9 (calgranulin B) | 5.19 | 4.03 | 2.22 | 0.013183 | 0.999886 |
| 17252341 | Xaf1 | XIAP associated factor 1 | 6.64 | 5.51 | 2.19 | 0.003502 | 0.999886 |
| 17342868 | LOC100862287 | uncharacterized LOC100862287; FK506 binding protein 5 | 7.85 | 6.72 | 2.18 | 0.033627 | 0.999886 |
| 17510200 | Arrdc2 | arrestin domain containing 2 | 8.2 | 7.08 | 2.18 | 0.035516 | 0.999886 |
| 17259078 | Rnf213 | ring finger protein 213 | 6.93 | 5.81 | 2.17 | 0.000476 | 0.999886 |
| 17300591 | Irf9 | interferon regulatory factor 9 | 7.54 | 6.45 | 2.13 | 0.000105 | 0.999886 |
| 17232055 | Sgk1 | serum/glucocorticoid regulated kinase 1 | 9 | 7.95 | 2.06 | 0.009125 | 0.999886 |
| 17241032 | Ddit4 | DNA-damage-inducible transcript 4 | 9.09 | 8.05 | 2.06 | 0.025703 | 0.999886 |
| 17387940 | Olfr1238 | olfactory receptor 1238 | 3.25 | 2.22 | 2.04 | 0.011708 | 0.999886 |

Example 3

The Highly Up-Regulated LPS Transcripts are not Translated

Figure 7:
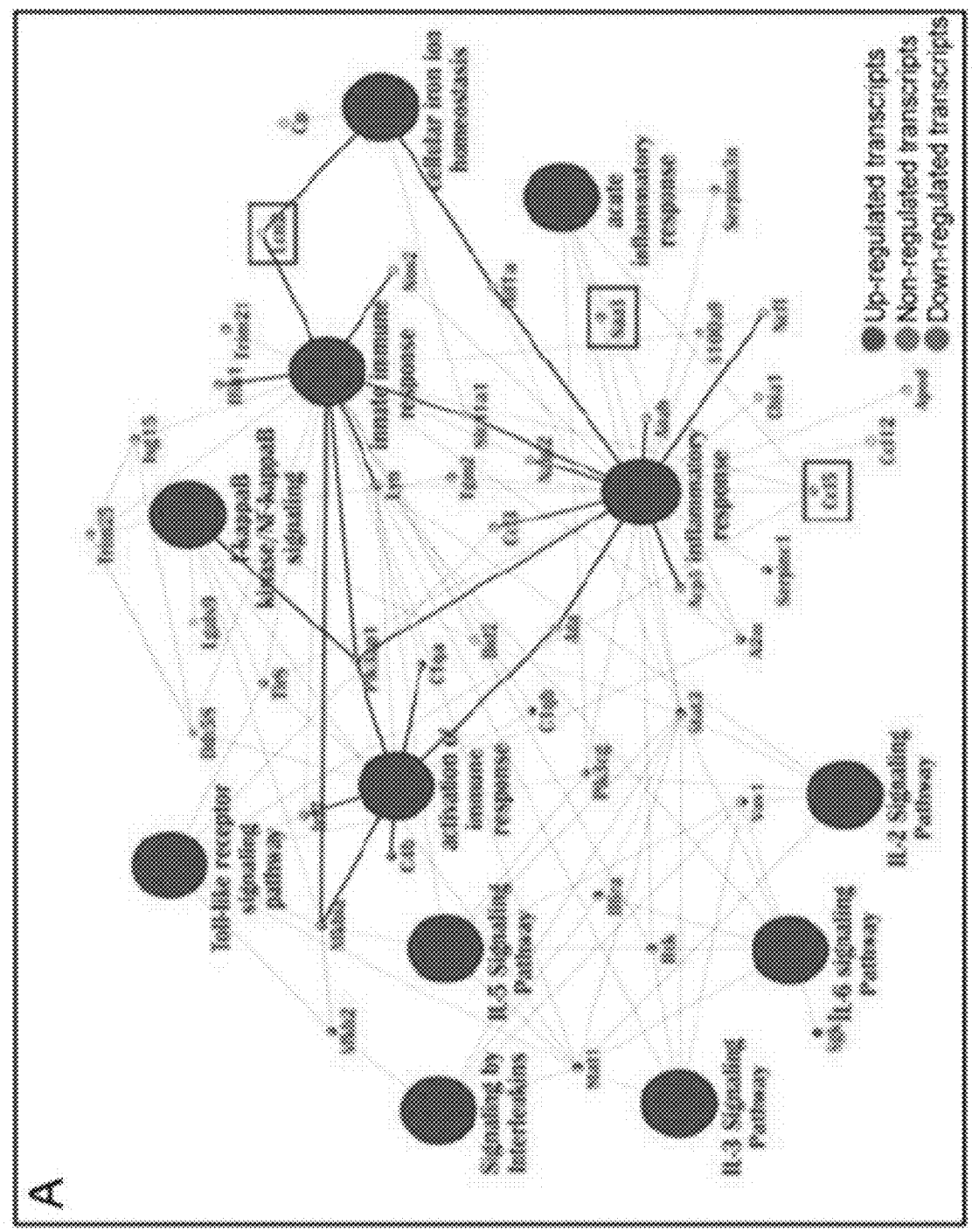
FIG. 7 Highly Up-regulated mRNAs and Un-regulated Proteins in the Microglial NF-kB Network After LPS Challenge. Terms related to Inflammation and Immune response visualized by ClueGo after LPS injection. (A) In mRNA analysis, all terms related to inflammation and immune response are up-regulated terms and are shown in red. The majority of the Top 50 of up-regulated transcripts is associated with those terms. Inflammation and immune response network was lightened for better visualization; Un-regulated transcripts are not shown. Top 3 of up-regulated mRNA (highlighted by red rectangles) were used for further validation. (B) In proteomic analysis, all terms related to inflammation and immune response appears in gray because the majority of the peptides associated to these terms are not regulated. Only four proteins related to inflammation and immune response terms are regulated: Ppm1b and Elmo2 are up-regulated and Hsp90ab1 and Fbxw11 are down-regulated. All up-regulated transcripts related to inflammation and immune response are not detected by proteomic analysis. In both panels, the size of the nodes reflected the number of genes/term vs cluster.
Figure 7:
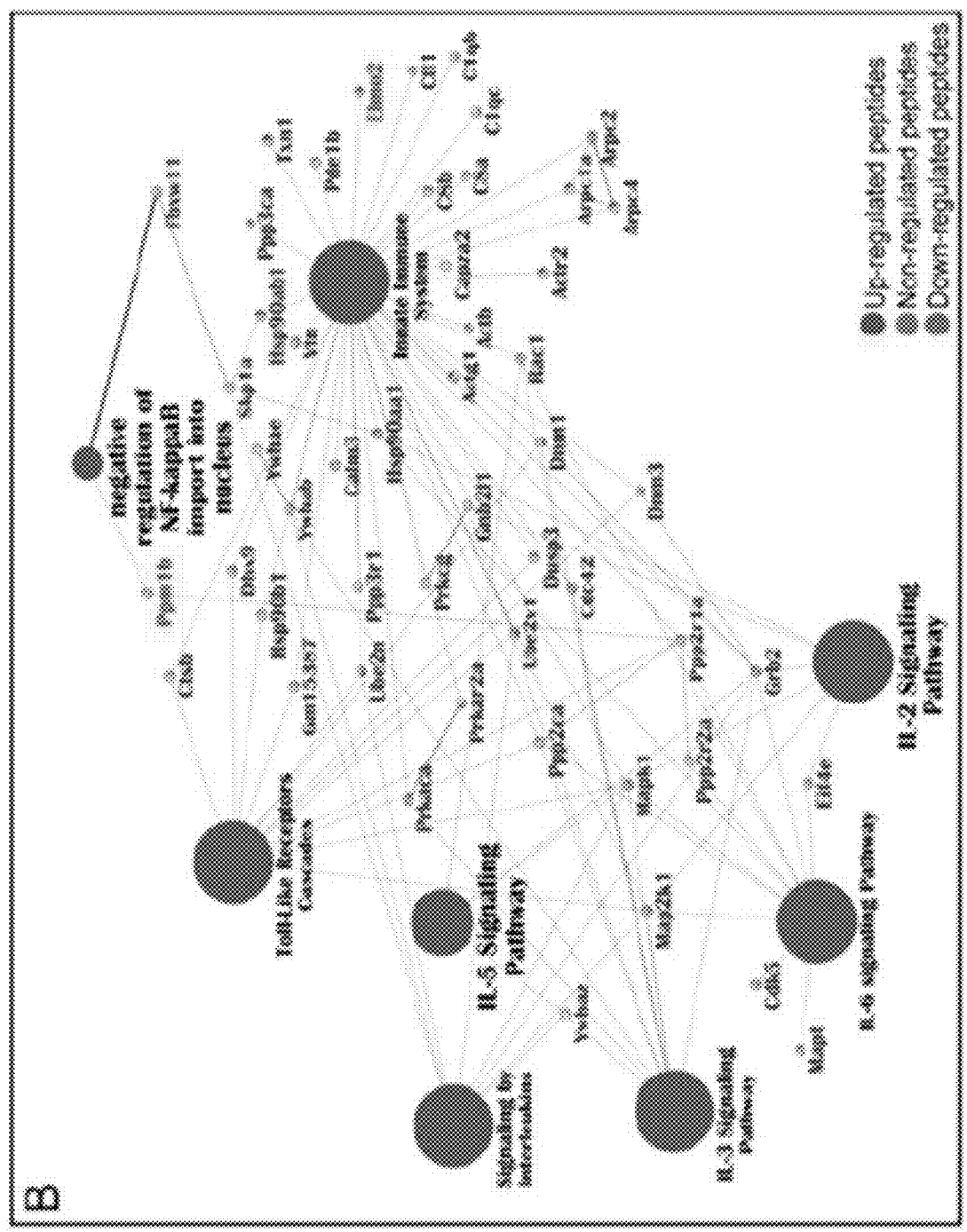

To compare the microglial transcriptome with the actual cell-type specific proteome the TRAP protocol was adapted and the ribosomes-associated peptides were collected 24 hrs following LPS challenge (Cao and Geballe, 1996) and label-free quantitative mass spectrometry was performed. Contrary to highly regulated mRNA/transcripts, LPS injection altered expression levels of one hundred proteins. Further, 68% of the detected proteins were down-regulated by at least 1.2-fold whereas 32% were significantly up-regulated by at least 1.2-fold. None of the highly up-regulated immune transcripts presented in clusters 1 and 2 (FIGS. 2 B and 2 C) were detected among the sequenced peptides. This was further confirmed by western blot analysis. First, protein expression levels of the 3 most up-regulated mRNAs (Saa3, Lcn2 and CC/5) were validated in a cell-type specific manner and western blot analysis on the ribosomes-attached microglia peptides was performed using antibodies that recognize the N terminus of the selected proteins. As shown in FIG. 2 D, none of the top 3 genes highly up-regulated at mRNA level, were detected at protein level. In contrast, the selected un-regulated ribosome-bound mRNAs such as CAP2 and actin were translated and detected by quantitative mass spectrometry and western blot analysis. This was validated by western blot analysis performed on the TRAP elution homogenates (FIG. 2 D). As further demonstrated in FIGS. 2 D and 2 E, western blot analysis from the whole brain tissue homogenates revealed that SAA3 and CCL5 protein levels were not significantly increased following LPS challenge. The un-regulated controls, CAP2 and actin were translated and detected at expected levels. The exception was the expression pattern of LCN2. This is consistent with previous evidence demonstrating that lcn2 may be present at mRNA levels in microglial cells, however, the major source of LCN2 protein in the brain are astrocytes and endothelial cells (Flo et al., 2004; Jin et al., 2014; Lee et al., 2015). It is noteworthy, that the un-regulated transcripts were normally translated and detected at expected levels by mass spectrometry (Tables 5 and 6). Taken together, the present results suggest that the observed translational repression was restricted to a cluster of the highly up-regulated immune transcripts directly associated with the microglial NF-κB network (FIG. 7).

TABLE 5

List of Up-Regulated Peptides

| Protein IDs | Symbol | Fasta headers | (LFQ) Fold Change (LPS vs. CTL) | (LFQ) Test Student (LPS vs. CTL) |
|---|---|---|---|---|
| P70266 | Pfkb3 | 6-phosphofructo-2-kinase/fructose-2, 6-biphosphatase 3 splice variant 3 | 17.04 | 0.004 |
| Q8BFZ3 | Actbl2 | Beta-actin-like protein 2 | 3.59 | 0.000 |
| Q7TPR4 | Actn1 | Alpha-actinin-1 | 2.19 | 0.000 |
| Q9WUM4 | Coro1c | Coronin-1C | 2.00 | 0.000 |
| Q8BP95 | Ate1 | Arginyl-tRNA--protein transferase 1 | 1.97 | 0.000 |
| O88587 | Comt | Catechol O-methyltransferase | 1.90 | 0.003 |
| Q8CDN6 | Txnl1 | Thioredoxin-like protein 1 | 1.86 | 0.002 |
| Q8VDM6 | Hnrnpul1 | 1 Heterogeneous nuclear ribonucleoprotein U-like protein 1 | 1.79 | 0.000 |
| Q9CSH0 | Hnrnpll | Heterogeneous nuclear ribonucleoprotein L-like | 1.69 | 0.033 |
| Q61304 | Ank1 | Erythroid ankyrin (Fragment) | 1.53 | 0.004 |
| Q99K48 | Nono | Non-POU domain-containing octamer-binding protein | 1.51 | 0.001 |
| Q3U232 | Coro1a | Coronin-1A | 1.50 | 0.010 |
| Q8VIJ6 | Sfpq | Splicing factor, proline- and glutamine-rich | 1.45 | 0.000 |
| Q3TYS9 | Oplah | 5-oxoprolinase | 1.44 | 0.016 |
| Q9CY58 | Serbp1 | Plasminogen activator inhibitor 1 RNA-binding protein | 1.41 | 0.003 |
| Q3ULD5 | Mccc2 | Methylcrotonoyl-Coenzyme A carboxylase 2 (Beta) | 1.41 | 0.019 |
| Q99MR8 | Mccc1 | Methylcrotonoyl-CoA carboxylase subunit alpha, mitochondrial | 1.40 | 0.000 |
| Q8VI63 | Mob2 | MOB kinase activator 2 | 1.38 | 0.004 |
| P36993 | Ppm1b | Isoform Beta-4 of Protein phosphatase 1B | 1.37 | 0.003 |
| P21107 | Tpm3 | Tropomyosin alpha-3 chain | 1.37 | 0.007 |
| Q9JKB3 | Ybx3 | Isoform 2 of Y-box-binding protein 3 | 1.33 | 0.019 |
| Q7TSE6 | Stk38 | Serine/threonine-protein kinase 38-like | 1.31 | 0.002 |
| P61979 | Hnrnpk | Heterogeneous nuclear ribonucleoprotein K | 1.30 | 0.000 |
| O88342 | Wdr1 | WD repeat domain 1 | 1.28 | 0.003 |
| Q922P9 | Glyr1 | Putative oxidoreductase GLYR1 | 1.27 | 0.006 |
| P49813 | Tmod3 | Tropomodulin-3 | 1.26 | 0.007 |
| P70349 | Hint1 | Histidine triad nucleotide-binding protein 1 | 1.25 | 0.006 |
| Q9Z2C4 | Mtmr1 | Myotubularin-related protein 1 | 1.24 | 0.008 |
| Q8BHL5 | Elmo2 | Engulfment and cell motility protein 2 | 1.24 | 0.002 |
| Q6ZPE2 | Sbf1 | Myotubularin-related protein 5 | 1.23 | 0.001 |
| Q8VHK9 | Dhx36 | ATP-dependent RNA helicase DHX36 | 1.22 | 0.002 |
| Q8R326 | Pspc1 | Paraspeckle component 1 | 1.20 | 0.004 |

TABLE 6

Inflammation and Immune Response Network: List of Un-Regulated mRNAs and Peptides

| Symbol | Fasta headers | mRNA Fold Change (linear) (LPS vs. CTL) | ANOVA p-value (LPS vs. CTL) | (LFQ) Peptide Fold Change (LPS vs. CTL) | ((LFQ) Test Student (LPS vs. CTL) |
|---|---|---|---|---|---|
| Acrt2 | ARP2 actin-related protein 2 | −1.02 | 0.712157 | −1.04 | 0.215 |
| Actb | actin, beta | −1.05 | 0.883213 | −1.12 | 0.000 |
| Actg1 | actin, gamma, cytoplasmic 1; actin, gamma, pseudogene 1 | −1.04 | 0.615592 | −1.23 | 0.005 |
| Arpc1a | actin related protein 2/3 complex, subunit 1A | −1.03 | 0.946712 | 1.31 | 0.060 |
| Arpc2 | actin related protein 2/3 complex, subunit 2 | 1.06 | 0.925415 | 1.01 | 0.963 |
| Arpc4 | actin related protein 2/3 complex, subunit 4 | 1.03 | 0.902912 | −1.07 | 0.022 |
| C1qb | complement component 1, q subcomponent, beta polypeptide | 1.63 | 0.009647 | 1.13 | 0.052 |
| C1qc | complement component 1, q subcomponent, C chain | 1.02 | 0.418866 | 1.10 | 0.070 |
| C8a | complement component 8, alpha polypeptide | −1.05 | 0.402028 | 1.04 | 0.503 |
| C8b | complement component 8, beta polypeptide | 1.36 | 0.250288 | 1.06 | 0.452 |
| Calm3 | calmodulin 3; calmodulin 2; calmodulin 1 | −1.12 | 0.790495 | 1.01 | 0.738 |
| Capza2 | capping protein (actin filament) muscle Z-line, alpha 2 | 1.01 | 0.891642 | −1.08 | 0.147 |
| Cdc42 | cell division cycle 42 | −1.19 | 0.480546 | −1.13 | 0.191 |
| Cdk5 | cyclin-dependent kinase 5 | 1.01 | 0.992308 | −1.05 | 0.207 |
| Cfl1 | epidermal growth factor-containing fibulin-like extracellular matrix protein 2; cofilin 1, non-muscle | 1.04 | 0.721854 | −1.03 | 0.093 |
| Ctsb | cathepsin B | 1.09 | 0.439574 | 1.18 | 0.152 |
| Dhx9 | DEAH (Asp-Glu-Ala-His) box polypeptide 9 | −1.39 | 0.764582 | −1.12 | 0.304 |
| Dnm1 | dynamin 1 | −1 | 0.525399 | −1.19 | 0.003 |
| Dnm3 | dynamin 3 | 1.09 | 0.91568 | −1.10 | 0.211 |
| Dusp3 | dual specificity phosphatase 3 (vaccinia virus phosphatase VH1-related) | −1.2 | 0.269172 | −1.11 | 0.443 |
| Eif4e | eukaryotic translation initiation factor 4E; microRNA 1956 | 1.11 | 0.154961 | −1.12 | 0.012 |
| Elmo2 | engulfment and cell motility 2 | 1.14 | 0.360978 | 1.24 | 0.002 |
| Fbxw11 | F-box and WD-40 domain protein 11 | 1.16 | 0.659338 | −1.43 | 0.001 |
| Gnb2l1 | guanine nucleotide binding protein (G protein), beta polypeptide 2 like 1 | 1.07 | 0.991956 | 1.13 | 0.002 |
| Hsp90aa1 | heat shock protein 90, alpha (cytosolic), class A member 1 | −1.18 | 0.5152 | −1.10 | 0.004 |
| Hsp90ab1 | heat shock protein 90 alpha (cytosolic), class B member 1 | 1.02 | 0.899416 | −1.21 | 0.000 |
| Hsp90b1 | heat shock protein 90, beta (Grp94). member 1; predicted gene 15344 | −1.23 | 0.33078 | −1.16 | 0.048 |
| Mapk1 | mitogen-activated protein kinase 1 | 1.03 | 0.467805 | 1.02 | 0.538 |
| Mapt | microtubule-associated protein tau | −1.24 | 0.673261 | −1.18 | 0.004 |
| Pde1b | phosphodiesterase 1B, Ca2+-calmodulin dependent | −1.12 | 0.022429 | −1.34 | 0.028 |
| Ppm1b | protein phosphatase 1B, magnesium dependent, beta isoform | 1.34 | 0.938437 | 1.37 | 0.003 |
| Ppp2r2a | protein phosphatase 2 (formerly 2A), regulatory subunit B (PR 52), alpha isoform | −1.08 | 0.476214 | −1.05 | 0.006 |
| Ppp3ca | protein phosphatase 3, catalytic subunit, alpha isoform | −1.1 | 0.584615 | 1.11 | 0.005 |
| Ppp3r1 | protein phosphatase 3, regulatory subunit B, alpha isoform (calcineurin B, type I); WD repeat domain 92 | −1.06 | 0.57225 | 1.10 | 0.114 |
| Prkaca | protein kinase, cAMP dependent, catalytic, alpha | −1.17 | 0.578658 | 1.04 | 0.522 |
| Prkar2a | protein kinase, cAMP dependent regulatory, type II alpha | 1.08 | 0.779202 | 1.02 | 0.772 |
| Prkcg | protein kinase C, gamma | −1.04 | 0.966931 | 1.13 | 0.012 |
| Rac1 | RAS-related C3 botulinum substrate 1 | 1.03 | 0.204101 | 1.05 | 0.052 |
| Skp1a | S-phase kinase-associated protein 1A | 1.02 | 0.809196 | 1.04 | 0.430 |
| Txn1 | thioredoxin 1 | 1.17 | 0.853458 | 1.12 | 0.009 |
| Ube2n | ubiquitin-conjugating enzyme E2N; ubiquitin-conjugating enzyme E2 N-like | −1.05 | 0.495606 | 1.06 | 0.224 |
| Ube2v1 | ubiquitin-conjugating enzyme E2 variant 1; predicted Pseudogene 8325; predicted gene 20431 | −1.1 | 0.84211 | 1.13 | 0.021 |
| Ywhab | tyrosine 3-monooxygenase/tryptophan 5-monooxygenase activation | −1.1 | 0.854279 | −1.05 | 0.075 |
| Ywhae | tyrosine 3-monooxygenase/tryptophan 5-monooxygenase activation | −1.1 | 0.555007 | 1.05 | 0.015 |
| Ywhaz | tyrosine 3-monooxygenase/tryptophan 5-monooxygenase activation | 1.03 | 0.620127 | 1.01 | 0.533 |

Example 4

Figure 3:
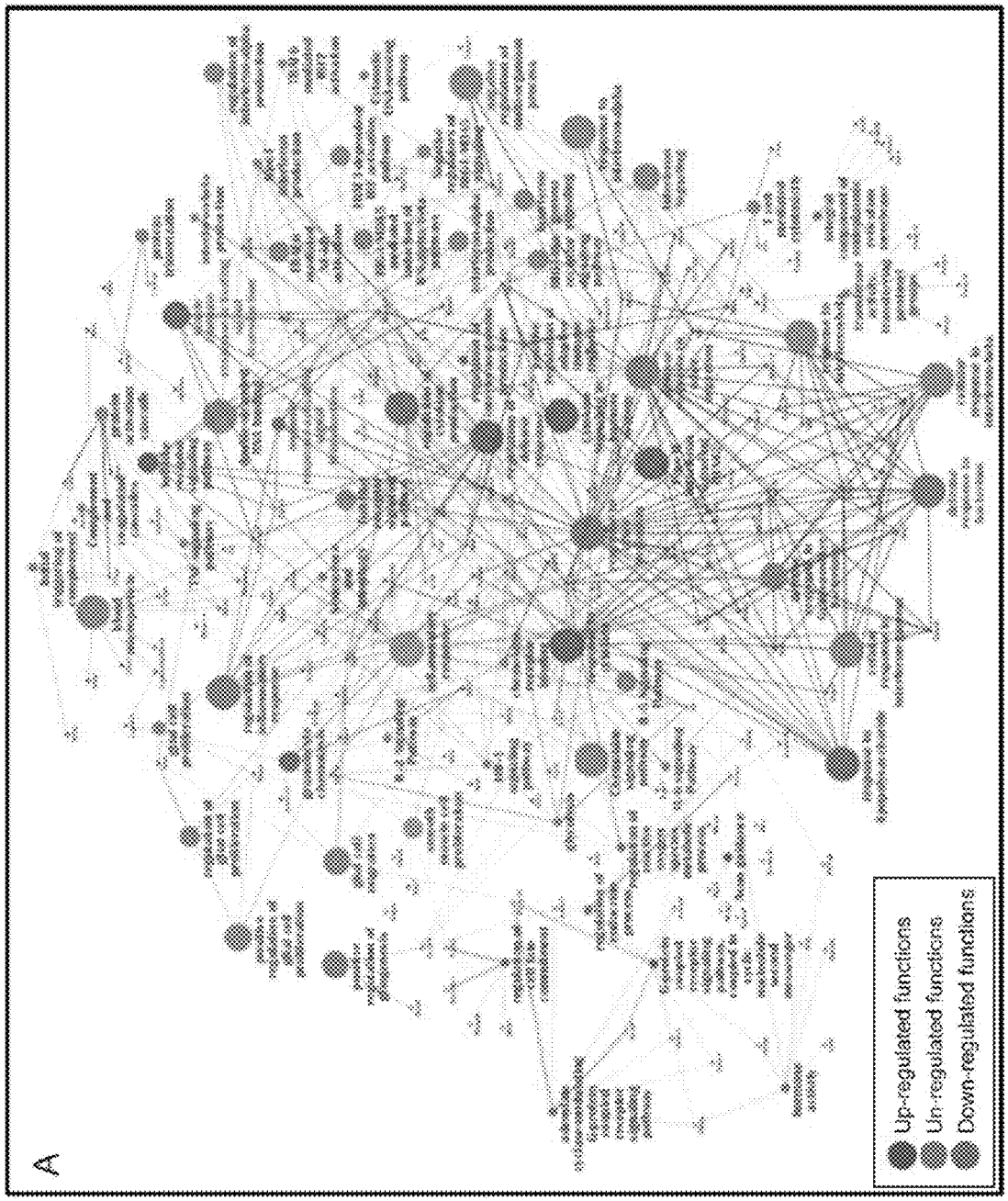
FIG. 3 Diverging mRNA and Protein Networks in Activated Microglia. (A) The biological role of up or down regulated transcripts or (B) peptides visualized with ClueGo. Transcripts/peptides-associated with the same term are represented by a node. Terms with a majority of up-regulated transcripts/peptides are shown in red. Terms with a majority of down regulated transcripts/peptides are shown in green. Gray nodes contain equal proportions of up and down regulated transcripts/peptides. The size of the nodes reflects the number of genes/term vs cluster. The color gradient shows the enrichment significance of the terms. Edges show the association of the transcript/peptide with the terms. The thickness of the edge reflected the association significance. (C) Pie graph depicting the top 10 biological functions of up-regulated transcripts. (D) Pie graph depicting the top 10 biological functions of up-regulated peptides.
Figure 3:
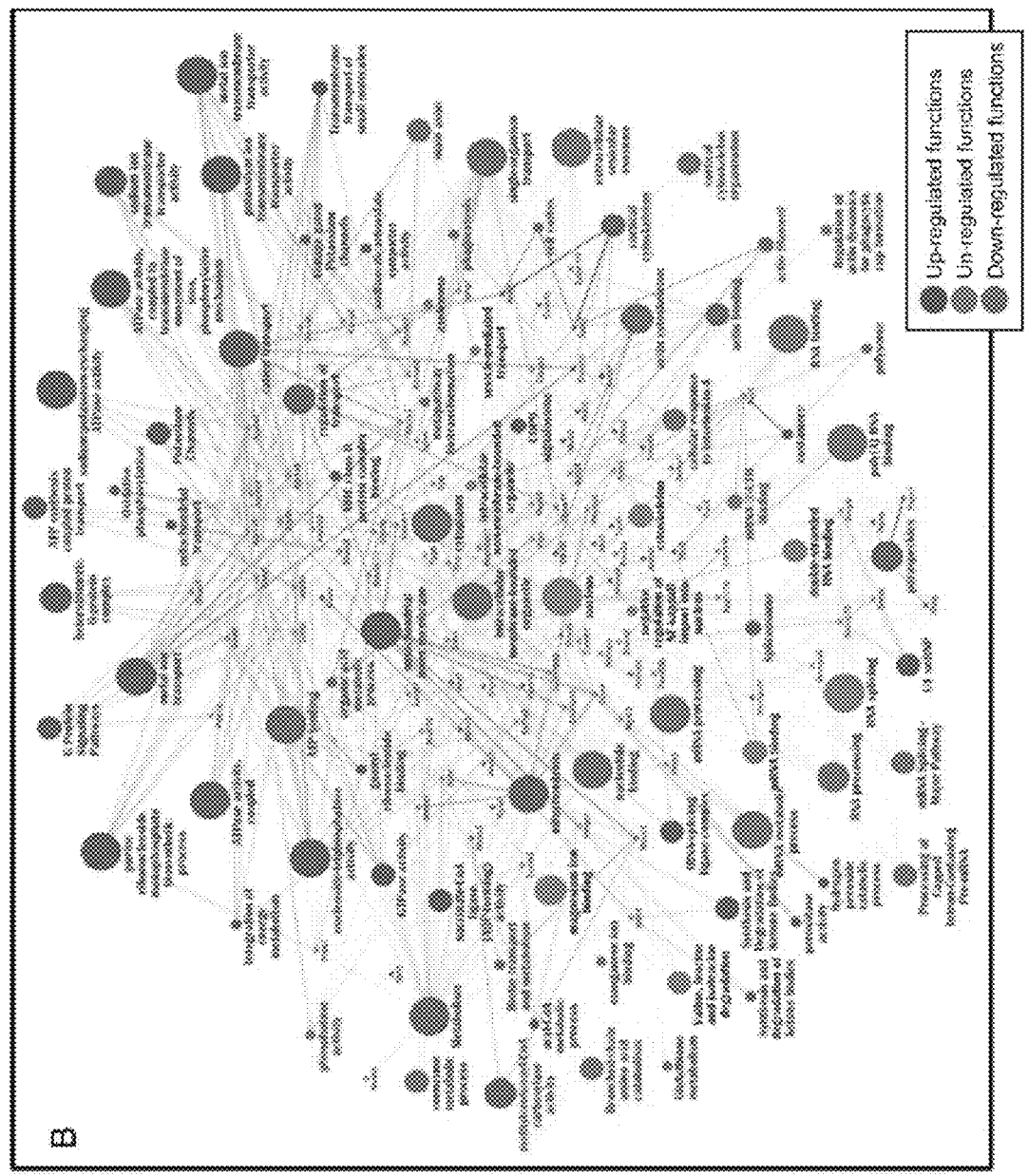
Figure 3:
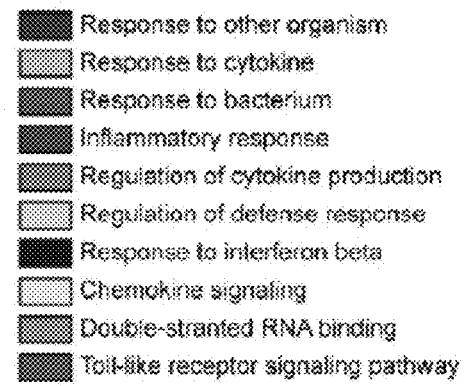
Figure 3:
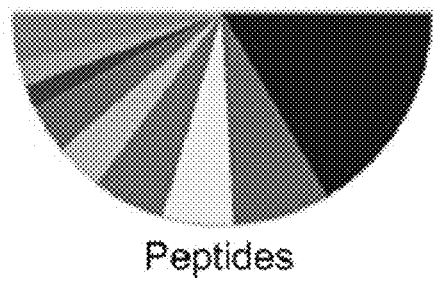

LPS-Activated Microglial Cells Exhibit Distinct Molecular Signatures for mRNAs and Proteins Next, an investigation was performed to understand how the observed translational repression of highly regulated immune genes affects biological functions of activated microglia. To obtain a general view of the microglia response to LPS challenge, Cytoscape (Shannon et al., 2003) and the ClueGo cluster analysis (Bindea et al., 2013; Bindea et al., 2009) were used and all regulated mRNA/protein functions (FIGS. 3A and 3B) were mapped. As shown in FIGS. 3 A and 3 B, the functional annotation clustering revealed a striking difference in microglia mRNA and protein responses to innate immune challenge. The network of LPS-regulated transcripts is highly enriched in up-regulated terms/functions (red nodes), while the network of LPS-regulated peptides are highly enriched in down regulated terms/functions (green nodes). The marked divergence was also reflected in the top biological functions. As shown in FIG. 3 C, the top 10 biological functions associated with the up-regulated transcripts were identified. The majority of these functions are related to inflammation and immune response thus summarizing perfectly the inflammatory cascade triggered by LPS challenge leading to activation of NF-κB signaling (Medzhitov and Horng, 2009). In contrast to highly specialized immune mRNA response, the top 10 biological functions of up-regulated proteins were restricted to cytoskeleton, RNA metabolism and housekeeping functions (FIG. 3 D). Hence, the results revealed that a selective translational repression of the ribosome bound- and highly regulated innate immune genes contributes to formation of a distinct/diverging mRNA and protein molecular signatures in activated microglia.

Example 5

Translational Regulation of Gene Expression in Innate Immune Response

Although in eukaryotes, initiation is considered a rate-limiting step of translation that is often targeted for regulation (Gao and Roux, 2015; Sonenberg and Hinnebusch, 2009), the results revealed that regulation of mRNAs occurs also at ribosomes, after initiation of translation. This suggests an additional layer of control/check point of highly regulated innate immune genes by the ribosome-based mechanism. Given that the most post-transcriptional control mechanisms target the 3'untranslated region (3'UTR) of mRNAs to repress and/or to activate expression of the target transcript (Anderson, 2010), it is hypothesized that the 3'UTR of the highly up-regulated genes, such as Saa3 may contain the regulatory sequences responsible for the observed translational repression. To address this, the wild-type 3'UTR of the Saa3 transcript was cloned in the pGL3-reporter plasmid consisting of luciferase under the control of SV40 promoter/regulatory elements (FIG. 4 A). HEK293 cell line was transfected with the pGL3 vector (pGL3), pGL3-promoter-Saa3-3'UTR-wt vector (pGL3-Saa3-3'UTR-wt) (SEQ ID NO:2) or pGL3-promoter-SCRAMBLE vector (pGL3-SCRAMBLE) (SEQ ID NO:3), respectively. Importantly, transfection of pGL3-Saa3-3'UTR-wt vector markedly decreased the reporter vector activity (by almost 80%), while transfection of the pGL3-SCRAMBLE vector restored the luciferase activity close to the control levels (pGL3 vector) (FIG. 4 B), thus clearly demonstrating existence of regulatory elements in the Saa3-3'UTR. To confirm that the loss of luciferase activity following transfection of the pGL3-Saa3-3'UTR-wt is caused by translational repression (and not by change in mRNA stability and/or degradation), BV2 cells stably expressing F/EGFP-L10a plasmid were used. Forty-eight hours after transfection with pGL3 and pGL3-Saa3-3'UTR-wt vectors, mRNA was purified using TRAP protocol then the ribosome-associated mRNA encoding luciferase was quantified by real-time-q-PCR in both conditions. As shown in FIG. 4 C, analysis revealed that, the addition of Saa3-3'UTR to pGL3 vector did not cause significant change in ribosome-associated luciferase mRNA ($184 \times 10^3 \pm 27 \times 10^3$, pGL3 vs $240 \times 10^3 \pm 35 \times 10^3$ pGL3-Saa3-3'UTR-wt, n=6), thus suggesting that the Saa3 3'UTR mediated mechanism acts by directly inhibiting translation of ribosome-bound mRNA.

Having demonstrated an important role of Saa3-3'UTR role in the regulation of protein expression, to identify of the specific 3'UTR region involved in the observed translational repression was sought. RNA binding proteins (RBPs) and microRNAs (miRNAs) are known to play an important role in the regulation of mRNA expression (Glisovic et al., 2008; Nilson and Assmann, 2007). By using RBP map website (Paz et al., 2014), the relative RBPs positions in the Saa3-3'UTR (FIG. 4 D) were mapped. Bioinformatics tool (RBP-map) predicted several RBPs that bind to the 3'UTR of Saa3 with a different distribution. All these points guided to a division of the Saa3 3'UTR in 3 segments A, B and C (FIG. 4 D). To investigate functional relevance of each segment, reporter plasmids containing different segments of Saa3-3'UTR were created (FIG. 4 E) (SEQ ID NOS: 4 to 7). HEK 293 cells were transfected with the indicated plasmids and subjected to luciferase activity assay after 48 hrs. As shown in FIG. 4 F the Saa3-3'UTR constructs containing deletion of the domains A, C, B or domains B+C partially alleviated the translational inhibition and gradually increased the luciferase activity. While the complete 3'UTR sequence markedly decreased luciferase activity, the tested deletion mutants gradually restored it, suggesting that each of the 3 domains contain regulatory elements contributing to a similar extent in the inhibition of translation of the Saa3 transcript (Ciafre and Galardi, 2013; Jiang and Coller, 2012).

Example 6

Serine/Arginine-Rich Splicing Factor 3 Serves as a Master Regulator of the Innate Immune Gene Translation Given the importance of the complete 3'UTR of Saa3 (A, B and C domains) in the posttranscriptional regulation of SAA3 protein expression, it was hypothesized that the observed translational repression is orchestrated by RBPs that bind to all three domains of the 3'UTR. Interestingly, one of the RBPs that met this criterion is Serine/Arginine-Rich Splicing Factor 3 (SRSF3/SRp20) (FIG. 4 D) (SEQ ID NO:12). Indeed, it was found that SRSF3 binds to complete 3'UTR of Saa3 and has more than twenty putative binding sites along the 128 bp-3'UTR. Importantly, SRSF3 mRNA and protein were identified in transcriptome/proteome analysis as un-regulated ribosome-bound mRNA/peptide after LPS challenge (mRNA fold change LPS vs CTL: 1.11; ANOVA p-value=0.953; LFQ fold change LPS vs CTL: 1.01, LFQ t-student test=0.894). SRSF3 belongs to the Serine-arginine-rich (SR) proteins family that contains 12 mammalian RNA binding proteins with a functional implication in RNA metabolism. SR proteins harbor one or two RNA-recognition motif (RRM) domains (SEQ ID NO:13) at the N-terminus and a serine-arginine dipeptide repeat (RS) domain (SEQ ID NO:14) at the C-terminus (Manley and Krainer, 2010). Like other SR proteins, SRSF3 is involved in the alternative splicing events, however, recent reports emphasize its role in the mechanisms involved in post-transcriptional regulation, such as mRNA export, surveillance, stability and translation (Kim et al., 2014). Evidence suggests that the activities of SRs proteins are regulated by cycles of phosphorylation/dephosphorylation (Misteli and Spector, 1997), therefore it was first analyzed whether LPS challenge alters phosphorylation levels of SRSF3. Indeed, LPS increases by 2.5 fold the level of phosphorylated SRSF3 in BV2 cells (FIGS. 5 A and 5 B), whereas the level of total SRSF3 does not significantly change as reported by proteomics and confirmed by western blot analysis (FIGS. 5

Figure 5:
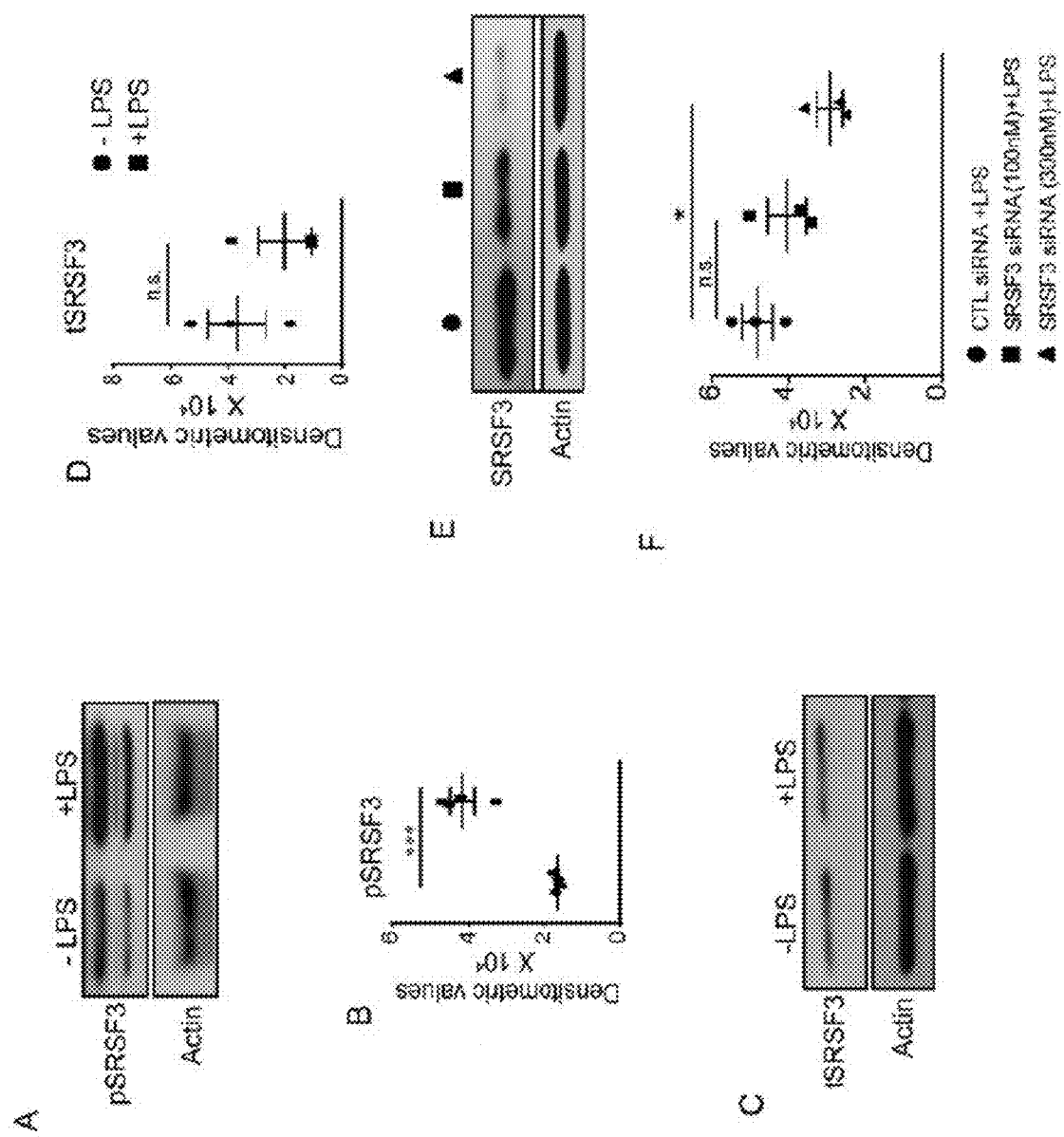
FIG. 5 SRSF3 Regulates Inflammatory Genes Expression via 3'UTR. (A) Western blots of phosphorylated SRSF3 (pSRSF3) expression in BV2 cells 24 hours after LPS treatment. (B) Quantitative western blot analysis for pSRSF3. (Data are mean SEM, n=4; ***p<0.001). (C) Total SRSF3 (tSRSF3) expression analyzed by western blot 24 hours after LPS. (D) Quantitative analysis of western blot showed the expression level of tSRSF3. (Data are mean±SEM, n=3; p>0.05). (E) Western blot analysis of LPS-treated BV2 cells transfected with a control siRNA (CTL siRNA) or siRNA against SRSF3 (100 nM or 300 nM) (SEQ ID NOS:8 to 11). (F) Quantitative analysis of western blot showed the expression level of endogenous SRSF3 48 hours post siRNA transfection. (Data are mean±SEM, n=3; n.s.: p>0.05; *p<0.05). (G) Luciferase reporters (pGL3 and pGL3-Saa3-3'UTR-wt) were co-transfected with CTL siRNA or SRSF3 siRNA (300 nM) (SEQ ID NOS:8 to 11) in LPS-treated BV2 cells. Luciferase activity has been measured 48 hrs after transfection. Data represent mean±SEM of two independent experiments (n=6; n.s.: p>0.05; *p<0.05; *p<0.001). (H) Western blot of SAA3 expression in BV2 cells 24 hrs after LPS exposure. (1) Western blot analysis showed the expression level of endogenous SAA3 after SRSF3 knockdown. (Data are mean±SEM, n=3; n.s.: p>0.05; p<0.01). (J) Schematic representation of the putative positions of SRSF3 along the 3'UTR of Lcn2, Ccl5 and Ccl3 respectively. (K) Western blot analysis of LCN2, CCL5 and CCL3 expression in BV2 cells transfected with the siRNA directed against SRSF3 and treated with LPS for 24 hours. (L) Quantitative analysis of western blot shows the endogenous LCN2, CCL5 and CCL3 levels after SRSF3 knockdown and treatment with LPS (n=3; n.s.: p>0.05; p<0.01; *p<0.001).
Figure 5:
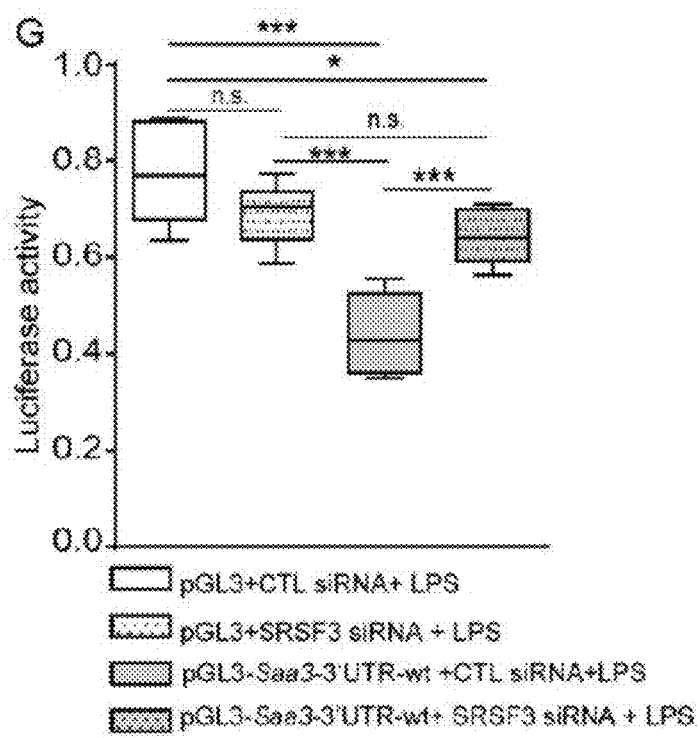
Figure 5:
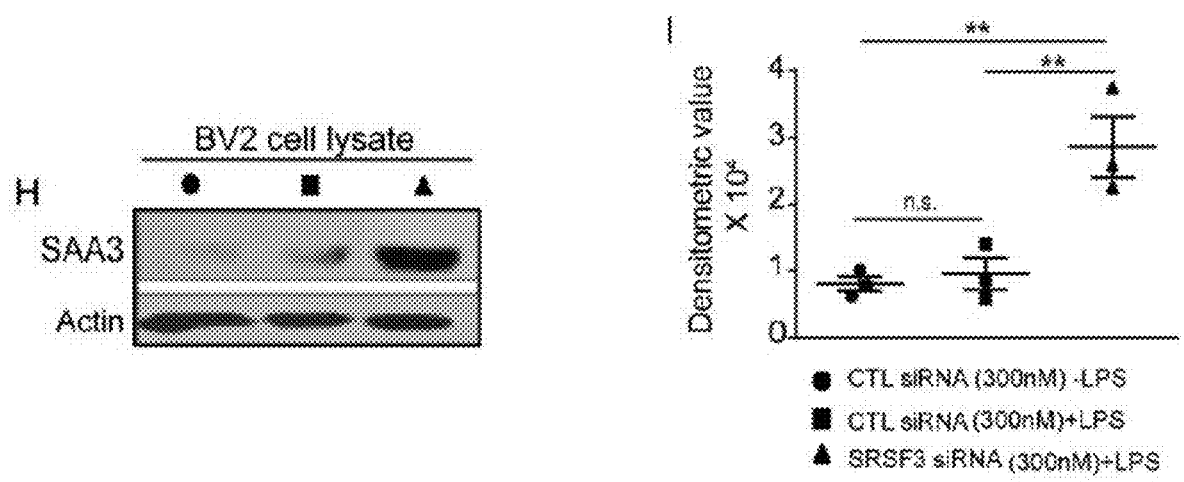
Figure 5:
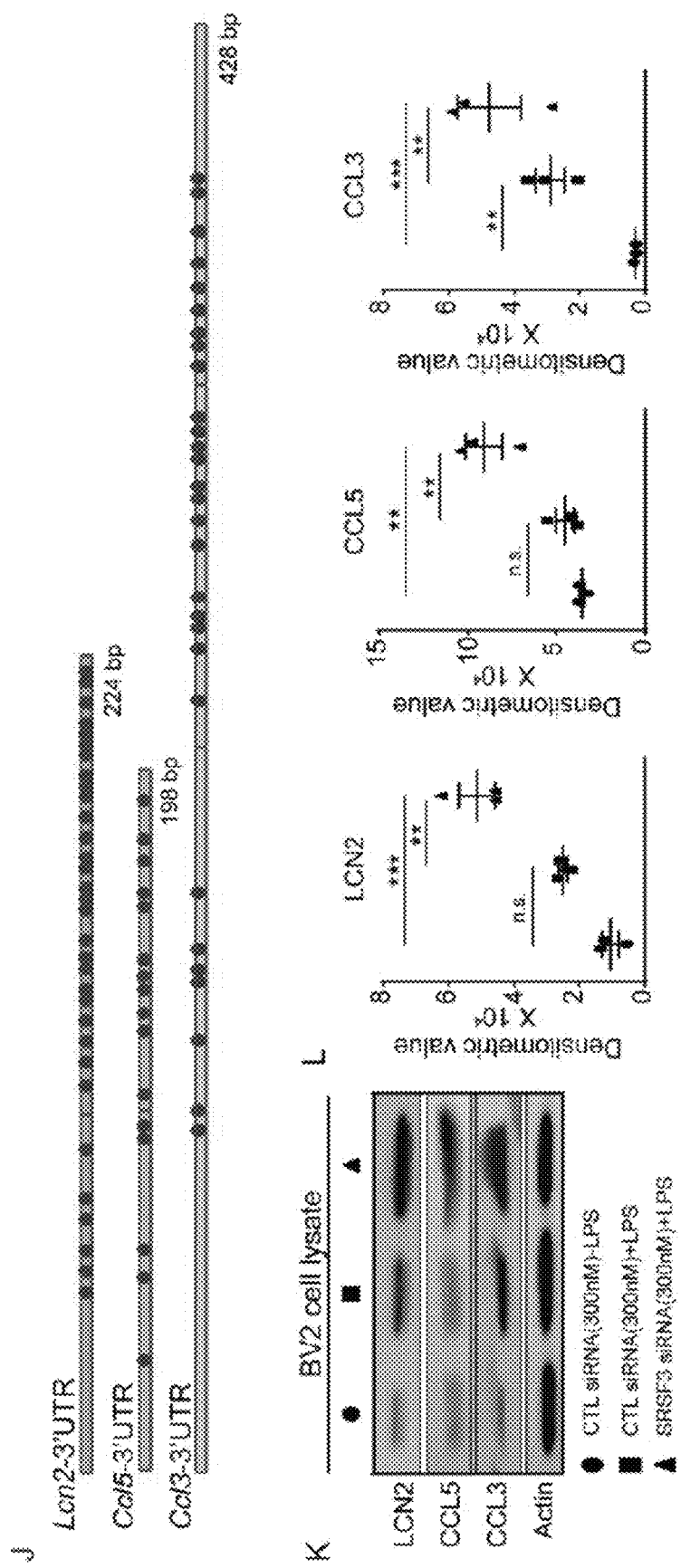

C and 5 D). To directly assess whether SRSF3 is the RBP involved in the SAA3 translational repression, SRSF3 knockdown was performed using a small interfering RNAs (siRNAs) directed against the endogenous SRSF3 (SRSF3-siRNA) (SEQ ID NOS:8 to 11). As described above (FIG. 4), the BV2 cells were transfected with pGL3 vector or pGL3-Saa3-3'UTR-wt in the presence of small interfering RNAs (siRNAs) directed against endogenous SRSF3 (SRSF3-siRNA) or control (CTL-siRNA). As shown in FIGS. 5 E and 5 F, 300 nM of siRNA efficiently knocked down SRSF3 resulting in significant, 40% decrease in expression levels of the endogenous SRSF3 protein (FIG. 5 F). Next, it was investigated whether SRSF3 is directly responsible for translational repression of SAA3. As shown in FIG. 5 G, co-transfection of the pGL3-Saa3-3'UTR with the siRNA against SRSF3 restored luciferase activity revealing that SRSF3 is involved in the 3'UTR-mediated translational repression of Saa3. As further confirmed by western blot analysis, the SRSF3-siRNA (300 nM) induced knockdown resulted in significant, a 3.01 fold increase in SAA3 endogenous protein levels in the LPS-challenged BV2 cells (FIGS. 5 H and 5 I). Next, it was investigated whether the SRSF3-mediated translational repression may represent a more general mechanism involved in the translational regulation of the highly regulated immune genes/mRNAs. To address this, the highly regulated transcripts from the cluster 1 were selected (FIG. 2 B; zoom1): Lcn2, Ccl5 and Ccl3. Namely, all of the listed genes belong to a cluster of the highly up-regulated transcripts not detected among sequenced peptides. Next, bioinformatics tools were used to search for potential SRSF3 binding sites at 3'UTR of the selected genes. As schematically presented in FIG. 5 J, a large distribution of the potential binding sites were observed for SRSF3 along the 3'UTR of Lcn2, Ccl5 and Ccl3, respectively. To investigate whether SRSF3 is involved in translation repression of the Lcn2, Ccl5 and Ccl3 mRNAs, the series of SRSF3-knockdown experiments were performed. As previously described, experiments were performed on the LPS-challenged BV2 cells in presence of the siRNA-SRSF3 or CTL siRNA (SEQ ID NOS:8 to 11). As shown in FIGS. 5 K and 5 L, LPS in presence of CTL siRNA caused an initial increase in CCL3 levels, however a knockdown of SRSF3 further abolished the observed translational repression. As revealed by western blot analysis, the SRSF3 knockdown was associated with a significant upregulation of LCN2 (4.89 fold increase), CCL5 (2.5 fold increase) and CCL3 (2.19 fold increase) protein levels when compared to corresponding controls, thus clearly suggesting a role of SRSFR3 in translational repression of the highly regulated transcripts from the cluster 1. As further revealed in Table 1 presented before, based on screening data, the 3'UTR regions of several other highly regulated transcripts are enriched in the putative binding sites for SRSF3, thus raising the possibility that SRSF3 may serve as a master regulator of the innate immune genes translation.

Example 7

SRSF3 Controls Innate Immune Cascade In Vivo

Figure 6:
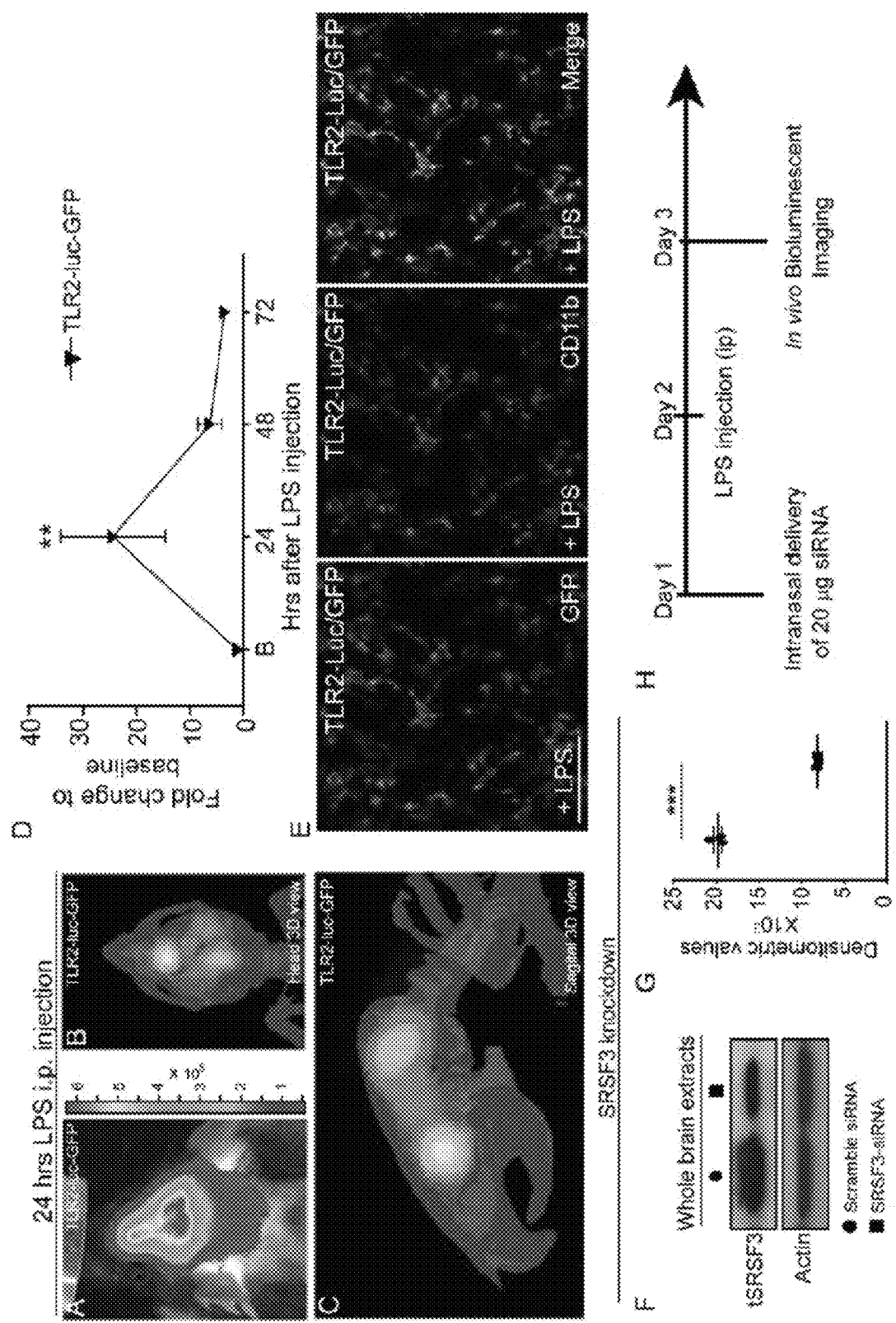
FIG. 6 SRSF3 is a Translational Regulator of Inflammatory Genes in Vivo. (A) In vivo imaging of TLR2 induction after LPS injection; representative photographs at 24 hrs after LPS injection. The color calibrations at the right are photons counts. (B) 3D view of the head showing detected photons by the CCD camera. (C) 3D reconstruction of bioluminescent signal 24 hrs after i.p. LPS injection. (D) Plot of the data obtained by measuring the photon emission. The black line shows the TLR2 signal induction 24-72 hrs after LPS (Data are mean±SEM, baseline: n=5, LPS 24 hrs n=5; LPS 48 hrs: n=4; LPS 72 hrs: n=4; Baseline vs LPS 24 hrs: p<0.01; Baseline vs LPS 48 hrs and Baseline vs LPS 72 hrs: p>0.05; LPS 24 hrs vs LPS 48 hrs and LPS 24 hrs vs LPS 72 hrs: p<0.01). (E) TLR2-driven GFP transgene expression in brain sections 24 hrs after LPS in TLR2-luc-GFP mice (Lalancette-Hebert et al., 2009). GFP immunostaining (green) co-localized with CD11b (red). Scale bars, 50 μm. (F) Western blot analysis of whole brain extracts after intranasal administration of Scramble-siRNA or SRSF3-siRNA (SEQ ID NOS: 8 to 11). (G) Quantitative analysis of western blot showed the expression level of endogenous SRSF3 48 hours post siRNA administration. (Data are mean±SEM, n=3; p*<0.001). (H) Schematic representation of the experimental timeline. (1) Bioluminescence imaging of TLR2 signal before (baseline) and after intranasal delivery of Scramble-siRNA (J) or SRSF3-siRNA (K) in LPS condition (5 mg/kg). (L) The longitudinal quantitative analysis of the total photon emissions from the brain represented by the fold change to baseline in the TLR2-luc-GFP mice that received SRSF3-siRNA or Scramble-siRNA. All mice were injected i.p. LPS (5 mg/kg) for 24 hrs (Data are mean±SEM, Scramble-siRNA+LPS-24 hrs: n=5; SRSF3-siRNA+LPS-24 hrs: n=7; LPS-24 hrs: n=5; n.s.: p>0.05; p<0.01; p*<0.001. (M) Representative photomicrographs of Iba1-stained brain sections from Scramble- or SRSF3-siRNA (N) conditions after LPS challenge. Scale bars, 50 μm. (O) Optical density quantification of the Iba-1 staining (n=3; p*<0.001). (P) Western blot analysis of SAA3, LCN2, CCL5 and CCL3 proteins expression after LPS in purified microglia. (Q) Quantitative analysis of western blot of the expression of microglial SAA3, LCN2, CCL5 and CCL3 proteins after Scramble/SRSF3-siRNA administration. Data represent mean±SEM (n=3; *p<0.05, p<0.01, *p<0.001).
Figure 6:
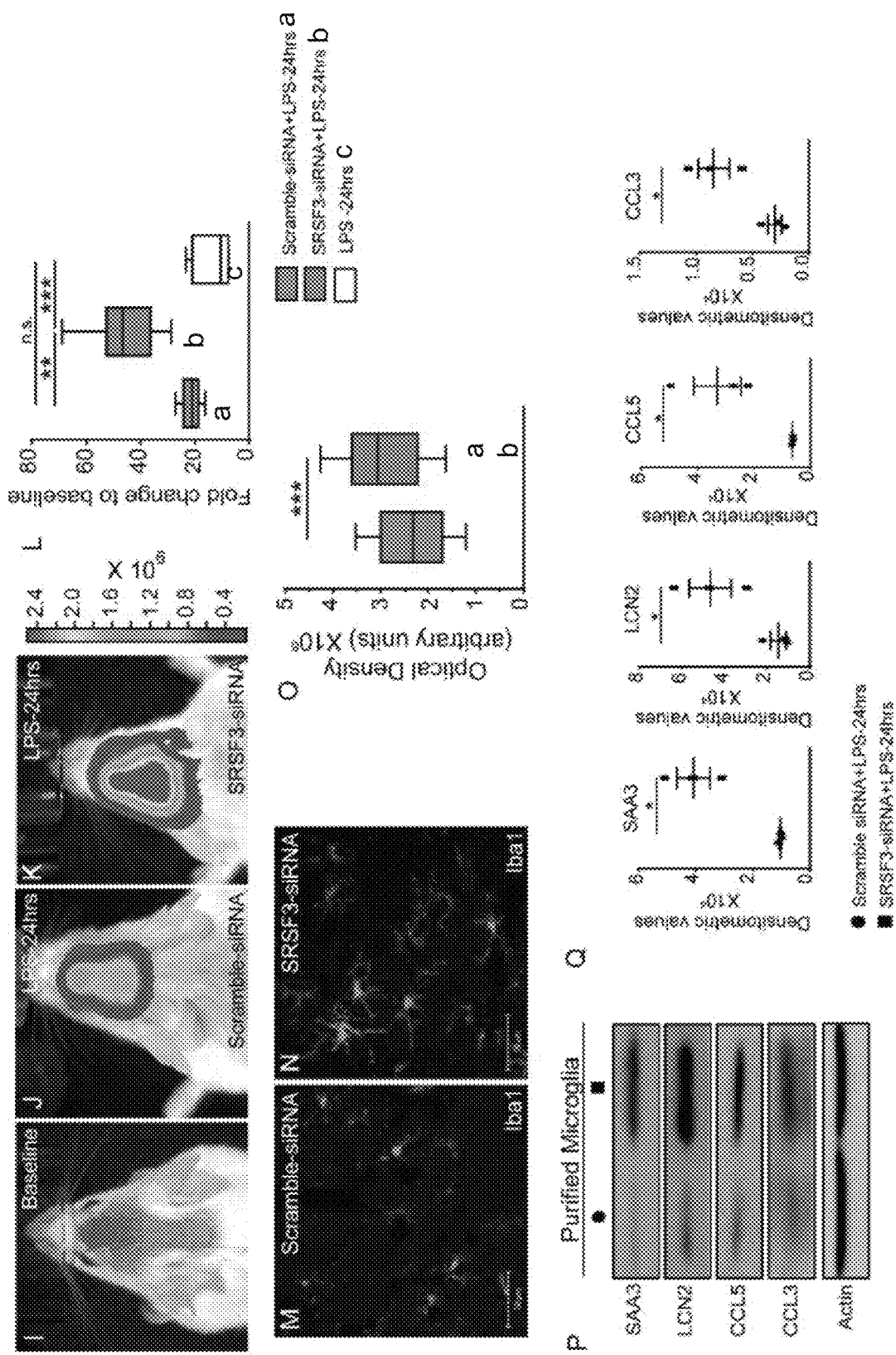
Figure 8:
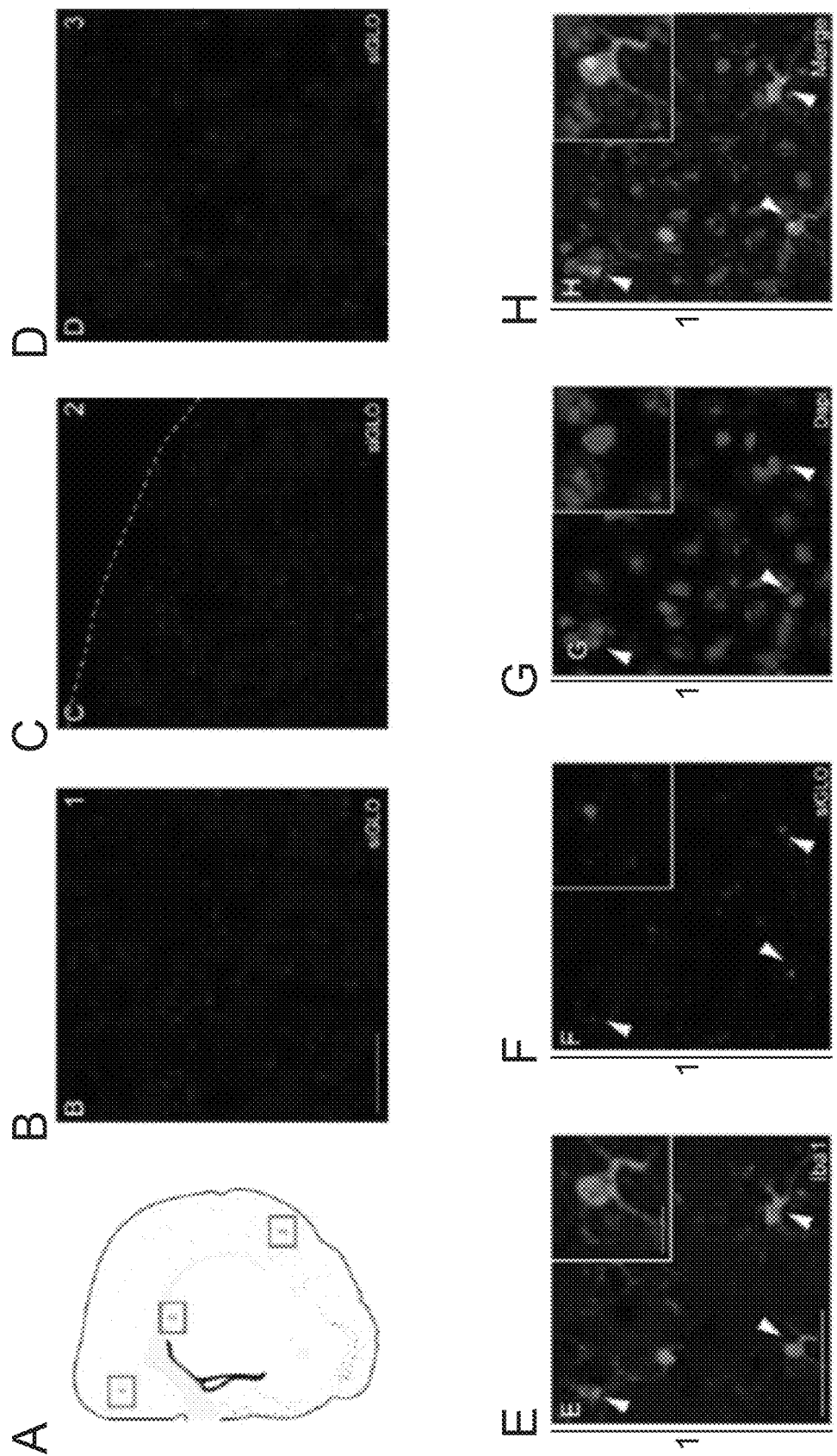
FIG. 8 Distribution of the siGLO in the Different Regions of the Brain. (A) Schematic representation of the three selected regions to visualize the distribution of the siGLO in the brain, 1: cortex; 2: striatum near corpus callosum; 3: cortex. (B, C and D) siGLO distribution (red dots) in the three selected regions after intranasal delivery. siGLO was co-transfected with Scramble- or SRSF3-siRNA to have a visual assessment of the siRNA uptake into the brain. Scale bars: 10 and 50 μm. (E-P) siGLO red dots (F, J and N) localized perfectly to the nucleus (blue) (G, K and O) of Iba1 (green) positive cells (E, I and M). Nuclear localization of the signal is a clear signal of the successful transfection. Merged imaged (H, L and P) showed that the fluorescent oligonucleotide localized to the nucleus of almost all Iba1 positive microglial cells.
Figure 8:
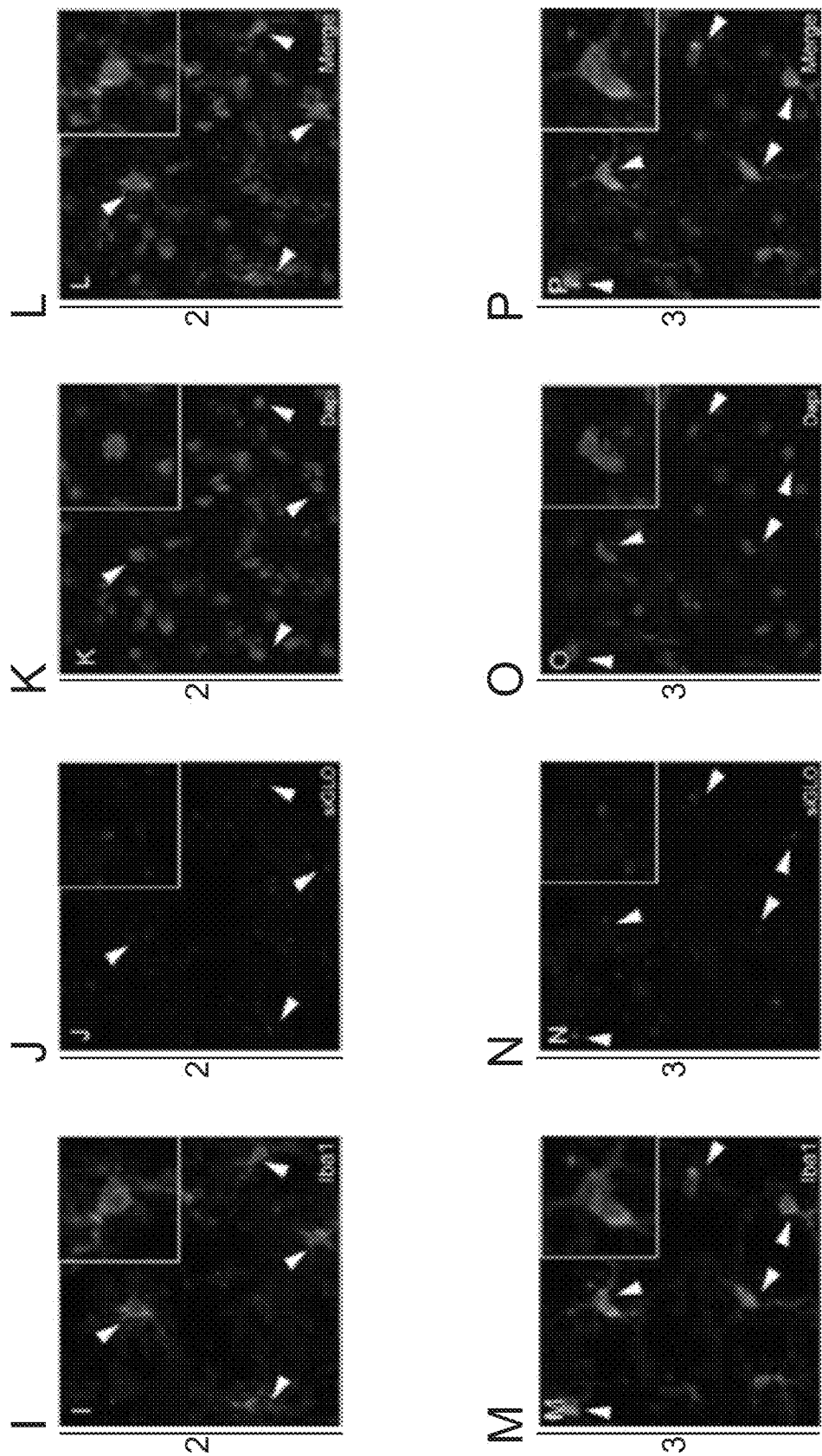

To assess the role of SRSF3 in vivo, the TLR2-luc-GFP reporter mice previously generated was used (Lalancette-Hebert et al., 2009). In this transgenic model, luciferase and GFP are co-expressed under transcriptional control of the murine TLR2 gene promoter, thus innate immune response/microglial activation can be visualized in real-time from the brains of living mice using a high resolution/high sensitivity CCD camera (Lalancette-Hebert et al., 2009; Lalancette-Hebert et al., 2012). Consistent with previous reports, the systemic LPS causes a robust induction of the TLR2 signal in activated microglia peaking 24 hrs after stimuli (Gravel et al., 2016; Lalancette-Hebert et al., 2009)(FIG. 6A-6D). As further confirmed by a double-immunofluorescence analysis of the TLR2-driven transgene GFP revealed a perfect co-localization of GFP immunostaining with the microglial marker CD11b (FIG. 6 E). Based on the results obtained in in vitro experiments, it was hypothesized that the siRNA-mediated targeted knockdown of the endogenous SRSF3 would alleviate translational repression of inflammatory genes in vivo, thus resulting in exaggerated innate immune response and the increased brain TLR2 signals. At 48 hrs after initial intranasal delivery, 20 ug of siRNA (SEQ ID NOS:8 to 11) induced an efficient knockdown resulting in 60% decrease in the expression levels of the endogenous SRSF3 protein (FIGS. 6 F and 6 G). Schematic representation of the protocol is presented in FIG. 6 H. Given that the optimal SRSF3 knockdown is obtained at 48 hrs following intranasal delivery and the peak TLR2 response in the brain occurs 24 hrs after systemic injection, to visualize the effects of the SRFF3 knockdown in vivo, the TLR2-luc-GFP mice were injected with LPS (i.p.) 24 hrs after siRNA delivery and imaged 24 hrs after. The TLR2 responses were evaluated before (baseline) (FIG. 6 I) and 24 hrs after LPS injection (FIGS. 6 J and 6 K). As shown in FIGS. 6 J and 6 K, siRNA mediated knockdown of SRSF3 induced a marked increase in the TLR2 response in vivo when compared to control (Scramble siRNA). Quantitative analysis of the biophotonic signals in FIG. 6 L showed a significant 2.18 and 3.41 fold increase in the TLR2 signal intensities in SRSF3-siRNA+LPS-24 hrs experimental group as compared to the Scramble+LPS-24 hrs or LPS-24 hrs alone. As further revealed in FIGS. 6M and 6N, immunofluorescence analysis of the brain sections of the SRSF3-siRNA+LPS-24 hrs treated animals show more activated "amoeboid-like" morphology of microglial cells when compared to Scramble+LPS-24 hrs. The quantitative analysis revealed a significant increase in the Iba1 signal in the brain sections of the SRSF3-siRNA+LPS-24 hrs treated animals when compared to corresponding control (FIG. 6 O). Importantly, the efficiency of siRNA delivery to microglia was confirm by siGLO (FIGS. 8 A to 8 P). This transfection indicator localizes to the nucleus as a clear signal of successful transfection. Finally, western blot analysis performed on the purified microglia isolated from the fresh brain homogenates by magnetic CD11b microbeads, showed that the knockdown of SRSF3 following LPS challenge alleviates translational repression of the inflammatory genes. Indeed, a marked up-regulation of the endogenous microglial protein levels of SAA3 (3.91 fold increase), LCN2 (3.15 fold increase), CCL5 (5.12 fold increase) and CCL3 (2.78 fold increase) was observed (FIGS. 6 P and 6 Q). Overall, results demonstrate that SRSF3 plays a key role in the translational control of the highly up-regulated innate immune genes in activated microglia in vivo.

Example 8

Figure 9:
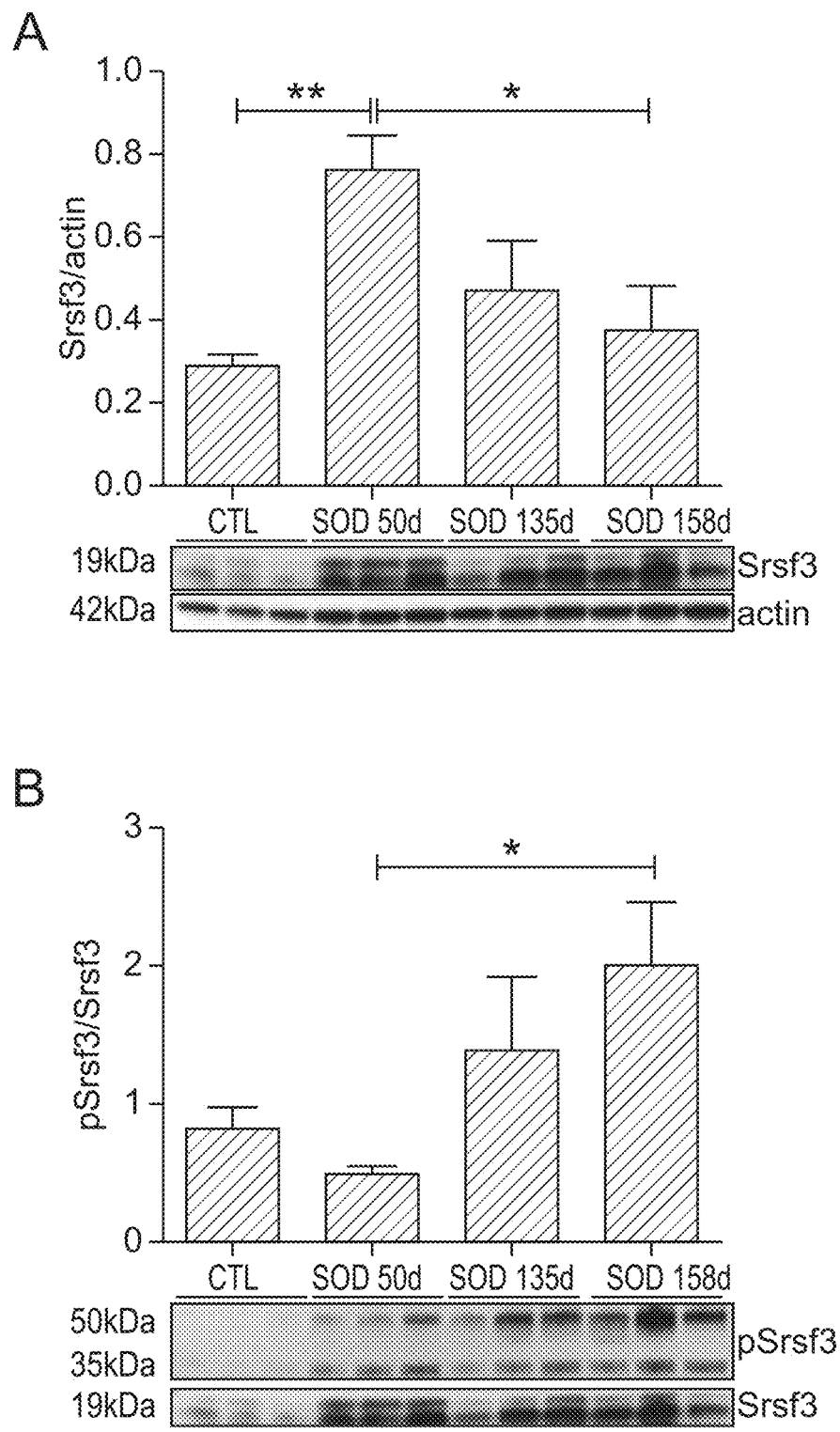
FIG. 9 SRSF3 is implicated in ALS as the level of pSRSF3 increases over time in the spinal cord of SOD1 mutant mice. Highly up-regulated mRNAs are not translated and the key mRNAs have multiple putative SRSF3 binding sites at 3'UTR. (A) Western blot analysis of SRSF3 levels are significantly increased in pre-symptomatic ALS (SOD1 mutant mice) while phosphorylation levels markedly increase with disease progression (B) (n=3; Unpaired t test; *p<0.05, **p<0.001). (C) List of 10 most up-regulated mRNAs in lumbar spinal cord microglia (158 days SOD1G93A). The transcripts marked in yellow are reported to have biomarker potential in AD/ALS and prion disease. The listed highly upregulated mRNAs are not regulated at protein level. Bioinformatics analysis revealed that the 3'UTR of Clec7a, Cst7 is highly enriched in SRSF3 binding sites.

SRSF3 is Implicated in ALS as the Level of pSRSF3 Increases Over Time in the Spinal Cord of SOD1 mutant Mice The level of phosphorylated SRSF3 was determined over the disease in presymptomatic (50 days), symptomatic (135 days) and advanced stage (158 days) using a whole spinal cord extracts. Each condition was compared to wild type mice (135 days) used as control. The monoclonal antibody (anti-phosphoepitopeSR) was used with the concentration of 1:1000. The total SRSF3 was determined using the polyclonal anti-SRSF3 (1:5000). FIG. 9 shows quantitative western blot analysis for total SRSF3 (A) and phosphorylated SRSF3 (B). The level of SRSF3 is significantly increased in pre-symptomatic ALS (SOD1 mutant mice 50 d, 135 d, 158 d) while phosphorylation levels are markedly increased with disease progression (SOD1 mutant mice 50 d, 135 d, 158 d). Also, FIG. 9 C shows that the transcriptome profile of 158 days SOD1G93A mice is similar to what was observed in LPS challenged mice, as described herein. Furthermore, bioinformatics revealed that some of the upregulated mRNA (Clec7a, Cst7) might be highly enriched in SRSF3 binding sites. The combination of these results points toward an implication of SRSF3 in ALS through translation repression of highly upregulated mRNA.

Example 9

Increased Levels of Total and pSRSF3 in Normal Aging and in a Mouse Model of Frontotemporal Dementia (TDP-43G348C)

Figure 10:
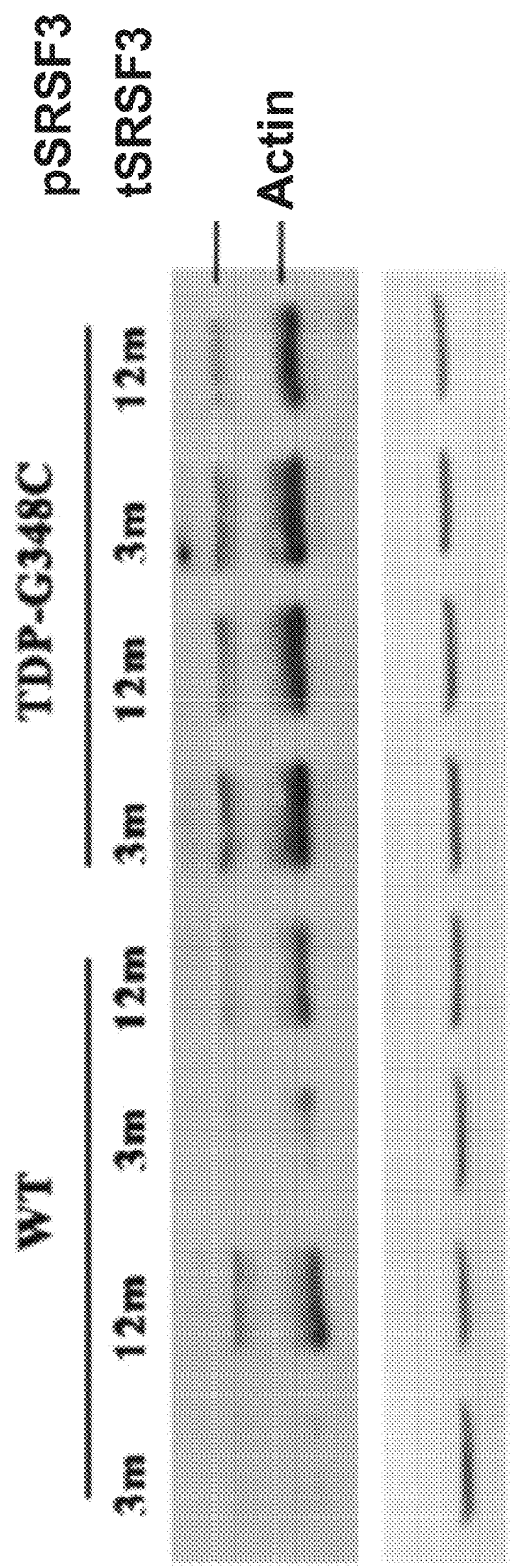
FIG. 10 Increased levels of total and pSRSF3 in normal aging and in a mouse model of Frontotemporal dementia (TDP-43$^{G348C}$). Western blot analysis of whole brain extracts.

Frontotemporal dementia (TDP-43$^{G348C}$) and normal aging mouse models were analyzed using a whole brain extracts (cortex) to determine the level of phosphorylated SRSF3 in presymptomatic TDP-43$^{G348C}$ (2-3 months) and symptomatic TDP-43$^{G348C}$ (1 year) and their corresponding controls in wild type. The monoclonal antibody (anti-phosphoepitopeSR) was used with the concentration of 1:1000. The total SRSF3 was determined using the polyclonal anti-SRSF3 (1:1000). FIG. 10 shows western blot analysis where the level of total SRSF3 and phosphorylated SRSF3 is increased in TDP-43$^{G348C}$ mice compare to their corresponding controls.

Example 10

Cerebrospinal Fluid from Sporadic ALS Patients

The human cerebrospinal fluid (CSF) from sporadic ALS patients and control patients were concentrated with acetone and used to assess the level of phosphorylated and total SRSF3 using the anti-phosphoepitopeSR antibody (1:250) and the polyclonal anti-SRSF3 antibody (1:500) respectively. The results are shown in FIG. 11 A-G.

Example 11

Development and Validation of Antisense Morpholino Oligonucleotides to Target SRSF3/pSRSF3

To validate SRSF3 as immunomodulatory therapeutic target in ALS anti-SRSF3 morpholinos (anti-SRSF3 ASOMs) targeting endogenous SRSF3 were generated and tested. As described and schematically presented in FIG. 12, the ASOM is a short chain of 25 nucleic bases that targets 5' UTR of SRSF3 and binds to complementary mRNA. As a mechanism, it blocks the initiation of SRSF3 translation and ultimately causes the knockdown of endogenous protein. The ASOM sequence is presented in FIG. 12 legend. The efficacy of the treatment was tested in in vivo settings using the mouse model of ALS (SOD1G93A mice). As demonstrated in FIG. 13, intrathecal delivery of anti-SRSF3 ASOMs induces efficient knockdown of endogenous SRSF3 in the spinal cord of ALS mice. The SRSF3 knockdown was associated with de novo synthesis of protein from targeted mRNAs (SRSF3 regulated mRNAs see FIG. 9). The results clearly show that ASOMs targeting endogenous SRSF3 can be used to induce de novo synthesis of protein and thus efficiently reprogram innate immune response in disease affected microglia. The efficacy of ASOMs was also tested to target SRSF3 and immune response at peripheral immune cells. Namely, pSRSF3 levels are increased in plasma of ALS patients and ALS mice. The efficacy of ASOMs was tested using intra-peritoneal (i.p) delivery. As shown in FIG. 14A-C, i.p. delivery of ASOMs induces efficient knockdown of endogenous SRSF3 in plasma (mouse monocytes/macrophages). Importantly i.p. delivery of ASOMs initiated at symptomatic disease had a remarkable therapeutic effect in SOD1 G93A model of ALS. As further described in FIG. 14 A,D, E. treatment with ASOMs (25 mg/kg 1× week) initiated at advanced stages of disease (after onset of paralysis) significantly increases survival of ALS mice (for 21 days). The observed increase in survival was associated with a marked improvement in sensory motor deficits evaluated in Rotarod test. Furthermore, detailed analysis of ASOMs therapeutic effects revealed that treatment with anti-SRSF3 ASOMs reverses muscle and spleen atrophy (FIGS. 15 A-D) and preserves motor neurons in the spinal cord of SOD1G93A mice. Importantly, therapeutic effect of i.p. delivered ASOMs was associated with an increase in microglial activation in the spinal cord. Taken together, the results clearly demonstrate that SFSF3 acts as regulator of immune response in ALS affected microglia/macrophages/monocytes. In view of the above, targeting endogenous SRSF3 with ASOMs in advanced stages of disease is therapeutic in ALS.

Example 12

Antibodies Targeting RRM Domain of SRSF3

An additional strategy to therapeutically modulate SRSF3 is to block and/or disrupt its interaction with the target immune mRNAs. To disrupt the interaction of SRSF3 with its target mRNAs, unique therapeutic monoclonal antibodies (Mab121) targeting RRM domain of SRSF3 were generated. The identified sequence specific to SRSF3 RRM domain (underlined in FIG. 17A) and the validation strategies to test the efficacy of monoclonal antibodies (MAbs) are shown in FIG. 17. Following immunization procedures 10 clones of MABs were obtained and as further shown in FIG. 18A, 4 clones that recognize SRSF3 peptide sequence at high affinity were selected. The validation luciferase assay performed on stably HEK cell stably transfected with PGL3 vector expressing Saa3 3'UTR (assay described in details herein) show that treatment with serum containing Mab antibody (clone #155) restored luciferase activity thus alleviating translational arrest caused by SRSF3 binding to Saa3 3'UTR (FIG. 18B). The unique immunogenic sequence is GNNGNKTELERAFGYYGPLRSV Example 13

Evidence of SRSF3-Mediated Mechanisms in Cerebral Ischemia and Alzheimer's Disease (AD). Targeting SRSF3 is Protective after Stroke Analysis of the post-ischemic inflammation revealed that SRSF3 is involved in modulation of microglial activation after stroke. As shown in FIG. 19A, levels of pSRSF3 were significantly increased after stroke while expression of total SRSF3 protein decreases. Double immunfluorescence analysis revealed that expression of pSRSF3 after stroke was restricted to Iba1 positive activated microglia. Intranasal delivery of siRNA 24 hrs after stroke induced a significant knockdown of endogenous protein (FIG. 20A-C). The intranasal delivery of siRNA as a therapeutic approach is described herein. The therapy was designed as a single dose that would transiently reprogram delayed/proregenerative phase of the immune response after stroke. siRNa mediated knockdown of endogenous SRSF3 induces a marked increase in innate immune response 3-5 day after stroke that was visualized in vivo using the TLR2 reporter mice. Importantly, delayed induction of innate immune response/microglial activation was associated with a significant decrease in the size of ischemic lesion and delayed increase in expression levels (proteins) of certain immune molecules known to be regulated by SRSF3, such as CCL3, CCL5. Hence, targeted knockdown of SRSF3 initiated 24 hrs after stroke increases delayed inflammatory response after stroke and decreases ischemic lesion (FIG. 21).

Example 14

SRSF3 Expression Patterns in Amyloid Precursor Protein (APP) Mouse Model of Alzheimer Disease (AD)

Analysis of the SRFS3 expression pattern in the brains of APP mouse model of AD revealed a marked increase in pSRSF3 levels starting at 7-9 months of age (Borchelt et al., 1997). In this mouse model this time point (7-9 months of age) coincides with the onset of cognitive deficits (FIG. 22A, B). Immunofluorescence analysis of the brains section of APP mice revealed that the expression of pSRSF3 was restricted to activated Iba1 positive microglia surrounding B amyloid plaques. pSRSF3 immunoreactivity was not detected in controls. As further shown in FIG. 23 A, to validate neuroiflammation, the expression levels of GFAP as positive control were analyzed, as increase in this protein levels and associated astrogliosis are known to be involved in inflammatory response in APP mouse model. The protein expression levels of highly regulated and disease associated mRNAs known to be induced in AD affected microglia (Kang et al 2018, Keren-Shaul et al., 2017) found also in ALS microglia (Keren-Shaul et al., 2017) were analysed and known to be regulated by SRSF3. As shown in FIG. 23 C, a part from the modest increase in CLE7A expression levels, other highly up-regulated mRNAs were not regulated at protein level (FIG. 23C,D). Intranasal delivery of anti-SRSF3 ASOMs was tested in APP mice. As shown in FIG. 24, a single dose induced an efficient knockdown of endogenous SRSF3 (duration over 1 week time period) in the brains of APP mice. Growing evidence suggest that innate immune response is deregulated in AD, thus treatment with SRSF3 antagonists—anti-SRSF3 ASOMs may have therapeutic potential in AD.

Material and Methods

DNA Constructs, Generation of Transgenic Mice and Genotyping

CD11b promoter was subcloned into pBluescript KS+ (pBSKS-CD11b). Flag-EGFP fragment was obtained by PCR using pEGFP-N3 plasmid as template (CLONTECH). The obtained fragment was introduced into pBSKS-CD11b plasmid. A 2.5 Kb BamHI/NotI fragment corresponding to the genomic DNA of 60s ribosomal protein L10a (RPL10a) was introduced into pBSKS recombinant vector. The integrity of the final construct was verified by sequencing (SEQ ID NO:1). XhoI-XhoI DNA fragment of 5.2 Kb was isolated on agarose gel for microinjection. The transgenic mice were genotyped by PCR amplification for the EGFP gene performed on tail samples. A 329 bp EGFP-fragment was amplified from F/EGFP-Rp10a transgenic mice. The experiments were performed on the adult 2-3 months old male and female mice. All experimental procedures were approved by the Laval University animal care ethics committee (protocols #17-063-1 and 14-096-4) and are in accordance with *The Guide to the Care and Use of Experimental Animals of the Canadian Council on Animal Care*.

TRAP Protocol

The TRAP protocol described by Heiman and colleagues was used with minor modifications (Heiman et al., 2008). Briefly, brain cortex samples were placed into ice-cold dissection buffer followed by a homogenization (10% wt/vol) in tissue lysis buffer. Samples were then centrifuged at 2000 g for 10 min at 4° C. 1/9 sample volume of 10% NP-40 and 1/9 sample volume of 300 mM DHPC were added to the supernatant. Samples were then incubated for 30 min at 4° C. on orbital shaker. The insoluble material was recovered by centrifugation at 20000 g for 10 min at 4° C. Each supernatant was divided in two aliquots. (One aliquot will be used for mRNA extraction and the other for peptides elution). Each sample is added directly to anti-Flag agarose affinity resin and incubated overnight at 4° C. on orbital shaker. The following day, the beads were recovered by centrifugation and washed 3 times with high-salt buffer (20 mM Hepes-KOH pH 7.3, 200 mM KCl, 12 mM MgCl2, 1% NP-40, 0.5 mM DTT, 100 µg/ml cycloheximide). The beads pellet was used either for mRNA purification or peptides purification.

Purification of mRNA from F/EGFP-RPL10a Mice after TRAP Protocol

After the last washing, the beads pellet was resuspended in 100 ul of Nanoprep lysis buffer with beta-mercaptoethanol and incubated 10 min at room temperature. The RNA cleanup was done according to the kit manufacturer's instructions (Absolutely RNA Nanoprep kit). Three biological replicates were performed for each experiment. For each replicate n=5. Collected RNA was subjected to Affymetrix mouse gene chip.

Purification of Peptides from F/EGFP-RPL10a Mice after TRAP Protocol

After the last washing, all remaining wash buffer was removed and beads pellet were resuspended in EDTA-elution buffer (10 mM Hepes-KOH pH 7.3, 150 mM KCl, 5 mM MgCl2, 20 mM EDTA, proteases inhibitors) and incubated 30 min at room temperature on orbital shaker. EDTA elution buffer was used to dissociate ribosomes and release nascent chains peptides. Eluate was recovered by centrifugation at 7000 rpm for 15 min. Collected ribosomes-associated peptides were sequenced by mass spectrometry using Orbitrap fusion mass spectrometer. Three technical replicates were performed for this experiment. n=5 per condition.

In Vivo Bioluminescence Imaging

As previously described (Gravel et al., 2011; Lalancette-Hebert et al., 2007; Lalancette-Hebert et al., 2009) the images were gathered using IVIS 200 Imaging System (CaliperLSXenogen). The data where showed as pseudo-color images indicating light intensity. Region of interest is expressed in photon per seconds per centimeter squared per steradian.

Statistical Analyses

Data were expressed as the mean±SEM from at least two independent experiments. Statistical differences between the test and control values were analyzed by applying the Student's t-test. For multiple comparisons, statistical differences were analyzed by applying the ordinary one-way ANOVA (Tukey's multiple comparisons test). Data were considered significant and indicated by "*" if the $p<0.05$, "" if $p<0.01$, "*" if $p<0.001$. Statistical analysis was performed using GraphPad Prism version 6.07 (GraphPad Software, San Diego Calif. USA).

Tissue Collection and Immunohistochemistry

Animals were sacrificed and perfused and processed as previously described (Gravel et al., 2016; Lalancette-Hebert et al., 2007; Lalancette-Hebert et al., 2012). Brains were cut into coronal section with cryostat (25-μm thick) and stored at −20° C. Brain sections were then incubated in primary antibody 1:500 rabbit polyclonal anti-Iba1 (Wako), 1:500 mouse monoclonal anti-green fluorescent protein (GFP) (Invitrogen), 1:500 rat monoclonal anti-CD11b (Serotec). The sections were then incubated in corresponding fluorescent goat secondary antiserum (Invitrogen). Fluorescent images were acquired using a Zeiss LSM 700 confocal microscope with 20× objective using a scan zoom between 1× and 2× and analyzed with Zen software.

Microglia Primary Culture

Primary cultures were prepared from the cerebral cortices of CD11brGFP transgenic pups as previously described (Lalancette-Hebert et al., 2012). The glial cell culture was maintained for 20-25 days in Dulbecco's modified eagle's medium supplemented with F12, for microglia and astrocyte isolation. Glial cell cultures were trypsinized and seeded in 10 $cm^2$ plates. Cells were treated with LPS (1 μg/ml) or vehicle. 24 hours later, primary cultures were collected and subjected to immunoprecipitation.

Affymetrix Mouse Gene 2.0 ST

Total RNA concentration was measured using a Nano-Drop ND-1000 Spectrophotometer (NanoDrop Technologies, Wilmington, Del., USA). RNA quality was assayed on an Agilent BioAnalyzer (Agilent Technologies). DNA microarray analyses were carried out with Affymetrix Mouse Gene 2.0 ST according to the Affymetrix standard protocol using 100 ng of total RNA per sample. The image data were analyzed by using the Affymetrix Expression Console Software to perform the quality control, the background subtraction and the normalization of probe set intensities with the method of Robust Multiarray Analysis (RMA). A mRNA was considered as variant if the fold change between the two compared samples was higher than 1.2 and the associated ANOVA p-value was lower than 0.05. Microarray analyses were performed by the CHU de Quebec Research Center (CHUL) Gene Expression Platform, Quebec, Canada.

Mass Spectrometry Analysis: Sample Preparation

Samples were concentrated on desalting column Amicon 3 kDa (Millipore), and washed 3 times with ammonium bicarbonate 50 mM. Protein concentration was determined by colorimetric Bradford assay. Equal amounts of protein were solubilized in the denaturation buffer. Then samples were heated to 95° C. for 5 min in a solution of DTT and iodacetamide. Finally, 1 μg trypsin was added, and the mixture was incubated at 37° C., overnight. The precipitated sodium deoxycholate was eliminated by 10 min RT incubation and 5 min RT centrifugation at 16000 g. The supernatant was desalted on C18 Empore filter. Peptides were eluted in 80% ACN-0.1% TFA, and dried in speed vac.

Mass Spectrometry Analysis: Mass Spectrometry

Samples were analysed by nanoLC/MSMS as triplicates for statistical information. For each injection, 750 ng of peptide samples were injected and separated by online reversed-phase (RP) nanoscale capillary liquid chromatography (nanoLC) and analyzed by electrospray mass spectrometry (ESI MS/MS). The experiments were performed with a Dionex UltiMate 3000 nanoRSLC chromatography system (Thermo Fisher Scientific/Dionex Softron GmbH, Germering, Germany) connected to an Orbitrap Fusion mass spectrometer (Thermo Fisher Scientific) equipped with a nanoelectrospray ion source. Mass spectra were acquired using a data dependent acquisition mode using Thermo XCalibur software version 3.0.63. Full scan mass spectra (350 to 1800 m/z) were acquired in the orbitrap using an AGC target of 4e5, a maximum injection time of 50 ms and a resolution of 120 000. Each MS scan was followed by acquisition of fragmentation MSMS spectra of the most intense ions for a total cycle time of 3 seconds (top speed mode).

Dynamic exclusion of previously fragmented peptides was set for a period of 20 sec and a tolerance of 10 ppm. Mass spectrometry analyses were performed by the Proteomics platform of the Eastern Quebec Genomic Center, CHU de Quebec, Canada. Database searching and Label Free Quantification Spectra were searched against a mouse proteins database (UniprotKB—taxonomy *Mus musculus*—84675 sequences) using the *Andromeda* module of MaxQuant software v. 1.5.0.25 (Cox and Mann, 2008). Only unique and razor peptides were used for quantification. A protein was considered as quantifiable only if at least two replicate values in one of the two samples to compare were present. A protein was considered as variant if the fold change between the two compared samples was higher than 1.2 and the associated p-value was lower than 0.05.

Cluego Analysis

Data from gene chip Affymetrix or mass spectrometry were analyzed with ClueGo application (version 2.1.6) using the cytoscape environment (3.2.1). Differentially expressed genes (with corresponding fold changes and p-values) were used to generate biological networks using different ontology sources like the Gene Ontology (GO), Kyoto Encyclopedia of Genes and Genomes (KEGG), Reactome and WikiPathways. The GO interval was between 4 (Min level) and 11 (Max level). The Kappa score was 0.7. For the enrichment of biological terms and groups, we used the two-sided (Enrichment/Depletion) tests based on the hypergeometric distribution. We set the statistical significance to 0.05 for transcriptomic result, and we used the Bonferroni adjustment to correct the p-value for the terms and the groups created by ClueGO. The leading group term is based on % genes/term vs cluster.

Luciferase Reporter Assay

Exponentially growing HEK293 or BV2 cells were seeded in 24-well culture dishes. Cells transfection was carried out according to the manufacturer's instructions (jetPRIME, Polyplus). Each transfection experiment contained 0.125 μg of reporter (pGL3-promoter and modified pGL3-promoter, Promega) and 62.5 ng of PRL-TK-*Renilla* vector (Promega) as an internal transfection control. Transfected BV2 cells were treated with LPS for O/N (1 μg/ml). Luciferase activities were measured with the dual luciferase system according to the manufacturer's instructions (Promega). Transfections were performed in triplicate. A luminometer (Bertol, Germany) was used to quantify light signals. Luciferase activities were evaluated as the ratio of Firefly luciferase to Renillaluciferase activities.

siRNA Transfection

BV2 cells were maintained in DMEM supplemented with 10% FBS and Pen/Strep. $3.5 \times 10^4$ cells/well were seeded in 24-well plates 1 day before transfection. BV2 cells were then transfected with SRSF3 siRNA (100 nM and 300 nM; ON-TARGET plus Mouse Srsf3 siRNA-SMART pool: Dharmacon) or CTL siRNA using INTERFERin siRNA transfection reagent (Polyplus) according to the manufacturer's instructions (SEQ ID NOS:8 to 11). For western blot analysis, cells were stimulated with 1 μg/ml of LPS or vehicle two days after transfection and collected for protein measurement. For luciferase reporter assay, BV2 cells were transfected with siRNA one day before DNA transfection.

Quantitative Reverse Transcriptase PCR Analysis (RT-qPCR)

BV2 cell line that stably expresses F/EGFP-RPL10a were transfected with pGL3 or pGL3-Saa3-3'UTR-wt. Forty-eight hours post-transfection, ribosomes were immunopurified according to the TRAP protocol and the mRNA cleanup was done according to the kit manufacturer's instructions (Stratagene Absolutely RNA Nanoprep kit).

Quantity of ribosomes-associated mRNA was measured using a NanoDrop ND-1000 Spectrophotometer (NanoDrop Technologies, Wilmington, Del., USA) and total RNA quality was assayed on an Agilent BioAnalyzer 2100 (Agilent Technologies, Santa Clara, Calif., USA). cDNA corresponding to 20 ng of total RNA was used to perform fluorescent-based Realtime PCR quantification using the LightCycler 480 (Roche Diagnostics, Mannheim, Del.). Reagent Light-Cycler 480 SYBRGreen I Master (Roche Diagnostics, Indianapolis, Ind., USA) was used as described by the manufacturer with 2% DMSO. A melting curve was performed to assess non-specific signal. Calculation of the number of copies of each mRNA was performed according to Luu-The et al. using second derivative method and a standard curve of Cp versus logarithm of the quantity (Luu-The et al., 2005). Normalization was performed using the reference genes shown to be genes having stable expression levels: hypoxanthine phosphoribosyltransferase 1 (HPRT1) and glyceraldehyde-3-phosphate dehydrogenase (GAPDH) (Warrington et al., 2000). Quantitative Real-Time PCR measurements were performed by the CHU de Quebec Research Center (CHUL) Gene Expression Platform, Quebec, Canada and were compliant with MIQE guidelines (Bustin et al., 2010; Bustin et al., 2009)

Intranasal Delivery of SRSF3-siRNA

Scramble-siRNA (20 µg) or SRSF3-siRNA (20 µg) (Dharmacon) was administrated intranasally in anaesthetized mice using in vivo jetPEI reagent (Polyplus) according to the manufacturer's protocol. Briefly, jetPEI and siRNA were diluted separately in 10% glucose solution (nitrogen and phosphate (N/P) ratio equal to 8). Then, siRNA and PEI solutions were mixed and incubated for 15 min at room temperature for a total of 50 µl. Mice received 25 µl of solution in each nostril.

Intraperitoneal Delivery of SRSF3 AMOS

The antisense vivo-morpholinos against SRSF3 were injected intraperitoneally (i.p.) in SOD1G93A mice starting at symptomatic disease (130/score 2) 1× week (25 mg/kg) till the end stage of disease.

siGLO Transfection

To visualize the uptake of the siRNA into CNS cells we co-transfect Scramble-siRNA or SRSF3-siRNA with siGLO Red (20 µg) oligonucleotide duplex (Dharmacon) using in vivo jetPEI reagent (N/P=8). The siGLO was used to confirm the delivery efficiency of siRNA. This transfection indicator is modified to localize into the nucleus when the cells is successfully transfected.

In Vivo Bioluminescence Imaging

As previously described (Lalancette-Hebert et al., 2009) the images were gathered using IVIS 200 Imaging System (CaliperLSXenogen). Twenty minutes prior to imaging session, the mice received intraperitoneal (i.p.) injection of the luciferase substrate D-luciferine (150 mg/kg in 0.9% saline) (CaliperLS-Xenogen). The 3D reconstruction of bioluminescent sources in the brain was accomplished by using diffuse luminescent imaging tomography (DLIT) algorithms (Living Image 3D Analysis Software, CaliperLS-Xenogen). The data where showed as pseudo-color images indicating light intensity. Region of interest is expressed in photon per seconds per centimeter squared per steradian.

Isolation of Brain Microglia with Magnetic CD11b Beads

After perfusion with ice-cold PBS, brains from mice treated with Scramble- or SRSF3-siRNA and injected with LPS (24 hrs; 5 mg/kg; i.p.) were dissected and enzymatically digested by Dispase II (invitrogen) 30 min at 37° C. with a gentle trituration each 15 minutes. Tissue debris was removed by passing cell suspension through a 70 µm cell strainer. After cells washing, cells pellet was resuspended in 30% Percoll (GE Healthcare) and centrifuged for 10 min at 700 g. The supernatant containing the myelin was removed and the pelleted cells were washed with HBSS and subjected to magnetic CD11b beads separation according to the kit manufacturer's instructions (CD11b (Microglia), Micro-Beads human and mouse; Miltenyi Biotec). Collected cells were subjected to western blot analysis.

Samples Preparation for Western Blot (Input)

Brains from saline/LPS-injected mice or microglia cells purified with CD11b magnetic beads were lysed by urea lysis buffer (6M Urea, 1% SDS, 50 mM Tris-HCl pH 7.4, 150 mM NaCL), sonicated and quantified using the Bradford protein assay (Bio-Rad) with bovine serum albumin as standard. Samples were resolved on SDS-PAGE gels and transferred to PVDF membranes (Millipore).

Antibodies (Western Blot)

Rabbit polyclonal anti-mouse SAA3; 1:1000 (Santa Cruz); the immunogen of the anti-SAA3 antibody covers most of the protein from amino acid 38 to 122 (total aa: 128). Rabbit polyclonal anti-mouse LCN2; 1:1000 (Abcam); For anti-LCN2 antibody, the immunogen used is close to the amino acid 40 (total aa: 224), rabbit polyclonal anti-mouse CCL5; 1:1000 (LS-Bio); the rabbit polyclonal antibody anti-CCl5 is made against amino acid 24-91 (total aa: 198). Rabbit polyclonal anti-mouse CAP2; 1:1000 (Origene). Rabbit polyclonal anti-mouse CCL3; 1:1000 (Abcam). Rabbit polyclonal anti-mouse SRSF3; 1:1000 (Abcam). Mouse monoclonal Anti-Phosphoepitope SR proteins clone 1H4; 1:1000 (Millipore). Mouse monoclonal anti-☐actin antibody was used as loading control; 1:30000 (Millipore).

REFERENCES

Anderson, P. (2010). Post-transcriptional regulons coordinate the initiation and resolution of inflammation. Nature reviews. Immunology 10, 24-35.

Beutner, C., Linnartz-Gerlach, B., Schmidt, S. V., Beyer, M., Mallmann, M. R., Staratschek-Jox, A., Schultze, J. L., and Neumann, H. (2013). Unique transcriptome signature of mouse microglia. Glia 61, 1429-1442.

Bindea, G., Galon, J., and Mlecnik, B. (2013). CluePedia Cytoscape plugin: pathway insights using integrated experimental and in silico data. Bioinformatics 29, 661-663.

Bustin, S. A., Beaulieu, J. F., Huggett, J., Jaggi, R., Kibenge, F. S., Olsvik, P. A., Penning, L. C., and Toegel, S. (2010). MIQE precis: Practical implementation of minimum standard guidelines for fluorescence-based quantitative real-time PCR experiments. BMC Mol Biol 11, 74.

Bustin, S. A., Benes, V., Garson, J. A., Hellemans, J., Huggett, J., Kubista, M., Mueller, R., Nolan, T., Pfaffl, M. W., Shipley, G. L., et al. (2009). The MIQE guidelines: minimum information for publication of quantitative real-time PCR experiments. Clin Chem 55, 611-622.

Bindea, G., Mlecnik, B., Hackl, H., Charoentong, P., Tosolini, M., Kirilovsky, A., Fridman, W. H., Pages, F., Trajanoski, Z., and Galon, J. (2009). ClueGO: a Cytoscape plug-in to decipher functionally grouped gene ontology and pathway annotation networks. Bioinformatics 25, 1091-1093.

Borchelt D R, Ratovitski T, van Lare J, Lee M K, Gonzales V, Jenkins N A, Copeland N G, Price D L, Sisodia S S. Accelerated amyloid deposition in the brains of transgenic mice coexpressing mutant presenilin 1 and amyloid precursor proteins. Neuron. 1997 October; 19(4):939-45.

Boutej, H. et al. (2017). Diverging mRNA and Protein Networks in Activated Microglia Reveal SRSF3 Suppresses Translation of Highly Upregulated Innate Immune Transcripts. Cell Reports 21, 3220-3233

Butovsky, O., Jedrychowski, M. P., Moore, C. S., Cialic, R., Lanser, A. J., Gabriely, G., Koeglsperger, T., Dake, B., Wu, P. M., Doykan, C. E., et al. (2014). Identification of a unique TGF-beta-dependent molecular and functional signature in microglia. Nature neuroscience 17, 131-143.

Cao, J., and Geballe, A. P. (1996). Inhibition of nascent-peptide release at translation termination. Molecular and cellular biology 16, 7109-7114.

Carpenter, S., and Fitzgerald, K. A. (2015). Transcription of inflammatory genes: long noncoding RNA and beyond. J Interferon Cytokine Res 35, 79-88.

Carpenter, S., Ricci, E. P., Mercier, B. C., Moore, M. J., and Fitzgerald, K. A. (2014). Post-transcriptional regulation of gene expression in innate immunity. Nature reviews. Immunology 14, 361-376.

Chen, Z., Jalabi, W., Shpargel, K. B., Farabaugh, K. T., Dutta, R., Yin, X., Kidd, G. J., Bergmann, C. C., Stohlman, S. A., and Trapp, B. D. (2012). Lipopolysaccharide-induced microglial activation and neuroprotection against experimental brain injury is independent of hematogenous TLR4. J Neurosci 32, 11706-11715.

Chen, Z., and Trapp, B. D. (2016). Microglia and neuroprotection. Journal of neurochemistry 136 Suppl 1, 10-17.

Ciafre, S. A., and Galardi, S. (2013). microRNAs and RNA-binding proteins: a complex network of interactions and reciprocal regulations in cancer. RNA Biol 10, 935-942.

Cox, J., and Mann, M. (2008). MaxQuant enables high peptide identification rates, individualized p.p.b.-range mass accuracies and proteome-wide protein quantification. Nat Biotechnol 26, 1367-1372.

Danoff, T. M., Lalley, P. A., Chang, Y. S., Heeger, P. S., and Neilson, E. G. (1994). Cloning, genomic organization, and chromosomal localization of the Scya5 gene encoding the murine chemokine RANTES. J Immunol 152, 1182-1189.

David, S., and Kroner, A. (2011). Repertoire of microglial and macrophage responses after spinal cord injury. Nature reviews 12, 388-399.

Doyle, J. P., Dougherty, J. D., Heiman, M., Schmidt, E. F., Stevens, T. R., Ma, G., Bupp, S., Shrestha, P., Shah, R. D., Doughty, M. L., et al. (2008). Application of a translational profiling approach for the comparative analysis of CNS cell types. Cell 135, 749-762.

Flo, T. H., Smith, K. D., Sato, S., Rodriguez, D. J., Holmes, M. A., Strong, R. K., Akira, S., and Aderem, A. (2004). Lipocalin 2 mediates an innate immune response to bacterial infection by sequestrating iron. Nature 432, 917-921.

Gao, B., and Roux, P. P. (2015). Translational control by oncogenic signaling pathways. Biochim Biophys Acta 1849, 753-765.

Glisovic, T., Bachorik, J. L., Yong, J., and Dreyfuss, G. (2008). RNA-binding proteins and post-transcriptional gene regulation. FEBS Lett 582, 1977-1986.

Gowing, G., Vallieres, L., and Julien, J. P. (2006). Mouse model for ablation of proliferating microglia in acute CNS injuries. Glia 53, 331-337.

Gravel, M., Beland, L. C., Soucy, G., Abdelhamid, E., Rahimian, R., Gravel, C., and Kriz, J. (2016). IL-Controls Early Microglial Phenotypes and Disease Onset in ALS Caused by Misfolded Superoxide Dismutase 1. J Neurosci 36, 1031-1048.

Hanisch, U. K., and Kettenmann, H. (2007). Microglia: active sensor and versatile effector cells in the normal and pathologic brain. Nature neuroscience 10, 1387-1394.

Heiman, M., Schaefer, A., Gong, S., Peterson, J. D., Day, M., Ramsey, K. E., Suarez-Farinas, M., Schwarz, C., Stephan, D. A., Surmeier, D. J., et al. (2008). A translational profiling approach for the molecular characterization of CNS cell types. Cell 135, 738-748.

Hickman, S. E., Kingery, N. D., Ohsumi, T. K., Borowsky, M. L., Wang, L. C., Means, T. K., and El Khoury, J. (2013). The microglial sensome revealed by direct RNA sequencing. Nature neuroscience 16, 1896-1905.

Jiang, P., and Coller, H. (2012). Functional interactions between microRNAs and RNA binding proteins. Microrna 1, 70-79.

Jin, M., Jang, E., and Suk, K. (2014). Lipocalin-2 Acts as a Neuroinflammatogen in Lipopolysaccharide-injected Mice. Exp Neurobiol 23, 155-162.

Kang S S, Ebert M T W, Baker K E, Cook C, Wang X, Sens J P, Kocher Jeanne-Pierre, Petrucelli L, Fryer J D. Microglial translational profiling reveals a convergent Apoe pathway from aging, amyloid and tau. J Exp Med, Aug. 13, 2018.

Keren-Shaul H, Spinrad A, Weiner A, Matcovitch-Natan O, Dvir-Szternfeld R, Ulland T K, David E, Baruch K, Lara-Astaiso D, Toth B, Itzkovitz S, Colonna M, Schwartz M, Amit. A Unique Microglia Type Associated with Restricting Development of Alzheimer's Disease. Cell. 2017 Jun. 15; 169(7):1276-1290

Kreutzberg G W. Microglia: a sensor for pathological events in the CNS. Trends Neurosci. 1996 August; 19(8):312-8. Review.

Kierdorf, K., and Prinz, M. (2013). Factors regulating microglia activation. Front Cell Neurosci 7, 44.

Kim, J. H., Park, K. W., Lee, E. W., Jang, W. S., Seo, J., Shin, S., Hwang, K. A., and Song, J. (2014). Suppression of PPARgamma through MKRN1-mediated ubiquitination and degradation prevents adipocyte differentiation. Cell Death Differ 21, 594-603.

Laflamme, N., Soucy, G., and Rivest, S. (2001). Circulating cell wall components derived from gram-negative, not gram-positive, bacteria cause a profound induction of the gene-encoding Toll-like receptor 2 in the CNS. Journal of neurochemistry 79, 648-657.

Lalancette-Hebert, M., Gowing, G., Simard, A., Weng, Y. C., and Kriz, J. (2007). Selective ablation of proliferating microglial cells exacerbates ischemic injury in the brain. J Neurosci 27, 2596-2605.

Lalancette-Hebert, M., Julien, C., Cordeau, P., Bohacek, I., Weng, Y. C., Calon, F., and Kriz, J. (2011). Accumulation of dietary docosahexaenoic acid in the brain attenuates acute immune response and development of postischemic neuronal damage. Stroke; a journal of cerebral circulation 42, 2903-2909.

Lalancette-Hebert, M., Phaneuf, D., Soucy, G., Weng, Y. C., and Kriz, J. (2009). Live imaging of Toll-like receptor 2 response in cerebral ischaemia reveals a role of olfactory bulb microglia as modulators of inflammation. Brain 132, 940-954.

Lalancette-Hebert, M., Swarup, V., Beaulieu, J. M., Bohacek, I., Abdelhamid, E., Weng, Y. C., Sato, S., and Kriz, J. (2012). Galectin-3 is required for resident microglia activation and proliferation in response to ischemic injury. J Neurosci 32, 10383-10395.

Lee, S., Jha, M. K., and Suk, K. (2015). Lipocalin-2 in the Inflammatory Activation of Brain Astrocytes. Crit Rev Immunol 35, 77-84.

Luu-The, V., Paquet, N., Calvo, E., and Cumps, J. (2005). Improved real-time RT-PCR method for high-throughput measurements using second derivative calculation and double correction. Biotechniques 38, 287-293.

Madeddu, S., Woods, T. A., Mukherjee, P., Sturdevant, D., Butchi, N. B., and Peterson, K. E. (2015). Identification of Glial Activation Markers by Comparison of Transcriptome Changes between Astrocytes and Microglia following Innate Immune Stimulation. PloS one 10, e0127336.

Manley, J. L., and Krainer, A. R. (2010). A rational nomenclature for serine/arginine-rich protein splicing factors (SR proteins). Genes Dev 24, 1073-1074.

Medzhitov, R., and Horng, T. (2009). Transcriptional control of the inflammatory response. Nature reviews. Immunology 9, 692-703.

Mino, T., Murakawa, Y., Fukao, A., Vandenbon, A., Wessels, H. H., Ori, D., Uehata, T., Tartey, S., Akira, S., Suzuki, Y., et al. (2015). Regnase-1 and Roquin Regulate a Common Element in Inflammatory mRNAs by Spatiotemporally Distinct Mechanisms. Cell 161, 1058-1073.

Misteli, T., and Spector, D. L. (1997). Protein phosphorylation and the nuclear organization of pre-mRNA splicing. Trends Cell Biol 7, 135-138.

Nilson, S. E., and Assmann, S. M. (2007). The control of transpiration. Insights from *Arabidopsis*. Plant Physiol 143, 19-27.

O'Brien, K. D., and Chait, A. (2006). Serum amyloid A: the "other" inflammatory protein. Curr Atheroscler Rep 8, 62-68.

Paz, I., Kosti, I., Ares, M., Jr., Cline, M., and Mandel-Gutfreund, Y. (2014). RBPmap: a web server for mapping binding sites of RNA-binding proteins. Nucleic Acids Res 42, W361-367.

Prinz, M., and Priller, J. (2014). Microglia and brain macrophages in the molecular age: from origin to neuropsychiatric disease. Nature reviews 15, 300-312.

Ransohoff, R. M., and Brown, M. A. (2012). Innate immunity in the central nervous system. The Journal of clinical investigation 122, 1164-1171.

Schwartz, M., and Shechter, R. (2010). Systemic inflammatory cells fight off neurodegenerative disease. Nat Rev Neurol 6, 405-410.

Shannon, P., Markiel, A., Ozier, O., Baliga, N. S., Wang, J. T., Ramage, D., Amin, N., Schwikowski, B., and Ideker, T. (2003). Cytoscape: a software environment for integrated models of biomolecular interaction networks. Genome Res 13, 2498-2504.

Sharma, K., Schmitt, S., Bergner, C. G., Tyanova, S., Kannaiyan, N., Manrique-Hoyos, N., Kongi, K., Cantuti, L., Hanisch, U.K., Philips, M. A., et al. (2015). Cell type- and brain region-resolved mouse brain proteome. Nature neuroscience 18, 1819-1831.

Sonenberg, N., and Hinnebusch, A. G. (2009). Regulation of translation initiation in eukaryotes: mechanisms and biological targets. Cell 136, 731-745.

Tremblay, M. E., Stevens, B., Sierra, A., Wake, H., Bessis, A., and Nimmerjahn, A. (2011). The role of microglia in the healthy brain. J Neurosci 31, 16064-16069.

Warrington, J. A., Nair, A., Mahadevappa, M., and Tsyganskaya, M. (2000). Comparison of human adult and fetal expression and identification of 535 housekeeping/maintenance genes. Physiol Genomics 2, 143-147.

Zhang, Y., Chen, K., Sloan, S. A., Bennett, M. L., Scholze, A. R., O'Keeffe, S., Phatnani, H. P., Guarnieri, P., Caneda, C., Ruderisch, N., et al. (2014). An RNA-sequencing transcriptome and splicing database of glia, neurons, and vascular cells of the cerebral cortex. J Neurosci 34, 11929-11947.

Zhang R, Gascon R, Miller R G, Gelinas D F, Mass J, Hadlock K, Jin X, Reis J, Narvaez A, McGrath M S (2005). Evidence for systemic immune system alterations in sporadic amyotrophic lateral sclerosis (sALS). J. Neuroimmunol 159: 215-224.

Zhang R, Miller R G, Gascon R, Champion S, Katz J, Lancero M, Narvaez A, Honrada R, Ruvalcaba D, McGrath M S (2009). Circulating endotoxin and systemic immune activation in sporadic amyotrophic lateral sclerosis (sALS). J Neuroimmunol 206: 121-124.

Zhang R, Miller R G, Madison C, Jin X, Honrada R, Harris W, Katz J, Forshew D A, McGrath M S (2013). Systemic immune system alterations in early stages of Alzheimer's disease. J Neuroimmunol 256: 38-42.

---

The invention claimed is:

1. A method for:
   the treatment of a neurological condition which is vascular dementia, frontotemporal lobar degeneration (FTD), Alzheimer, Amyotrophic Lateral Sclerosis (ALS), Progressive bulbar palsy (PBP), Primary lateral sclerosis (PLS), Kennedy's Disease or Parkinson's disease;
   the method comprising administering an effective amount of at least one SRSF3 agent which is an antibody or an antisense/iRNA to a human patient in need thereof, wherein the SRSF3 agent inhibits expression or function of SRSF3.

2. The method of claim 1, wherein the SRSF3 agent inhibits the activity or function of a SRSF3 which is phosphorylated.

3. The method of claim 1, for the treatment of FTD or ALS.

4. The method of claim 1, wherein the SRSF3 agent is an antisense oligonucleotide comprising 10 to 30 contiguous nucleotides in length targeting SRSF3, wherein the contiguous sequence of the oligonucleotide is at least 90% complementary to a region of the human SRSF3 pre-mRNA sequence 5'UTR (SEQ ID NO: 19) upstream of the start codon (ATG) or overlapping with said start codon.

5. The method of claim 4, wherein the contiguous nucleotide sequence of the oligonucleotide is 100% complementary to a region of the human SRSF3 pre-mRNA sequence 5'UTR (SEQ ID NO: 19) upstream of the start codon (ATG) or overlapping with said start codon.

6. The method of claim 5, wherein the SRSF3 agent is a morpholino antisense oligonucleotide.

7. The method of claim 4, wherein the antisense oligonucleotide hybridizes with the 5'UTR of the SRSF3 mRNA and inhibits or reduces the translation of SRSF3.

8. The method of claim 7, wherein the SRSF3 agent is a morpholino antisense oligonucleotide.

9. The method of claim 4, wherein the antisense oligonucleotide comprises the sequence: 5'-CCAATGGACAG-GAATCACGATGCAT-3' (SEQ ID NO: 17).

10. The method of claim 9, wherein the SRSF3 agent is a morpholino antisense oligonucleotide.

11. The method of claim 4, wherein the SRSF3 agent is a morpholino antisense oligonucleotide.

12. The method of claim 1, wherein the SRSF3 agent is an antibody.

13. The method of claim 12, wherein the antibody is a monoclonal antibody, single chain variant fragment (scFv), a single chain variant-Fc fragment (scFv-Fc), a minibody, a diabody, a Fab fragment, F(ab')2 fragment, or Fv fragment.

14. The method of claim 13, wherein the antibody is a humanized antibody.

15. The method of claim 13, wherein the antibody
   a. specifically binds a region of SRSF3 comprising at least a part of the RRM domain (SEQ ID NO:13);
   b. specifically binds a region of SRSF3 comprising at least the SRSF3 phosphorylation site and at least a part of the RS domain of SRSF3 (SEQ ID NO:14); or
   c. specifically binds to a region of SRSF3 comprising SEQ ID NO:20.

* * * * *